United States Patent
Sharma et al.

(10) Patent No.: US 8,712,529 B2
(45) Date of Patent: *Apr. 29, 2014

(54) DEVICE AND IMPLANTATION SYSTEM FOR ELECTRICAL STIMULATION OF BIOLOGICAL SYSTEMS

(75) Inventors: Virender K. Sharma, Paradise Valley, AZ (US); Matthew Joseph Gani, Seattle, WA (US); Paul V. Goode, Cherry Hill, NJ (US); Bevil Hogg, Soquel, CA (US); Jay Miazga, Seattle, WA (US); Shai Policker, Tenafly, NJ (US); Kaila Raby, Redmond, WA (US)

(73) Assignee: EndoStim, Inc., St. Louis, MO (US)

( * ) Notice: Subject to any disclaimer, the term of this patent is extended or adjusted under 35 U.S.C. 154(b) by 92 days.

This patent is subject to a terminal disclaimer.

(21) Appl. No.: 13/041,063

(22) Filed: Mar. 4, 2011

(65) Prior Publication Data

US 2011/0307027 A1 Dec. 15, 2011

Related U.S. Application Data

(60) Provisional application No. 61/310,755, filed on Mar. 5, 2010, provisional application No. 61/318,843, filed on Mar. 30, 2010, provisional application No. 61/328,702, filed on Apr. 28, 2010, provisional application No. 61/371,146, filed on Aug. 5, 2010, provisional application No. 61/384,105, filed on Sep. 17, 2010, provisional application No. 61/414,378, filed on Nov. 16, 2010, provisional application No. 61/422,967, filed on Dec. 14, 2010, provisional application No. 61/444,849, filed on Feb. 21, 2011.

(51) Int. Cl.
*A61N 1/36* (2006.01)

(52) U.S. Cl.
USPC .......................................................... 607/40

(58) Field of Classification Search
USPC .......................................................... 607/40
See application file for complete search history.

(56) References Cited

U.S. PATENT DOCUMENTS

| 4,612,934 A | 9/1986 | Borkan |
| 5,117,827 A | 6/1992 | Stuebe |

(Continued)

FOREIGN PATENT DOCUMENTS

| WO | 0061223 A1 | 10/2000 |
| WO | 0061224 A1 | 10/2000 |

(Continued)

OTHER PUBLICATIONS

Christensen et al., "Physiologic Specialization at Esophagogastric Junction in Three Species", American Journal of Physiology, vol. 225, No. 6, Dec. 1973, 1265-1270.

(Continued)

*Primary Examiner* — Joseph Dietrich
(74) *Attorney, Agent, or Firm* — Novel IP

(57) ABSTRACT

The present specification discloses devices and methodologies for the treatment of GERD. Individuals with GERD may be treated by implanting a stimulation device within the patient's lower esophageal sphincter and applying electrical stimulation to the patient's lower esophageal sphincter, in accordance with certain predefined protocols. The presently disclosed devices have a simplified design because they do not require sensing systems capable of sensing when a person is engaged in a wet swallow and have improved energy storage requirements.

98 Claims, 30 Drawing Sheets

(56) References Cited

U.S. PATENT DOCUMENTS

| | | |
|---|---|---|
| 5,231,988 A | 8/1993 | Wernicke |
| 5,292,344 A | 3/1994 | Douglas |
| 5,423,872 A | 6/1995 | Cigaina |
| 5,690,691 A | 11/1997 | Chen |
| 5,716,385 A | 2/1998 | Mittal |
| 5,836,994 A | 11/1998 | Bourgeois |
| 5,861,044 A | 1/1999 | Crenshaw |
| 6,041,258 A | 3/2000 | Cigaina |
| 6,091,992 A | 7/2000 | Bourgeois |
| 6,097,984 A | 8/2000 | Douglas |
| 6,216,039 B1 | 4/2001 | Bourgeois |
| 6,285,897 B1 | 9/2001 | Kilcoyne |
| 6,321,124 B1 | 11/2001 | Cigaina |
| 6,381,495 B1 | 4/2002 | Jenkins |
| 6,449,511 B1 | 9/2002 | Mintchev |
| 6,510,332 B1 | 1/2003 | Greenstein |
| 6,587,719 B1 | 7/2003 | Barrett |
| 6,591,137 B1 | 7/2003 | Fischell |
| 6,611,715 B1 | 8/2003 | Boveja |
| 6,615,084 B1 | 9/2003 | Cigaina |
| 6,678,561 B2 | 1/2004 | Forsell |
| 6,754,536 B2 | 6/2004 | Swoyer |
| 6,760,626 B1 | 7/2004 | Boveja |
| 6,826,428 B1 | 11/2004 | Chen |
| 6,832,114 B1 | 12/2004 | Whitehurst |
| 6,879,859 B1 | 4/2005 | Boveja |
| 6,901,295 B2 | 5/2005 | Sharma |
| 7,006,871 B1 | 2/2006 | Darvish |
| 7,076,306 B2 | 7/2006 | Marchal |
| 7,114,502 B2 | 10/2006 | Schulman |
| 7,146,216 B2 | 12/2006 | Bumm |
| 7,310,557 B2 | 12/2007 | Maschino |
| 2003/0014086 A1* | 1/2003 | Sharma .......................... 607/40 |
| 2003/0144708 A1 | 7/2003 | Starkebaum |
| 2004/0012088 A1 | 1/2004 | Fukasawa et al. |
| 2004/0015201 A1 | 1/2004 | Greenstein |
| 2004/0024428 A1 | 2/2004 | Barrett |
| 2004/0039427 A1 | 2/2004 | Barrett |
| 2004/0172088 A1 | 9/2004 | Knudson |
| 2004/0193229 A1 | 9/2004 | Starkebaum |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131486 A1 | 6/2005 | Boveja |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2006/0036293 A1 | 2/2006 | Whitehurst |
| 2006/0064037 A1 | 3/2006 | Shalon et al. |
| 2006/0116736 A1 | 6/2006 | DiLorenzo |
| 2006/0167498 A1 | 7/2006 | DiLorenzo |
| 2006/0206160 A1 | 9/2006 | Cigaina |
| 2007/0106337 A1 | 5/2007 | Errico |
| 2007/0162085 A1 | 7/2007 | DiLorenzo |
| 2008/0021512 A1 | 1/2008 | Knudson |
| 2008/0086179 A1 | 4/2008 | Sharma |
| 2008/0154191 A1 | 6/2008 | Gobel |
| 2009/0132001 A1 | 5/2009 | Soffer et al. |
| 2009/0264951 A1 | 10/2009 | Sharma |

FOREIGN PATENT DOCUMENTS

| | | |
|---|---|---|
| WO | 0243467 A2 | 6/2002 |
| WO | 2005051486 A1 | 9/2005 |
| WO | 2009114008 A1 | 9/2009 |

OTHER PUBLICATIONS

Ellis et al., "The Prevention of Experimentally Induced Reflux by Electrical Stimulation of the Distal Esophagus", American Journal of Surgery, vol. 115, Apr. 1968, 482-487.

Gonzalez et al., "Different Responsiveness of Excitatory and Inhibitory Enteric Motor Neurons in the Human Esophagus to Electrical Field Stimulation and to Nicotine", Am J Physiol Gastrointest Liver Physiol, 287:G299-G306, 2004.

Kahrilas et al., "Impact of Fundoplication on Bolus Transit Across Esophagogastric Junction", American Physiological Society, 1998, 1386-1393.

Kamath et al., "Neurocardiac and Cerebral Responses Evoked by Esophageal Vago-Afferent Stimulation in Humans: Effects of Varying Intensities", Cardiovascular Research, 40 (1998) 591-599.

Lund et al., "Electrical Stimulation of Esophageal Smooth Muscle and Effects of Antagonists", American Journal of Physiology, vol. 217, No. 5, Nov. 1969, 1369-1374.

Related U.S. Appl. No. 13/041,098, filed Mar. 4, 2011.

Related U.S. Appl. No. 13/041,114, filed Mar. 4, 2011.

Related U.S. Appl. No. 13/041,116, filed Mar. 4, 2011.

Stein et al., "Three-dimensional Imaging of the Lower Esophageal Sphincter in Gastroesophageal Reflux Disease," Annual Meeting of the American Surgical Association, Apr. 11-13, 1991, 374-383.

* cited by examiner

- Lead Placement Combinations
  - AB
  - AB or CD
  - AC / BD Alternating
  - AB / CD Alternating
  - AB Vs. CD

DEVICE AND IMPLANTATION SYSTEM FOR ELECTRICAL STIMULATION OF BIOLOGICAL SYSTEMS

CROSS REFERENCE

This application relies on U.S. Patent Provisional Nos. 61/310,755, filed on Mar. 5, 2010, 61/318,843, filed on Mar. 30, 2010, 61/328,702, filed on Apr. 28, 2010, 61/371,146, filed on Aug. 5, 2010, 61/384,105, filed on Sep. 17, 2010, 61/414,378, filed on Nov. 16, 2010, 61/422,967, filed on Dec. 14, 2010, and 61/444,849, filed on Feb. 21, 2011, for priority. Each of the above applications are hereby incorporated by reference in their entireties.

FIELD OF THE INVENTION

This invention relates generally to a method and apparatus for electrical stimulation of the biological systems. More particularly, this invention relates to a method and apparatus for treating gastroesophageal reflux disease (GERD) by electrically stimulating a portion of the gastrointestinal system.

BACKGROUND OF THE INVENTION

Gastro-esophageal reflux disease (GERD) is a common problem and is expensive to manage in both primary and secondary care settings. This condition results from exposure of esophageal mucosa to gastric acid and bile as the gastroduodenal content refluxes from the stomach into the esophagus. The acid and bile damages the esophageal mucosa resulting in heartburn, ulcers, bleeding, and scarring, and long term complications such as Barrett's esophagus (pre-cancerous esophageal lining) and adeno-cancer of the esophagus.

Lifestyle advice and antacid therapy are advocated as first line treatment for the disease. However, since most patients with moderate to severe cases of GERD do not respond adequately to these first-line measures and need further treatment, other alternatives including pharmacological, endoscopic, and surgical treatments are employed.

The most commonly employed pharmacological treatment is daily use of H2 receptor antagonists (H2RAs) or proton-pump inhibitors (PPIs) for acid suppression. Since gastroesophageal reflux disease usually relapses once drug therapy is discontinued, most patients with the disease, therefore, need long-term drug therapy. However, daily use of PPIs or H2RAs is not universally effective in the relief of GERD symptoms or as maintenance therapy. Additionally, not all patients are comfortable with the concept of having to take daily or intermittent medication for the rest of their lives and many are interested in nonpharmacological options for managing their reflux disease.

Several endoscopic procedures for the treatment of GERD have been tried. These procedures can be divided into three approaches: endoscopic suturing wherein stitches are inserted in the gastric cardia to plicate and strengthen the lower esophageal sphincter, endoscopic application of energy to the lower esophagus, and injection of bulking agents into the muscle layer of the distal esophagus. These procedures, however, are not without their risks, besides being technically demanding and involving a long procedure time. As a result, these procedures have largely been discontinued.

Open surgical or laparoscopic fundoplication is also used to correct the cause of the disease. However, surgical procedures are associated with significant morbidity and small but not insignificant mortality rates. Moreover, long-term follow-up with patients treated by surgery suggests that many patients continue to need acid suppressive medication. There is also no convincing evidence that fundoplication reduces the risk of esophageal adenocarcinoma in the long term.

While electrical stimulation has been suggested for use in the treatment of GERD, an effective electrical stimulation system has yet to be demonstrated. In particular, the prior art teaches that effective electrical stimulation requires active, real-time sensing for a patient's swallow and, based on a sensed swallow, to immediately cease stimulation. For example, certain prior art approaches require the constant sensing of certain physiological changes in the esophagus, such as changes in esophageal pH, to detect acid reflux and/or esophageal motility and, based on such sensed changes, initiating or terminating an electrical stimulation to instantaneously close or open the LES, respectively, thereby avoiding an acid reflux episode. Other prior art approaches require continuous stimulation with sensing for swallow and stopping stimulation to allow for normal swallow to happen. This creates a complex device and has not proven to be feasible or effective in practice.

Therefore, there is still a need for a safe and effective method of treatment that can help alleviate symptoms of GERD in the long term, without adversely affecting the quality of life of the patients. In particular, there is a need for simple, efficient GERD device and treatment methods that do not inhibit a patient from swallowing and do not rely on an instantaneous response from the patient's LES to avoid episodes of acid reflux. There is a need for treatment protocols and devices which are programmed to implement such protocols, which can be easily programmed and do not require complex physiologic sensing mechanisms in order to operate effectively and safely. Moreover, there is not only a need for better devices in stimulation based therapies, but there is also a need for a safe and minimally invasive method and system that enables easy and expeditious deployment of such devices at any desired location in the body.

It is further desirable to have a system for the treatment of GERD which includes a stimulator and an optional sensor adapted to be placed in a patient's LES tissue.

It is further desirable to have a system for the treatment of GERD which includes an active implantable medical device (AIMD) and temporary sensor adapted to be placed in a patient's GI lumen where the sensors are designed to naturally dissolve or pass out through the lumen and the AIMD is adapted to dynamically acquire, process, measure the quality of, and use sensed data only when the sensor is present.

It is further desirable to have a system for the temporary treatment of GERD which includes an AIMD, which is adapted to be placed in a patient's GI lumen, designed to naturally dissolve or pass out through the lumen, and is adapted to deliver electrical stimulation to tissue at or in the vicinity of the LES. Such temporary stimulation scheme can additionally be used for pre-screening of patients likely to benefit from permanent stimulation.

It would further be desirable for the stimulator to use periodic or occasional sensing data to improve the treatment of GERD by dynamically detecting when a sensor is present, determining when a sensor is transmitting, or capable of transmitting, data, and processing the sensed data using an application having a special mode which opportunistically uses the sensed data to change stimulation parameters.

It is also desirable to automate the setting or calibration of some or all device parameters in order to reduce the need for medical follow-up visits, reduce burdens on healthcare providers and patients, decrease the rate of programming mistakes, and improve outcomes, thereby improving the treatment of GERD.

SUMMARY OF THE INVENTION

In one embodiment, the present invention provides a system for increasing pressure of a patient's lower esophageal sphincter (LES), comprising: at least one electrode contacting the LES; a waveform generator coupled to the electrodes; and a controller configured to electrically stimulate the LES to increase the pressure of the LES, and maintain an average pressure of the LES above a pressure level which reduces at least one of a frequency of occurrence or an intensity of acid reflux symptoms in the patient both during and after stimulation by controlling the waveform generator to repeatedly: a) generate and apply an electrical pulse train to the LES through the electrodes for a stimulation period, and b) terminate the electrical pulse train for a rest period.

In one embodiment, the maintained average pressure does not induce dysphagia in the patient and allows the patient to swallow a bolus during both the stimulation period and rest period.

In one embodiment, the controller is configured to determine parameters of the electrical pulse train that maintain the average pressure of the LES above the pressure level during the rest period.

In one embodiment, the controller is configured to control the waveform generator to stimulate the LES based on a predetermined trigger of at least one of time of day and supine of the patient.

In one embodiment, the controller is configured to adjust a length of the stimulation period and a length of the rest period to maintain the average pressure of the LES above the pressure level.

In one embodiment, the system includes a sensor coupled to the controller for sensing physiological data of the patient, the sensor sensing at least one of pH level at the LES and pressure of the LES, wherein the controller is configured to control the waveform generator based on the sensed physiological data.

In one embodiment, the controller and the waveform generator are enclosed in a common housing and implanted in the patient.

In one embodiment, the system includes an external programming device for configuring the controller to adjust at least one of the energy per stimulation period, duration of the stimulation period, frequency of the stimulation period, and a number of stimulation periods per day based on at least one of the frequency of occurrence or the intensity of acid reflux symptoms in the patient.

In one embodiment, the system includes a disposable battery coupled to the waveform generator and the controller for powering the waveform generator and the controller.

In one embodiment, the controller is configured to control the waveform generator to set a pulse width of the electrical pulse train in a range from 1 µs to 1 second.

In one embodiment, the controller is configured to control the waveform generator to set a frequency of the electrical pulse train in a range from about 1 Hz to about 100 Hz.

In one embodiment, the controller is configured to control the waveform generator to set a current of pulses in the electrical pulse train in a range from 1 µAmp to 50 mAmps.

In one embodiment, the system includes a sensor coupled to the controller for sensing physiological data of a patient; and a memory coupled to the controller for storing the sensed data of the patient, wherein the controller is configured to control the waveform generator to adjust parameters of the electrical pulse train applied to the LES based on an analysis of the stored data.

In one embodiment, the system includes at least one of an accelerometer and inclinometer coupled to the controller for sensing posture data of the patient, wherein the controller is configured to control the waveform generator to adjust parameters of the electrical pulse train applied to the LES based on an analysis of the posture data.

In one embodiment, the system includes an antenna coupled to the controller for wirelessly receiving instructions for instructing the controller to adjust parameters of the electrical pulse train applied to the LES, wherein the instructions are set by at least one of the patient and a trained professional.

In one embodiment, the controller is configured to perform a diagnostic test on the patient by controlling the waveform generator to adjust an amount of electrical energy stimulating the LES over a treatment period based on at least one of the frequency of occurrence or the intensity of acid reflux symptoms in the patient.

In one embodiment, a system is included for increasing pressure of a patient's lower esophageal sphincter (LES), comprising: at least one electrode contacting the LES; a waveform generator coupled to the electrodes; and a controller configured to control the waveform generator to generate and apply an electrical pulse train to the LES through the electrodes during a stimulation period to produce an increase in the pressure of the LES during a rest period after termination of the electrical pulse train, the pressure of the LES determined to increase during the rest period above a pressure level which reduces at least one of a frequency of occurrence or an intensity of acid reflux symptoms in the patient.

In one embodiment, prior to stimulation, the controller is configured with a length of the stimulation period and an electrical current of the pulse train that increases the LES pressure above the pressure level during the rest period.

In one embodiment, prior to stimulation, the controller is configured to determine a length of the rest period that allows the pressure of the LES to increase above the pressure level and does not allow the pressure of the LES to decrease below the pressure level.

In one embodiment, the controller is configured with parameters of the electrical pulse train that produce a first increase in LES pressure during the stimulation period, and a second increase in LES pressure during the rest period.

In one embodiment, the controller is configured to determine parameters of the electrical pulse train that produce an increase in the LES pressure at a first rate during the stimulation period and at a second rate during the rest period.

In one embodiment, includes is a system for increasing pressure of a patient's lower esophageal sphincter (LES), comprising: at least one electrode contacting the LES; a waveform generator coupled to the electrodes; and a controller configured to control the waveform generator to generate and apply an electrical pulse train to the LES through the electrodes to increase the pressure of the LES, and maintain an average pressure of the LES above a pressure level which reduces at least one of a frequency of occurrence or an intensity of acid reflux symptoms in the patient while allowing the patient to swallow during electrical stimulation.

In one embodiment, the bolus has a volume of greater than 1 cubic centimeter (cc).

In one embodiment, the controller is configured to control the waveform generator so that the increased pressure level of the LES is below a pressure level that prevents the patient from swallowing a bolus.

In one embodiment, the controller is configured to control the waveform generator so that the increased pressure level of the LES is below a pressure level that restricts the opening capacity of patient's LES when swallowing a bolus.

In one embodiment, the controller is configured to control the waveform generator so that the electrical stimulation does not inhibit a patient's esophageal motility.

In one embodiment, included is a system for increasing pressure of a patient lower esophageal sphincter (LES), comprising: at least one electrode contacting the LES; a waveform generator coupled to the electrodes; a battery powering the waveform generator; and a controller configured to control the waveform generator to generate and apply an electrical pulse train to the LES through the electrodes to increase the pressure of the LES, the electrical pulse train being controlled by the controller so that an amount of electrical energy consumed from the battery when stimulating the LES is an energy amount that maintains an average pressure of the LES above a pressure level which reduces at least one of a frequency of occurrence or an intensity of acid reflux symptoms in the patient while maintaining at least a minimum charge on the battery to electrically power the waveform generator for a predetermined time period.

In one embodiment, the controller is configured to determine a stimulation time for stimulating the LES to reduce at least one of the frequency of occurrence or the intensity of acid reflux symptoms in the patient, and electrically power the waveform generator for the predetermined time period.

In one embodiment, the controller is configured to determine at least one of a pulse width, electrical current, frequency and energy of the electrical pulse train to reduce at least one of the frequency of occurrence or the intensity of acid reflux symptoms in the patient, and electrically power the waveform generator for the predetermined time period.

In one embodiment, the controller is configured to consume between 30 nano-amp hours and 3 micro-amp-hours of energy during a stimulation period to reduce the acid reflux symptoms in the patient for at least one hour, and does not consume more than 3 micro-amp hours of energy per stimulation period.

In one embodiment, the controller is configured to cumulatively consume between 300 nano-amp hours and 30 micro-amp-hours of energy over a plurality of stimulation periods to reduce the acid reflux symptoms in the patient for at least 24 hours, and does not consume more than 30 micro-amp hours of energy per day.

In one embodiment, the system includes a macrostimulator comprising at least one electrode, an energy source, and a pulse generator in electrical communication with the at least one electrode and energy source, wherein said pulse generator is programmed, adapted to be implanted in a patient and configured to stimulate the patient's LES.

In one embodiment, the system includes a macrostimulator implanted in a patient comprising at least one electrode, an energy source, and a pulse generator in electrical communication with the at least one electrode and energy source, wherein said pulse generator is configured to stimulate the patient's LES and wherein electrical stimulation is initiated, terminated or otherwise modified based upon sensed data.

In one embodiment, the system includes a macrostimulator comprising at least one electrode, an energy source, and a pulse generator in electrical communication with the at least one electrode and energy source, wherein said pulse generator is programmed to stimulate the patient's LES and wherein electrical stimulation is initiated, terminated or otherwise modified based upon sensed data.

In one embodiment, the system includes a macrostimulator implanted in a patient comprising at least one electrode, an energy source, and a pulse generator in electrical communication with the at least one electrode and energy source, wherein said pulse generator is adapted to stimulate the patient's LES, and wherein electrical stimulation is initiated, terminated, or otherwise modified based upon sensed data.

In one embodiment, the electrical stimulation by the macrostimulator is initiated or terminated based upon sensed data and wherein the sensed data is at least one of LES pressure, esophageal pH, inclinometer data, temperature, or accelerometer data.

In one embodiment, the macrostimulator comprises at least one electrode, an energy source, and a pulse generator in electrical communication with the at least one electrode and energy source, wherein said pulse generator is configured to stimulate the patient's LES, and wherein electrical stimulation is initiated or terminated based upon sensed data and wherein the sensed data is at least one of LES pressure, esophageal pH, inclinometer data, temperature, or accelerometer data.

In one embodiment, the macrostimulator is implanted in a patient comprises at least one electrode, an energy source, and a pulse generator in electrical communication with the at least one electrode and energy source, wherein said pulse generator is programmed, adapted to, or configured to stimulate the patient's LES, and wherein electrical stimulation is initiated or terminated based upon sensed data and wherein the sensed data is at least one of LES pressure, esophageal pH, inclinometer data, temperature, or accelerometer data.

In one embodiment, included is a system for treating a gastrointestinal condition of a patient, comprising: (a) a pulse generator in electrical communication with at least one electrode; (b) an energy storage component, wherein said pulse generator generates a pulse stream in accordance with a preset period and wherein said system does not include a sensor for sensing a physiological state of a patient.

In one embodiment, included is a system for treating a gastrointestinal condition of a patient, comprising: (a) a pulse generator in electrical communication with at least one electrode; (b) an energy storage component, wherein said pulse generator generates a pulse stream in accordance with a preset period and wherein said preset period is not dependent upon a physiological state of a patient.

In one embodiment, included is a system for treating a gastrointestinal condition of a patient, comprising: (a) a pulse generator in electrical communication with at least one electrode; (b) an energy storage component, wherein said pulse generator generates a pulse stream in accordance with a preset period and wherein said preset period is not lengthened or shortened based upon a feeding state of a patient.

In one embodiment, included is a system for treating a gastrointestinal condition of a patient, comprising: (a) a pulse generator in electrical communication with at least one electrode; (b) an energy storage component, wherein said pulse generator generates a pulse stream for an on period and wherein said on period is between 1 second and 24 hours and wherein said on period is not lengthened or shortened based upon a feeding state of a patient.

In one embodiment, included is an implantable system for treating a gastrointestinal condition of a patient, comprising: (a) a passive stimulator for receiving energy from a source; (b) a pulse generator in communication with said passive stimulator wherein said pulse generator generates a pulse in accordance with a preset period and wherein said system does not include a sensor for sensing a physiological state of a patient.

In one embodiment, included is an implantable system for treating a gastrointestinal condition of a patient, comprising: (a) a passive stimulator for receiving energy from a source; (b) a pulse generator in electrical communication with said passive stimulator wherein said pulse generator generates a pulse in accordance with a preset period and wherein said system does not include an implantable energy storage component.

In one embodiment, included is an implantable system for treating a gastrointestinal condition of a patient, comprising: (a) a passive stimulator for receiving energy from a source; (b) a pulse generator in electrical communication with said passive stimulator wherein said pulse generator generates a pulse in accordance with a preset period and wherein said preset period is not dependent upon a physiological state of a patient.

In one embodiment, included is an implantable system for treating a gastrointestinal condition of a patient, comprising: (a) a passive stimulator for receiving energy from a source; (b) a pulse generator in electrical communication with said passive stimulator wherein said pulse generator generates a pulse in accordance with a preset period and wherein said preset period is not lengthened or shortened based upon a feeding state of a patient.

In one embodiment, included is an implantable system for treating a gastrointestinal condition of a patient, comprising: (a) a passive stimulator for receiving energy from a source; (b) a pulse generator in electrical communication with said passive stimulator wherein said pulse generator generates a pulse in accordance with an on period and wherein said on period is between 1 second and 24 hours and wherein said on period is not lengthened or shortened based upon a feeding state of a patient.

In one embodiment, included is a system for treating a gastrointestinal condition of a patient, comprising: (a) a stimulator adapted to be implanted proximate to or within a LES of the patient; (b) an energy receiver in electrical communication with the stimulator; and (c) an energy transmitter, wherein said energy transmitter is adapted to be external to the patient's body and configured to wirelessly transmit electrical energy to said energy receiver.

In one embodiment, included is a system for treating a gastrointestinal condition of a patient, comprising: (a) a stimulator adapted to be implanted proximate to or within a LES of the patient; (b) an energy receiver in electrical communication with the stimulator; and (c) an energy transmitter, wherein said energy transmitter is adapted to be external to the patient's body and configured to wirelessly transmit electrical energy to said energy receiver and wherein said energy transmitter transmits energy in accordance with a preset period and wherein said system does not include a sensor for sensing a physiological state of a patient.

In one embodiment, included is a system for treating a gastrointestinal condition of a patient, comprising: (a) a stimulator adapted to be implanted proximate to or within a LES of the patient; (b) an energy receiver in electrical communication with the stimulator; and (c) an energy transmitter, wherein said energy transmitter is adapted to be external to the patient's body and configured to wirelessly transmit electrical energy to said energy receiver and wherein said energy transmitter transmits energy in accordance with a preset period and wherein said preset period is not dependent upon a physiological state of a patient.

In one embodiment, included is a system for treating a gastrointestinal condition of a patient, comprising: (a) a stimulator adapted to be implanted proximate to or within a LES of the patient; (b) an energy receiver in electrical communication with the stimulator; and (c) an energy transmitter, wherein said energy transmitter is adapted to be external to the patient's body and configured to wirelessly transmit electrical energy to said energy receiver and wherein said energy transmitter transmits energy in accordance with a preset period and wherein said preset period is not lengthened or shortened based upon a feeding state of a patient.

In one embodiment, included is a system for treating a gastrointestinal condition of a patient, comprising: (a) a stimulator adapted to be implanted proximate to or within a LES of the patient; (b) an energy receiver in electrical communication with the stimulator; and (c) an energy transmitter, wherein said energy transmitter is adapted to be external to the patient's body and configured to wirelessly transmit electrical energy to said energy receiver and wherein said energy transmitter transmits energy in accordance with an on period and wherein said on period is between 1 second and 24 hours and wherein said on period is not lengthened or shortened based upon a feeding state of a patient.

In one embodiment, the energy delivered to the stimulator has a pulse width in a range of 1 μsec to 1 second.

In one embodiment, the energy delivered to the stimulator has a pulse frequency in a range of 1 Hz to 100 Hz.

In one embodiment, the energy delivered to the stimulator has a pulse amplitude in a range of 1 μAmp to 50 mAmp.

In one embodiment, the energy delivered to the stimulator has a pulse amplitude in a range of 1 μAmp to 50 mAmp.

In one embodiment, after cessation of stimulation, the LES has a normal physiological behavior.

In one embodiment, included is a system for stimulating an anatomical structure within a patient, comprising: (a) a stimulator adapted to be implanted into the patient; and (b) a sensor adapted to be temporarily positioned within a lumen of the patient separate from said stimulator, wherein said sensor is configured to sense a physiological parameter of the patient and communicate data indicative of said physiological parameter to the stimulator and wherein said stimulator modifies at least one stimulation parameter based upon said data.

In one embodiment, included is a system for collecting data from within a patient and transmitting the data outside the patient's body, comprising: (a) a logging device adapted to be implanted into the patient, wherein the logging device comprises a memory adapted to store a plurality of data; and (b) a sensor adapted to be temporarily implanted into a lumen of the patient separate from said logging device, wherein said sensor is configured to sense a physiological parameter of the patient and communicate said sensed data to the logging device and wherein said logging device is capable of storing the sensed data and wirelessly transmitting sensed data to a receiver located outside the body.

In one embodiment, the stimulator comprises a structure that houses stimulating circuitry, a receiver to receive said data from the sensor, and a control unit that analyzes the received data and adjusts said at least one stimulation parameter.

In one embodiment, the stimulating circuitry comprises a power source and means for delivering stimulation.

In one embodiment, the means for delivering stimulation includes at least one of an electrical lead or electrical contact.

In one embodiment, the sensor is adapted to be temporarily located in the body for a duration less than one month In one embodiment, the sensor is a pH capsule.

In one embodiment, the sensor is adapted to measure physiological pH and transmit pH data from within a lumen of the patient's esophagus.

In one embodiment, the sensor comprises a pH sensor located within a nasogastric tube.

In one embodiment, the sensor transmits pH data to the stimulator via uni-directional or bi-directional communications.

In one embodiment, the stimulator comprises a controller that is adapted to execute a plurality of programmatic instructions to adjust said at least one stimulation parameter based upon said data, wherein said data is pH data.

In one embodiment, the pH data is continuously streamed to the stimulator from a pH capsule.

In one embodiment, the controller adjusts one or more stimulation parameters to increase a stimulation dose to the patient if, within a predefined period, the pH data is less than a first threshold value for a percentage of time higher than a second threshold value.

In one embodiment, the first threshold is 4.

In one embodiment, the second threshold is 5 percent.

In one embodiment, the stimulation parameters include at least one of number of stimulation events or size of each stimulation event.

In one embodiment, the at least one of said stimulation parameters is bounded by a maximum value.

In one embodiment, the at least one of said stimulation parameters is bounded by a minimum value.

In one embodiment, the controller adjusts one or more stimulation parameters to decrease a stimulation dose to the patient if, within a predefined period, the pH data is less than a first threshold value for a percentage of time less than a second threshold value.

In one embodiment, the first threshold is 4.

In one embodiment, the second threshold is 1 percent.

In one embodiment, the stimulation parameters include at least one of number of stimulation events or size of each stimulation event.

In one embodiment, the at least one of said stimulation parameters is bounded by a maximum value.

In one embodiment, the at least one of said stimulation parameters is bounded by a minimum value.

In one embodiment, the stimulator comprises a controller that is adapted to execute a plurality of programmatic instructions to adjust said at least one stimulation parameter based upon said data, wherein said data comprises at least one of pH data, accelerometer data, inclinometer data, impedance data or a combination thereof.

In one embodiment, the data is transmitted from the stimulator to a device which is located external to the patient.

In one embodiment, the transmission occurs automatically when the patient and external device are within a predefined proximity.

In one embodiment, the transmission is enabled when the patient and external device are within a predefined proximity and only occurs when expressly authorized by the patient.

In one embodiment, the external device is adapted to receive data indicative of stimulation parameters from a second external device and communicate said data indicative of stimulation parameters to the stimulator within the patient.

In one embodiment, the stimulator comprises a controller that is adapted to monitor a status of said sensor.

In one embodiment, if said sensor fails to respond to communicate attempts from said controller or fails a diagnostic test, the controller generates a signal indicative of a sensor failure state.

In one embodiment, if said controller receives data indicating the sensor has migrated from a desired position to an undesired position, the controller generates a signal indicative of a sensor failure state.

In one embodiment, the data indicating the sensor has migrated from a desired position to an undesired position includes pH less than a threshold value for greater than a predefined a period of time.

In one embodiment, the stimulator comprises a structure that houses stimulating circuitry, a receiving antenna to receive said data from the sensor, and a control unit that analyzes the received data and adjusts said at least one stimulation parameter.

In one embodiment, the receiving antenna can be additionally used to enable energy transfer to said stimulator.

In one embodiment, the said sensor comprises a local energy source and is adapted to transfer energy from said sensor to the stimulator.

In one embodiment, the sensor is a pH capsule or is anchored in a nasogastric tube.

In one embodiment, includes is a method of treating a patient with acid reflux symptoms, wherein said patient has a lower esophageal sphincter (LES) and wherein said LES has a pressure, the method comprising: maintaining an average pressure of the LES above a pressure level which reduces at least one of a frequency of occurrence or an intensity of the acid reflux symptoms both during and after stimulation by applying an electrical pulse train to the LES through electrodes for a stimulation period to increase the pressure of the LES above the pressure level, and terminating the electrical pulse train for a rest period.

In one embodiment, the LES is repeatedly stimulated to maintain the average pressure of the LES in a pressure range which is above a first pressure level to at least one of the frequency of occurrence or the intensity of the acid reflux symptoms in the patient and below a second pressure level to allow the patient to swallow during both the stimulation period and rest period.

In one embodiment, a controller determines parameters of the electrical pulse train that maintain the average pressure of the LES above the pressure level during the rest period.

In one embodiment, the controller controls a waveform generator to stimulate the LES when the pressure of the LES decreases to a third pressure level during the rest period.

In one embodiment, the controller adjusts a length of the stimulation period and a length of the rest period to maintain the average pressure of the LES above the pressure level.

In one embodiment, the controller is configured to control the waveform generator to set a pulse width of the electrical pulse train in a range from about 1 μs to about 1 second.

In one embodiment, the controller is configured to control the waveform generator to set a frequency of the electrical pulse train in a range from about 1 Hz to about 100 Hz.

In one embodiment, the controller is configured to control the waveform generator to set a current of pulses in the electrical pulse train in a range from about 1 μAmp to about 50 mAmps.

In one embodiment, the controller is configured to perform a diagnostic test on the patient by controlling the waveform generator to vary parameters of the electrical pulse train to determine a pressure response of the LES based on different electrical stimulation.

In one embodiment, achieving said pressure level occurs after a minimum period selected from the group consisting of at least 5 minutes, 10 minutes, 15 minutes, 30 minutes, 1 hour, 2 hours, 3 hours, 12 hours, 24 hours, or any time increment therein.

In one embodiment, the said electrical stimulation is initiated prior to a predetermined time; said predetermined time is associated with an acid reflux triggering event; and said initiation occurs prior to said predetermined time by a minimum period selected from the group consisting of at least 5 minutes, 10 minutes, 15 minutes, 30 minutes, 1 hour, 2 hours, 3 hours, 12 hours, 24 hours, or any time increment therein.

In one embodiment, programming said stimulation device, wherein said programming is dependent upon a plurality of stimulation parameters that determine the application of electrical stimulation to the patient LES, and wherein said stimulation parameters are selected, at least in part, to treat acid reflux without inhibiting patient swallowing.

In one embodiment, the electrical stimulation is applied to the patient LES while the patient swallows, during periods of esophageal motility, or during esophageal peristalsis.

In one embodiment, the electrical stimulation is applied to the patient LES in accordance with a preset period and wherein said preset period is not dependent upon a physiological state of a patient.

In one embodiment, the electrical stimulation is applied to the patient LES in accordance with a preset period and wherein said preset period is not dependent upon the patient swallowing, esophageal motility, esophageal peristalsis, or being in a feeding state.

In one embodiment, the electrical stimulation is applied to the patient LES that is not dependent upon a physiological state of the patient.

In one embodiment, electrical stimulation is applied to the patient LES that is not dependent upon a sensed physiological state of the patient.

In one embodiment, electrical stimulation is applied to the patient LES that is not dependent upon the patient swallowing, esophageal motility, esophageal peristalsis, or being in a feeding state.

In one embodiment, sufficient electrical stimulation is applied to the patient LES to increase said pressure but not to inhibit patient swallowing, esophageal motility, or esophageal peristalsis.

In one embodiment, electrical stimulation is applied to the patient LES causing an increase in said pressure of at least 5% only after an elapsed period of time of at least one minute.

In one embodiment, the electrical stimulation normalizes lower esophageal function, normalizes LES pressure, or increases LES pressure to a normal physiological range only after an elapsed period of time of at least one minute.

In one embodiment, the stimulation causes a non-instantaneous or delayed increase in said pressure.

In one embodiment, the electrical stimulation causes a delayed increase in said pressure and wherein said delayed increase in the pressure normalizes LES function, normalizes LES pressure, increases LES pressure to a normal physiological range, or increases LES pressure by at least 3%.

In one embodiment, the electrical stimulation causes an increase in said pressure after said electrical stimulation is terminated.

In one embodiment, the electrical stimulation has a first level, wherein said stimulation causes an increase in said pressure after said electrical stimulation is decreased from said first level.

In one embodiment, the electrical stimulation is applied in accordance with at least one on period, wherein said on period is between 1 second and 24 hours and is not triggered by, substantially concurrent to, or substantially simultaneous with an incidence of acid reflux, and at least one off period, wherein said off period is greater than 10 seconds.

In one embodiment, the electrical stimulation is applied having a current from a single electrode pair ranging from about 1 mAmp to about 8 mAmp.

In one embodiment, the electrical stimulation has a pulse duration within a range of 5 μsec to 1 second.

In one embodiment, the electrical stimulation has a pulse duration of approximately 1 msec.

In one embodiment, the electrical stimulation has a pulse duration of approximately 200 μsec.

In one embodiment, the device incorporates an accelerometer or inclinometer to measure patient positional activity; and applying electrical stimulation based upon one or more of the following parameters as measured by said accelerometer or inclinometer: time spent in the supine position or level of inclination.

In one embodiment, includes is a method of treating a patient with acid reflux symptoms, the method comprising: (a) implanting a stimulation device in the patient to contact the patient LES,(b) applying electrical stimulation to the patient LES, and (b) maintaining an average pressure of the LES above a pressure level both during and after electrical stimulation for a stimulation period to increase the pressure of the LES above the pressure level, and terminating the electrical stimulation for a rest period.

In one embodiment, achieving said pressure level occurs after a minimum period selected from the group consisting of at least 5 minutes, 10 minutes, 15 minutes, 30 minutes, 1 hour, 2 hours, 3 hours, 12 hours, 24 hours, or any time increment therein.

In one embodiment, the electrical stimulation is initiated prior to a predetermined time; said predetermined time is associated with an acid reflux triggering event; and said initiation occurs prior to said predetermined time by a minimum period selected from the group consisting of at least 5 minutes, 10 minutes, 15 minutes, 30 minutes, 1 hour, 2 hours, 3 hours, 12 hours, 24 hours, or any time increment therein.

In one embodiment, including programming said stimulation device, wherein said programming is dependent upon a plurality of stimulation parameters that determine the application of electrical stimulation to the patient LES, and wherein said stimulation parameters are selected, at least in part, to treat acid reflux symptoms without inhibiting patient swallowing.

In one embodiment, electrical stimulation is applied to the patient LES while the patient swallows, during periods of esophageal motility, or during esophageal peristalsis.

In one embodiment, electrical stimulation is applied to the patient LES in accordance with a preset period and wherein said preset period is not dependent upon a physiological state of a patient.

In one embodiment, electrical stimulation is applied to the patient LES in accordance with a preset period and wherein said preset period is not dependent upon the patient swallowing, esophageal motility, esophageal peristalsis, or being in a feeding state.

In one embodiment, electrical stimulation is applied to the patient LES that is not dependent upon a physiological state of the patient.

In one embodiment, electrical stimulation is applied to the patient LES that is not dependent upon a sensed physiological state of the patient.

In one embodiment, electrical stimulation is applied to the patient LES that is not dependent upon the patient swallowing, esophageal motility, esophageal peristalsis, or being in a feeding state.

In one embodiment, sufficient electrical stimulation is applied to the patient LES to increase said pressure but not to inhibit patient swallowing, esophageal motility, or esophageal peristalsis.

In one embodiment, electrical stimulation is applied to the patient LES causing an increase in said pressure of at least 5% only after an elapsed period of time of at least one minute.

In one embodiment, the electrical stimulation normalizes lower esophageal function, normalizes LES pressure, or increases LES pressure to a normal physiological range only after an elapsed period of time of at least one minute.

In one embodiment, the stimulation causes a non-instantaneous or delayed increase in said pressure.

In one embodiment, the electrical stimulation causes a delayed increase in said pressure and wherein said delayed increase in the pressure normalizes LES function, normalizes LES pressure, increases LES pressure to a normal physiological range, or increases LES pressure by at least 3%.

In one embodiment, the electrical stimulation causes an increase in said pressure after said electrical stimulation is terminated.

In one embodiment, the electrical stimulation has a first level, wherein said stimulation causes an increase in said pressure after said electrical stimulation is decreased from said first level.

In one embodiment, the electrical stimulation is applied in accordance with at least one on period, wherein said on period is between 1 second and 24 hours and is not triggered by, substantially concurrent to, or substantially simultaneous with an incidence of acid reflux, and at least one off period, wherein said off period is greater than 10 seconds.

In one embodiment, the electrical stimulation is applied having a current from a single electrode pair ranging from about 1 mAmp to about 8 mAmp.

In one embodiment, the electrical stimulation has a pulse duration within a range of 5 μsec to 1 second.

In one embodiment, the electrical stimulation has a pulse duration of approximately 1 msec.

In one embodiment, the electrical stimulation has a pulse duration of approximately 200 μsec.

In one embodiment, the device incorporates an accelerometer or inclinometer to measure patient positional activity; and applying electrical stimulation based upon one or more of the following parameters as measured by said accelerometer or inclinometer: time spent in the supine position or level of inclination.

In one embodiment, includes is a method of treating a patient with acid reflux symptoms, the method comprising: (a) implanting the stimulation device in the patient to contact the patient LES; (b) applying electrical stimulation to the patient LES; (b) measuring one or more parameters selected from the group consisting of patient feed state including type of feed; patient position; patient activity; patient reflux profile; LES pressure; LES electrical activity; LES mechanical activity gastric pressure; gastric electrical activity; gastric chemical activity; gastric temperature; gastric mechanical activity; patient intuition; vagal neural activity; and, splanchnic neural activity; (c) inputting the collected data into an algorithm; and (d) applying electrical stimulation based upon a summary score calculated by said algorithm to maintain an average pressure of the LES above a pressure level both during and after electrical stimulation for a stimulation period to increase the pressure of the LES above the pressure level, and terminating the electrical stimulation for a rest period.

In one embodiment, included is a method of programming a stimulator wherein said stimulator is implanted proximate to a lower esophageal sphincter of a patient, comprising the steps of: (a) causing said stimulator to stimulate the lower esophageal sphincter; (b) monitoring a pressure level of said lower esophageal sphincter while said stimulator is stimulating the lower esophageal sphincter; (c) recording a time when the pressure level of said lower esophageal sphincter exceeds a first threshold value; (d) terminating said stimulation when the pressure level of said lower esophageal sphincter exceeds a first pressure value; (e) monitoring the pressure level of said lower esophageal sphincter after terminating said stimulation; (f) recording a time when the pressure level of said lower esophageal sphincter reaches a second pressure value; and (g) programming the stimulator to operate for a fixed, preset period of time.

In one embodiment, included is a method of programming a stimulator wherein said stimulator is implanted proximate to a lower esophageal sphincter of a patient, comprising the steps of: (a) causing said stimulator to stimulate the lower esophageal sphincter; (b) recording a time and an electrode impedance value when said stimulation is started; (c) monitoring a pressure level of said lower esophageal sphincter while said stimulation is being applied; (d) recording a time when the pressure level of said lower esophageal sphincter exceeds a first threshold value; (e) recording an electrode impedance value when the pressure level of said lower esophageal sphincter exceeds the first threshold value; (f) terminating said energy input to said stimulator when the pressure level of said lower esophageal sphincter exceeds a first pressure value; (g) monitoring the pressure level of said lower esophageal sphincter after terminating said stimulation; (h) recording a time when the pressure level of said lower esophageal sphincter reaches a second pressure value; (i) recording an electrode impedance value when the pressure level of said lower esophageal sphincter reaches the second pressure value;

In one embodiment, included is a method of programming a stimulator wherein said stimulator is implanted proximate to a lower esophageal sphincter of a patient, comprising the steps of: (a) applying an energy input to said stimulator to cause said stimulator to stimulate the lower esophageal sphincter; (b) recording a time and a electrode impedance value when said energy input is first applied to said stimulator; (c) monitoring a pressure level of said lower esophageal sphincter while said energy input is being applied to said stimulator; (d) recording a time when the pressure level of said lower esophageal sphincter exceeds a first threshold value; (e) recording a electrode impedance value when the pressure level of said lower esophageal sphincter exceeds the first threshold value; (f) terminating said energy input to said stimulator when the pressure level of said lower esophageal sphincter exceeds a first pressure value; (g) monitoring the pressure level of said lower esophageal sphincter after terminating said energy input to said stimulator; (h) recording a time when the pressure level of said lower esophageal sphincter reaches a second pressure value; (i) recording a electrode impedance value when the pressure level of said lower esophageal sphincter reaches the second pressure value; (j) programming the stimulator to operate for a fixed, preset period of time.

In one embodiment, the fixed, preset period of time is between 1 minutes and 12 hours.

In one embodiment, the fixed, preset period of time is not dependent on a feeding state of the patient.

In one embodiment, the fixed, preset period of time is not dependent on whether the patient is engaging in a swallow.

In one embodiment, the recording and monitoring steps are performed automatically by a system in data communication with a manometry measurement system.

In one embodiment, the energy input has a pulse frequency of approximately 20 Hz, a pulse duration of approximately 200 μsec, and a pulse amplitude in a range of 0.1 mAmp to 15 mAmp.

In one embodiment, the first pressure value is at least 20 mmHg.

In one embodiment, the second pressure value is at most 10 mmHg.

In one embodiment, the second pressure value is proportional to a baseline pressure level of the patient's lower esophageal sphincter.

These and other embodiments shall be discussed in greater detail below and in relation to the accompanying figures.

BRIEF DESCRIPTION OF THE DRAWINGS

These and other objects and advantages of the presently disclosed treatment methodologies, devices, and systems will become more fully apparent from the following detailed description when read in conjunction with the accompanying drawings with like reference numerals indicating corresponding parts through-out, wherein.

DETAILED DESCRIPTION OF THE INVENTION

Figure 1:
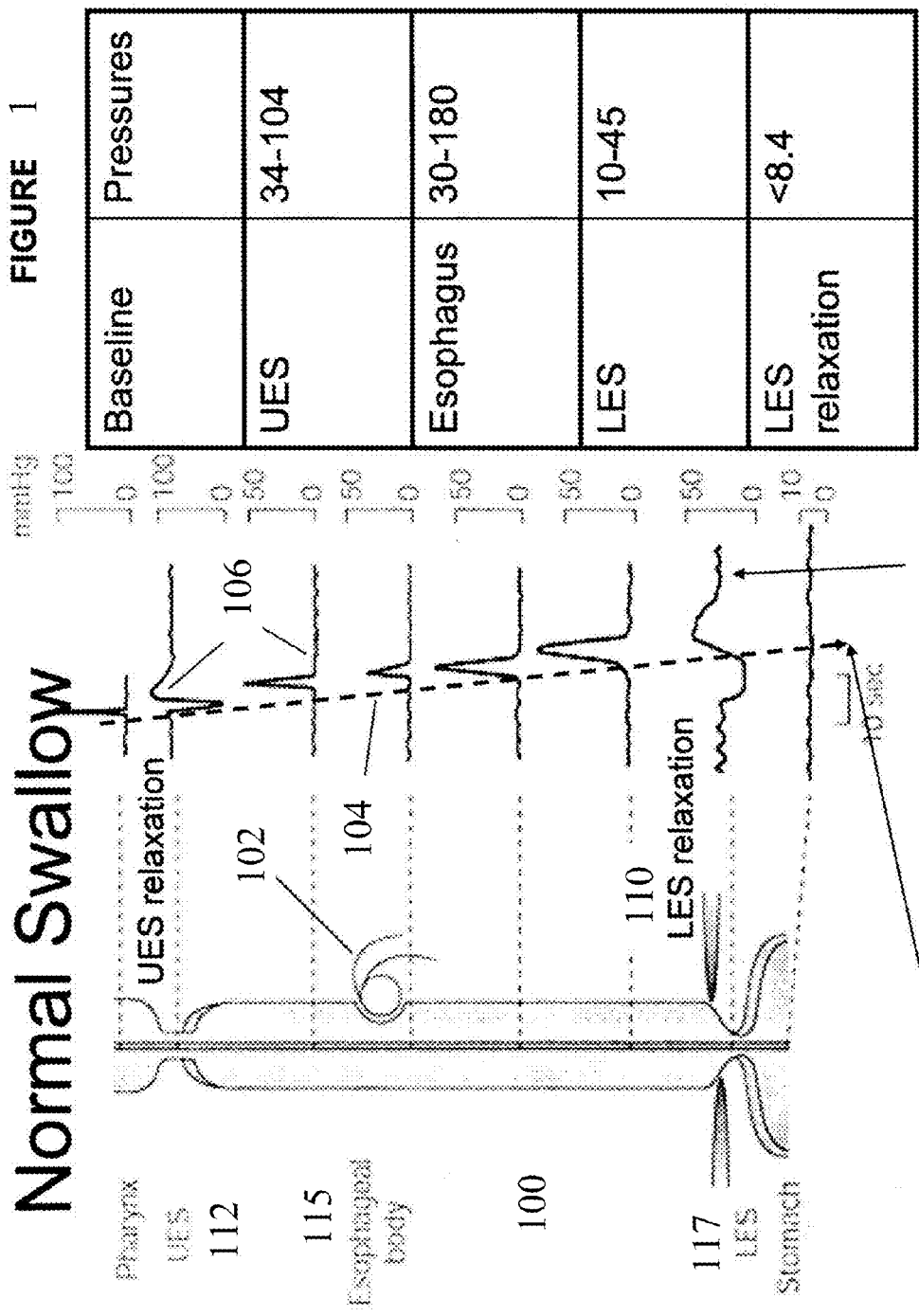
FIG. 1 depicts the physiology of a normal swallow.

The present invention is directed toward programmable implantable electro-medical device for the treatment of gastro-esophageal reflux disease (GERD). The electro-medical device of the present invention employs stimulators, including macrostimulators or microstimulators, which can be implanted with minimal invasiveness in the gastrointestinal system. Specifically, these devices can be beneficial for deep implant locations for which there is a natural orifice access providing closer proximity than from outside the body. It should further be appreciated that the present device is capable of stimulating all smooth muscle, not limited to GI smooth muscles and that the present device can be used to deliver stimulation to the proximal stomach or area adjacent to the proximal stomach for treating various diseases that can be affected by gastric stimulation such as gastric motility problems and diabetes. The present application further incorporates by reference U.S. Pat. No. 6,901,295, PCT/US08/56479, and U.S. patent application Ser. Nos. 12/030,222, 11/539,645, and 12/359,317 in their entirety.

The systems and methods disclosed herein can be used to achieve a plurality of different therapeutic objectives: treatment of GERD; normalizing a patient's LES function; treatment of hypotensive LES; increase resting or baseline LES pressure; treating a patient to normalize esophageal pH, wherein said normalization is achieved when a patient has an esophageal pH value of less than 4 for a period of time no greater than 5%, 10%, or 15% of a 24 hour period or some fraction thereof; treating a patient to normalize esophageal pH when in the supine position, wherein said normalization is achieved when a patient has an esophageal pH value of less than 4 for a period of time no greater than 3% of a 24 hour period; treating a patient to prevent damage to the patient's lower esophageal sphincter caused by acid reflux; treatment of supine position induced GERD; treatment of activity-induced GERD; prevention of supine position induced GERD; prevention of activity-induced GERD; treating a patient to mitigate damage to the patient's lower esophageal sphincter caused by acid reflux; treating a patient to stop progression of damage to the patient's lower esophageal sphincter caused by acid reflux; treating a patient to minimize transient relaxations of the patient's lower esophageal sphincter; modifying or increasing LES pressure; modifying or increasing esophageal body pressure; modifying or improving esophageal body function; modifying or improving esophageal sensation induced by the refluxate; modifying or improving the volume of refluxate; modifying or improving the clearance of the refluxate; reducing incidents of heartburn; modifying or improving esophageal acid exposure; increasing lower esophageal tone; detecting when a patient swallows; detecting when a patient is eating; treating a gastrointestinal condition of a patient; treating a patient to minimize the patient's consumption of certain solids or liquids; reducing patient symptoms associated with GERD wherein such reduction is measured by an improvement in a patient quality of life survey and wherein said improvement is calculated by having a patient provide a first set of responses to said quality of life survey prior to treatment and having a patient provide a second set of responses to said quality of life survey after said treatment and comparing the first set of responses to said second set of responses; treating a patient for any of the above-listed therapeutic objectives with the additional requirement of avoiding tissue habituation, tissue fatigue, tissue injury or damage, or certain adverse reactions, including, but not limited to, chest pain, difficulty in swallowing, pain associated with swallowing, heartburn, injury to surrounding tissue, or arrhythmias.

The disclosed treatment methods may be practiced within, and devices may be implanted within, a plurality of anatomical regions to achieve one or more of the therapeutic objectives described above. Treatment sites, or implantation sites, include: the lower esophageal sphincter; within 5 cm above and 5 cm below the LES; proximate to the LES; in the vicinity of the LES; the esophageal body; the upper esophageal sphincter (UES); within, proximate to, or in the vicinity of the gastro-esophageal junction; the esophagus, including esophageal body, LES, and UES; proximate to the esophagus; in the vicinity of the esophagus; at or within the stomach; nerves supplying the LES or gastro-esophageal junction; nerves supplying the esophageal body; nerves supplying the UES; or nerves supplying the esophagus, including the esophageal body, LES, and UES.

Additionally, it should be appreciated that a therapy which requires a lower amount of energy increases the long-term functionality of a stimulation device. Furthermore, accurate implantation of electrodes is imperative for improved efficacy and safety of these devices. Submucosa of organ systems, such as the area within the gastrointestinal tract between the muscularis mucosa and muscularis propria (two high impedance layers), have a relatively lower electrode-tissue interface impedance (referred to as impedance herein) and are therefore desirable locations for lead implantation and improved efficacy of stimulation. In addition, the loose connective tissue of the submucosa provides an improved environment for tunneling and creating pockets for lead implantation and microstimulator implantation.

In one embodiment, the macrostimulator, microstimulator or their respective electrodes are implanted in the submucosa proximate to the LES, esophagus, or UES to cause adjacent smooth muscle contraction using electrical field stimulation. Additional stimulator structures and/or electrodes may be placed in the adjacent muscularis or serosa and used in combination with the aforementioned macrostimulator or microstimulator. In another embodiment, the stimulator or electrodes are implanted in the gastrointestinal submucosa to cause gastrointestinal muscle contraction using electrical field stimulation. Additional stimulator structures and/or electrodes may be placed or proximate to in the adjacent gastrointestinal muscularis mucosa, gastrointestinal serosa, or gastrointestinal nerves.

Treatment Methodologies

In one embodiment, any stimulator device, including a macrostimulator or microstimulator, can be programmed to implement one or more treatment protocols disclosed herein. It should be appreciated that the treatment methods described below are implemented in a stimulator, such as a macrostimulator or microstimulator, having a plurality of electrodes, or at least one electrode, including, but not limited to, unipolar or bipolar electrodes, an energy source, such as a battery or capacitor, and a memory, whether local to the stimulator or remote from the stimulator and adapted to transmit data to the stimulator, which stores a plurality of programmatic instructions wherein said instructions, when executed by the macro/microstimulator, execute the stimulation therapies, as described below.

The present application is directed toward stimulation treatment methods that permit a patient, with one or more implanted stimulator systems as described above, to engage in a swallow that causes liquid, food mass, food mass mixed with liquid, or any bolus of matter greater than 1 cc to pass through the patient's esophagus (collectively referred to as a wet swallow or bolus swallow; wet swallow and bolus swallow shall be used interchangeably) while concurrently having one or more gastrointestinal anatomical structures, such as the upper esophagus, upper esophageal sphincter, esophagus, lower esophageal sphincter, the distal esophagus, the gastric cardia, gastric fundus, and/or the vagus nerve, or any of the other anatomical structures described herein, be subjected to electrical stimulation.

The prior art has conventionally taught that stimulation of gastrointestinal structures, particularly the esophagus and lower esophageal sphincter, must cease when a patient engages in a swallow. It has now been unexpectantly determined that, if stimulated appropriately, such stimulation need not cease during, concurrent with, or in response to a patient engaging in a wet swallow. The stimulation protocols, described below, are effectuated through the stimulation devices described herein and by the patent documents incorporated herein by reference. Such devices generally include any device for electrical stimulation of one or more structures in the esophagus and for use in the treatment of GERD, comprising a pulse generator providing electrical stimulation, a power source for powering the pulse generator, one or more stimulating electrodes operatively coupled or connected to the pulse generator wherein the electrode sets are adapted to be positioned within or adjacent to one or more anatomical structures described herein. Preferably, the stimulating electrodes are designed to be implanted predominantly in the submucosal layer or the muscularis layer of the esophagus. In one embodiment, a plurality of electrodes in electrical communication with a macrostimulator are implanted predominantly in the muscularis propria. In one embodiment, a plurality of electrodes in electrical communication with a microstimulator are implanted predominantly in the submucosal layer, if done endoscopically, and in the muscularis layer if done laparoscopically.

In one embodiment, the stimulation parameters, which are effectuated through an electrical pulse that can be of any shape, including square, rectangular, sinusoidal or saw-tooth, may comprise any of the variable ranges detailed in the table below

TABLE 1

| Pulse Type | Pulse Width | Pulse Frequency | Pulse Amplitude | On Cycle | Off Cycle |
| --- | --- | --- | --- | --- | --- |
| Short Pulse | 1-999 μsec | 1-100 Hz | Low (1-999 μAmp) Intermediate (1-50 mAmp) and any values therein | 0-24 hrs | 0-24 hrs |
| Intermediate Pulse | 1-250 msec | 1-100 Hz | Low (1-999 μAmp) Intermediate (1-50 mAmp) and any values therein | 0-24 hrs | 0-24 hrs |

TABLE 1-continued

| Pulse Type | Pulse Width | Pulse Frequency | Pulse Amplitude | On Cycle | Off Cycle |
|---|---|---|---|---|---|
| Intermediate Pulse | 1-250 msec | 1-59 cpm | Low (1-999 µAmp) Intermediate (1-50 mAmp) and any values therein | 0-24 hrs | 0-24 hrs |
| Long Pulse | 251 msec-1 sec | 1-59 cpm | Low (1-999 µAmp) Intermediate (1-50 mAmp) and any values therein | 0-24 hrs | 0-24 hrs |

In one embodiment, the present invention is directed to a method for treating esophageal disease by electrically stimulating a lower esophageal sphincter or nerve supplying the LES that causes improvement in the lower esophageal sphincter pressure without affecting, preventing, prohibiting, or otherwise hindering a bolus swallow induced relaxation of the lower esophageal sphincter or bolus swallow induced esophageal body motility. In this embodiment, because electrical stimulation need not be inhibited, there is no need to sense for the bolus swallow in order to trigger a cessation of electrical stimulation and, therefore, a stimulator need not be programmed to sense for the bolus swallow, to modify stimulation in response to a bolus swallow (even if the stimulation device has sensing capabilities), or to be otherwise responsive to a bolus swallow.

This stimulation process normalizes lower esophageal sphincter function because it improves lower esophageal sphincter pressure while not prohibiting or preventing a natural bolus swallow. This process also a) does not affect gastric distension induced relaxation of the lower esophageal relaxation, b) improves the post bolus swallow augmentation of the LES pressure, and c) improves the esophageal body function, among other therapeutic benefits, as described above.

Having eliminated the need to dynamically control the electrical stimulation based on swallow sensing, the system can be allowed to engage in automated "on/off" duty cycles that can range from 1 second to 24 hours. During the "on" period, stimulation is preferably applied for a long enough period to enable recruitment of adequate nerves and/or muscle fibers to achieve the desired pressure, function or effect. The desired "on" period is patient specific and is preferably calculated based on the time required to change the LES pressure from baseline pressure or function to the desired therapeutic pressure or function plus additional time to maintain the therapeutic pressure (maintenance time) or function. In one embodiment, the maintenance time ranges from 1 second to 12 hours. While sensors are not required, in one embodiment, the "on" period can be determined, or triggered by, sensors that sense changes in the LES, such as LES pressure changes, or the esophagus. Those sensing electrodes sense one or more of change in gastrointestinal muscle tone or impedance, peristaltic activity, esophageal peristalsis, esophageal pH, esophageal pressure, esophageal impedance, esophageal electrical activity, gastric peristalsis, gastric electrical activity, gastric chemical activity, gastric hormonal activity, gastric temperature, gastric impedance, electrical activity, gastric pH, blood chemical and hormonal activity, vagal or other gastrointestinal neural activity and salivary chemical activity and can be preferably positioned in or adjacent one or more of the esophagus, the stomach, the small intestine, the colon, the vagus or other gastrointestinal nerves and the vascular system.

The "off" period is preferably set in order to prevent development of tolerance or muscle fatigue, to improve device functionality, and to optimize energy consumption from the battery. The desired "off" period ranges from 1 second to 24 hours. The desired "off" period is patient specific and calculated based on the time required to change the LES pressure or function from the desired therapeutic pressure or function to the baseline pressure or function plus optional additional time to maintain the baseline pressure (relaxation time) or function. In one embodiment, the relaxation time ranges from 1 second to 12 hours. While sensors are not required, in one embodiment, the "off" period can be determined, or triggered by, sensors that sense changes in the LES, such as pressure, or the esophagus. Those sensing electrodes sense one or more of change in gastrointestinal muscle tone or impedance, peristaltic activity, esophageal peristalsis, esophageal pH, esophageal pressure, esophageal impedance, esophageal electrical activity, gastric peristalsis, gastric electrical activity, gastric chemical activity, gastric hormonal activity, gastric temperature, gastric impedance, gastric pH, blood chemical and hormonal activity, vagal or other gastrointestinal neural activity and salivary chemical activity and can be preferably positioned in or adjacent one or more of the esophagus, the stomach, the small intestine, the colon, the vagus or other gastrointestinal nerves and the vascular system.

Accordingly, in one embodiment, stimulation can be provided for a first period to generate a LES pressure, function or esophageal function of a first threshold level, then the stimulation can be lowered or removed while still maintaining LES pressure, function or esophageal function at or above the first threshold level of LES pressure, function or esophageal function, thereby treating GERD and other gastrointestinal indications. Stimulation of greater than a first threshold level of LES pressure can be delivered within a time period of less than a first time period, thereby treating certain gastrointestinal indications. In one embodiment, the present specification discloses a treatment method in which stimulation, such as at or under 30 mAmp, 15 mAmp, 10 mAmp, 8 mAmp, or any increment therein, is applied to achieve a LES pressure of less than a first threshold level and, concurrently, wet swallows are still enabled without terminating or decreasing the stimulation. In one embodiment, the present specification discloses a treatment method in which stimulation, such as at or under 30 mAmp, 15 mAmp, 10 mAmp, 8 mAmp, or any increment therein, is applied and then terminated, after which LES pressure function or esophageal function increases beyond a first threshold level and, concurrently, wet swallows are still enabled. It should be appreciated that the stimulation parameters can be presented in terms of total energy applied. For example, the current stimulation parameters can be replaced, throughout this specification, with preferred energy levels, such as at or under 6 mC, 3 mC, 1 mC, 0.08 mC, or any increment therein.

It should further be appreciated that the treatment methodologies disclosed herein adjust for, take advantage of, account for, or otherwise optimally use a delayed, or latent, pressure response from the LES in response to electrical stimulation. Conventionally, the prior art has taught that the LES instantaneously responds, either by contracting or relaxing, to the application of, or removal of, electrical stimulation. In the present treatment methodologies, the LES has a delayed or latent response to electrical stimulation, thereby resulting in a gradual increase in LES pressure after the application of electrical stimulation and a sustained heightened level of LES pressure after electrical stimulation is terminated, at least for certain stimulation parameters. Accordingly, a desired normalization of LES pressure or tone can be achieved well in advance of an expected GERD triggering event, such as eating, sleeping, napping, laying down, being in a supine position, bolus swallowing, or engaging in physical activity, by applying electrical stimulation before the GERD triggering event and then terminating the stimulation prior to, during, or after the GERD triggering event. Multiple embodiments of the present invention take advantage of this delayed response by stimulating the LES in a manner that does not cause immediate contraction of the musculature or an immediate increase in LES pressure. For example, in one embodiment, stimulation is directed to the LES at a level of no more than 6 mC repeated on a regular basis, for example 20 times a second, for a specific period of time, for example 30 minutes. This results in contraction of the LES and a rise in LES pressure that does not occur until after the initial 5 minutes of stimulation and that continues once stimulation has been terminated. In one embodiment, stimulation is directed to the LES at a level of no more than 6 mC repeated on a regular basis, for example 20 times a second, for a specific period of time, for example 30 minutes. This results in contraction of the LES and a rise in LES pressure that does not occur until after the initial stimulation initiated and that continues or persists once stimulation has been terminated.

In these stimulation methodologies, a sub-threshold stimulation that does not generate an instantaneous LES or esophageal function response is applied for a predefined duration of time to achieve a therapeutic response. In one embodiment, a sub-threshold stimulation means that an applied stimulation does not substantially instantaneously achieve a contraction. A sub-threshold stimulation may have stimulation parameters of less than 20 mAmp, less than 10 mAmp, or less than 8 mAmp. In one embodiment, a threshold or above threshold stimulation means that an applied stimulation substantially instantaneously achieves a contraction and may have stimulation parameters of greater than 20 mAmp, greater than 10 mAmp, or greater than 8 mAmp. Sub-threshold stimulation has multiple advantages, including improved device functionality, improved energy transfer in a wireless microstimulator, improved patient safety, decreased patient adverse symptoms or side effects and decreased tolerance and/or fatigue.

Referring to FIG. 1, a normal esophageal pressure profile 100 is shown. With deglutition, the peristaltic wave follows immediately after the UES relaxation, producing a lumen-occluding contraction of the esophageal circular muscle. The contraction wave migrates aborally at a speed that varies along the esophagus. The peristaltic velocity averages about 3 cm/sec in the upper esophagus, then accelerates to about 5 cm/sec in the mid-esophagus, and slows again to approximately 2.5 cm/sec distally. The duration and amplitude of individual pressure waves also varies along the esophagus. The duration of the wave is shortest in the proximal esophagus (approximately 2 seconds) and longest distally (approximately 5 to 7 seconds). Peak pressures average 53±9 mmHg in the upper esophagus, 35±6 mmHg in the mid-portion, and 70±12 mmHg in the lower esophagus. These parameters can be influenced by a number of variables including bolus size, viscosity, patient position (e.g., upright vs. supine), and bolus temperature. For instance, a large bolus elicits stronger peristaltic contractions that migrate distally at a slower rate than a small bolus. The peristaltic velocity is also slowed by outflow obstruction or increases in intra-abdominal pressure. Warm boluses tend to enhance, whereas cold boluses inhibit the amplitude of peristaltic contractions.

Accordingly, bolus 102 propagates through the UES 112, esophageal body 115, and LES 117 over a period of approximately, and typically, ten seconds. As the bolus 102 moves through, portions of the UES 112, esophageal body 115, and LES 117 experience an increase in pressure. In a normal person, the baseline pressure range for the UES 112 is between 34 and 104 mmHg, for the esophagus 115 is between 30 and 180 mmHg, and for the LES 117 is between 10 and 45 mmHg. At the point of LES relaxation 110, which occurs to permit the bolus to pass through into the stomach, the LES pressure decreases to below approximately 8.4 mmHg. Notably, in a normal patient, post-swallow, the LES pressure increases, after having decreased for the swallow, and then remains at a higher baseline pressure level than just immediately prior to the swallow.

In one embodiment, the presently disclosed methods and systems return an abnormally functioning LES to a state of normalcy, post-stimulation or post initiation of stimulation. The treatment methodology comprises implanting a stimulation device, as described herein, and electrically stimulating the device to cause an increased LES pressure, in accordance with any of the stimulation methodologies described herein. After stimulation is terminated, one or more of the following functional parameters, characteristic of an abnormally functioning LES, achieves normal physiological range: a) LES basal pressure (respiratory minima) returns to a range of 15-32 mmHg, b) LES basal pressure (respiratory mean) returns to a range of 10-43 mmHg, c) LES residual pressure returns to a range of less than 15 mmHg, d) LES percent relaxation returns to a range of greater than 40%, e) LES duration of contraction returns to a range of 2.9 seconds to 5.1 seconds (3 cm above the LES), 3 seconds to 5 seconds (8 cm above the LES), or 2.8 seconds to 4.2 seconds (13 cm above the LES), f) lower esophageal acid exposure during 24-hour pH-metry returns to a range of pH<4 for less than 10%, and preferably less than 5%, of total or less than 8% or preferably less than 3% of supine time, and/or g) esophageal reflux events return to less than 100 per 24 hour period or reduce by 50% as documented by impedance pH monitoring, i) normal bolus swallows return with complete bolus transit, defined as detection of bolus exit in all 3 of the distal impedance channels and/or j) esophageal pH returns to a range equal to twice the normal, as defined in the table below or any normative standards for the measuring device.

TABLE 2

Catheter-based dual-probe (distal and proximal) esophageal pH monitoring

| Variable | Normal | |
| --- | --- | --- |
| | Proximal (%) | Distal (%) |
| Time pH <4.0 (%) | | |
| Total period | <0.9 | <4.2 |
| Upright period | <1.2 | <6.3 |
| Recumbent period | <0.0 | <1.2 |

Distal = 5 cm above manometric defined proximal border of the LES.
Proximal = 20 cm above manometric defined proximal border of the LES.

TABLE 2-continued

Catheter free distal esophageal pH monitoring

| Variable | Normal Distal (%) |
|---|---|
| Time pH <4.0 (%) | |
| Total period | <5.3 |
| Upright period | <6.9 |
| Recumbent period | <6.7 |

Distal = 6 cm above endoscopic defined gastroesophageal junction

Accordingly, the presently disclosed methods and systems modify one or more of the aforementioned functional parameters characteristic of an abnormally functioning LES or the esophagus to that of a normally or improved functioning LES or the esophagus, even after stimulation is terminated. By transforming an abnormally functioning LES or the esophagus to a normally or improved functioning LES or the esophagus, esophageal reflux, GERD, esophageal motility disorders or esophageal neural, muscular or neuromuscular disorders, can be effectively treated.

In another embodiment, the presently disclosed methods and systems modify an abnormally functioning LES or the esophagus to provide for an adequately functioning LES or the esophagus post-stimulation. The treatment methodology comprises implanting a stimulation device, as described herein, and electrically stimulating the tissue to cause an increase in LES pressure, in accordance with any of the stimulation methodologies described herein. After stimulation is terminated, one or more of the following functional parameters, characteristic of an abnormally functioning LES, returns to a physiological range sufficient to prevent esophageal reflux, GERD, esophageal motility disorders or esophageal neural, muscular or neuromuscular disorders: a) LES basal pressure, b) LES residual pressure, c) LES percent relaxation, d) LES duration of contraction, e) distal esophageal pH, f) esophageal reflux events, and g) esophageal body function. Accordingly, the present invention modifies physiological parameters characteristic of an abnormally functioning LES, relative to the patient's pre-treatment state, to that of an adequately functioning LES, even after stimulation is terminated. By transforming an abnormally functioning LES to an adequately functioning LES, esophageal reflux, GERD, esophageal motility disorders or esophageal neural, muscular or neuromuscular disorders can be effectively mitigated.

In another embodiment, the present invention improves the LES pressure profile of an abnormally functioning LES post-stimulation. The treatment methodology comprises implanting a stimulation device, as described herein, and electrically stimulating the tissue to cause an increase in LES pressure, in accordance with any of the stimulation methodologies described herein. After stimulation is terminated, LES basal pressure is improved, relative to the patient's pre-treatment state, by at least 5%, preferably 10%. Accordingly, the presently disclosed methods and systems modify the pressure profile of an abnormal functioning LES, even after stimulation is terminated. By doing so, esophageal reflux, GERD, esophageal motility disorders or esophageal neural, muscular or neuromuscular disorders can be effectively mitigated.

In another embodiment, the presently disclosed methods and systems improve, post-stimulation, at least one of a) esophageal body pressure, b) esophageal body contractility, c) esophageal body motility, d) esophageal body bolus transit, or e) esophageal body peristalsis, resulting in improved esophageal acid clearance after a reflux event, decreasing esophageal acid exposure time, and minimizing damage from exposure of esophageal mucosa to gastro-duodenal refluxate. The treatment methodology comprises implanting a stimulation device, as described herein, and electrically stimulating the tissue to cause an increase in LES pressure, in accordance with any of the stimulation methodologies described herein. After stimulation is terminated, at least one of a) esophageal body pressure, b) esophageal body contractility, c) esophageal body motility, e) esophageal body bolus transit, or f) esophageal body peristalsis improves and remains in an improved state while the stimulator is off.

In another embodiment, the presently disclosed methods and devices achieve any of the aforementioned therapeutic objectives by providing or implanting a stimulation device adapted to be implanted within the patient's lower esophageal sphincter, wherein the patient's esophagus has a function, and treating the patient by applying electrical stimulation, wherein the stimulation causes an improvement in esophageal function. Esophageal function may include any one of esophageal pressure, bolus transit, esophageal perception, esophageal accommodation or esophageal clearance of the refluxate.

In another embodiment, the presently disclosed methods and devices achieve any of the aforementioned therapeutic objectives by providing or implanting a stimulation device adapted to be implanted within the patient's lower esophageal sphincter, wherein the patient's esophagus has a function, and treating the patient by applying electrical stimulation, wherein the stimulation causes a non-instantaneous or delayed improvement in esophageal function. Esophageal function may include any one of esophageal pressure, bolus transit, esophageal perception, esophageal accommodation or esophageal clearance of the refluxate.

Figure 2:
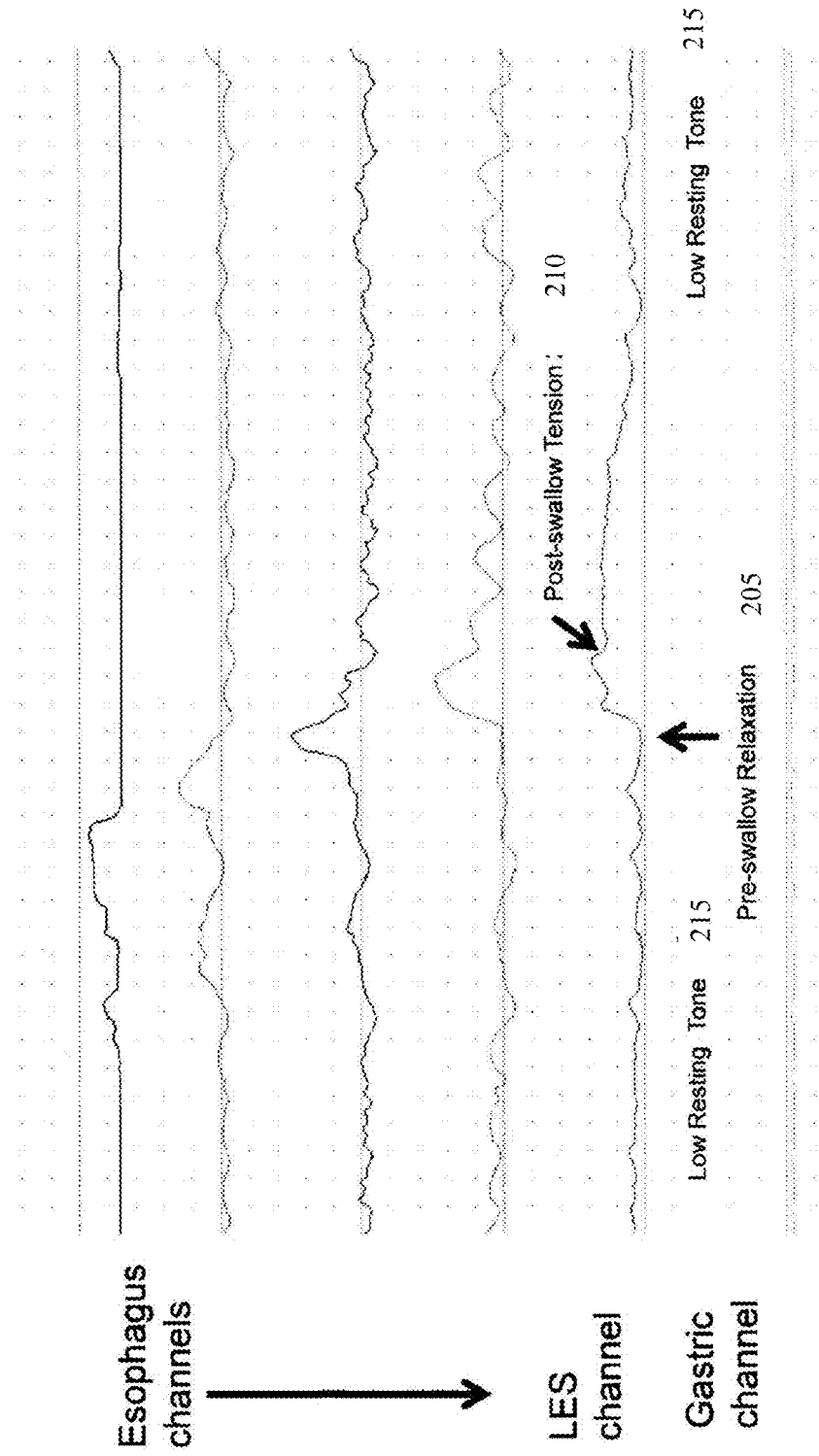
FIG. 2 depicts a wet swallow at baseline for a GERD patient.
Figure 3:
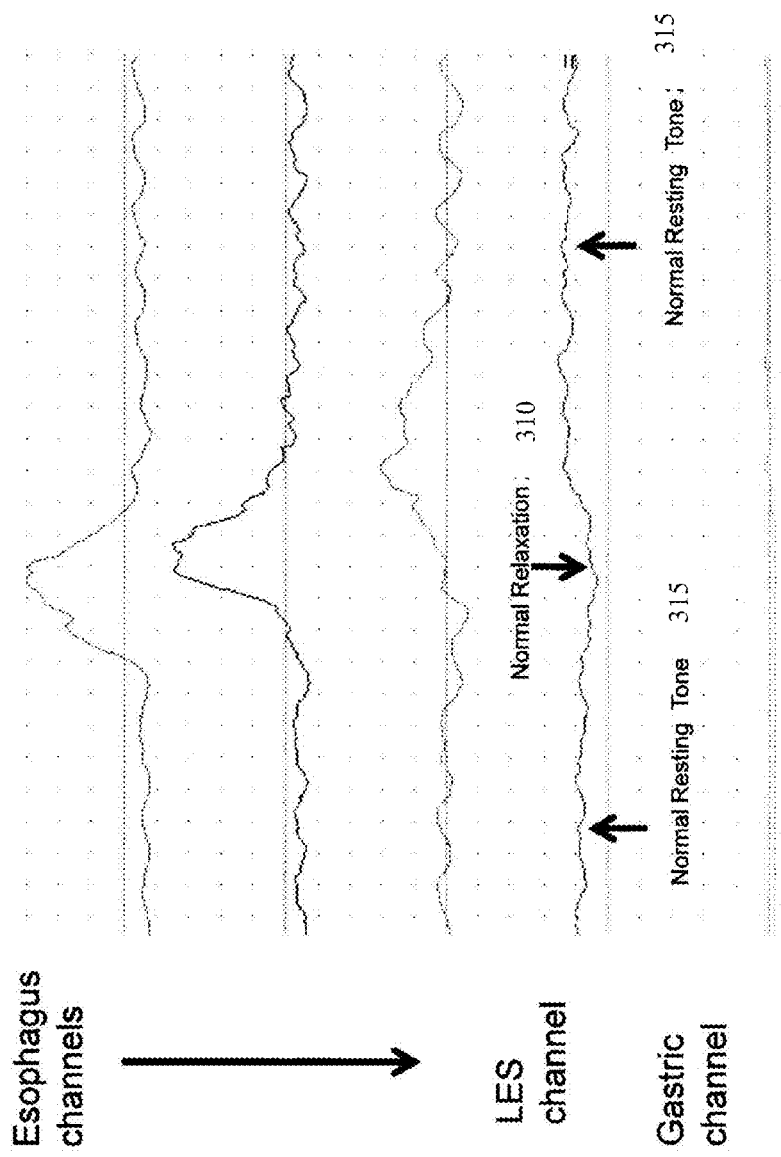
FIG. 3 depicts a wet swallow with stimulation.
Figure 4:
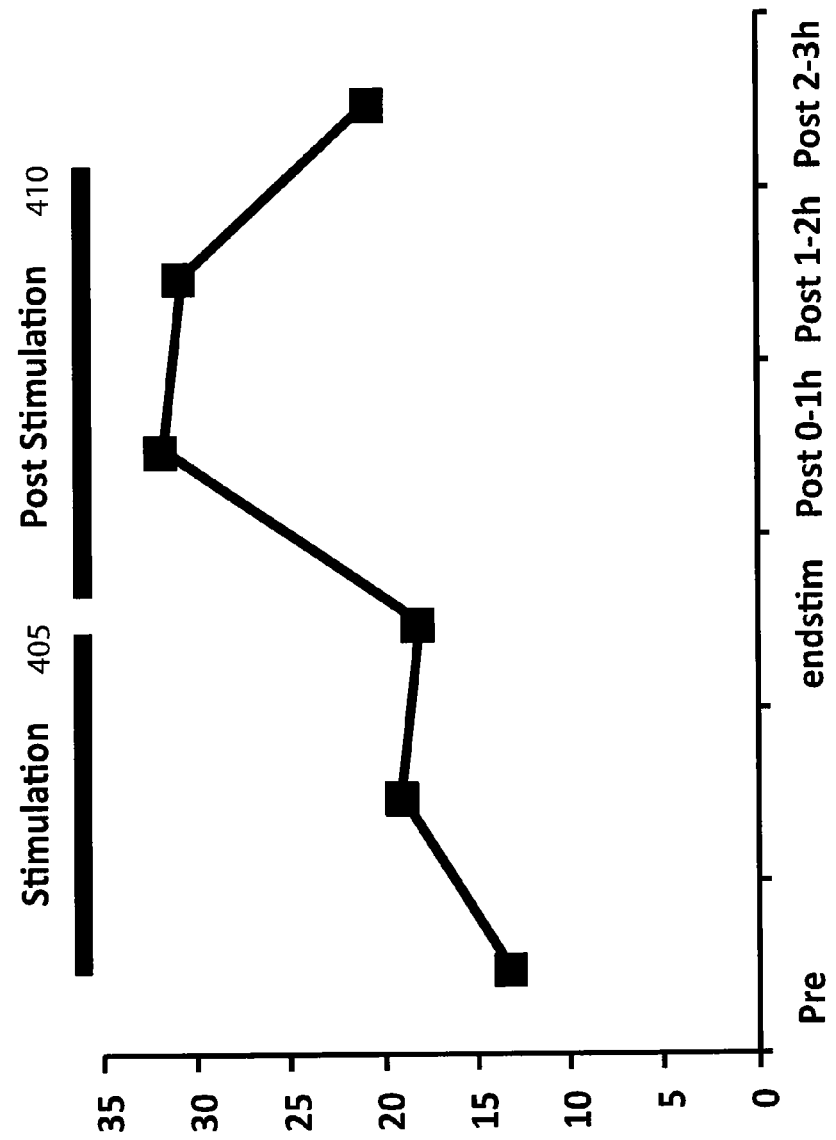
FIG. 4 depicts one exemplary pressure profile, both during stimulation and post-stimulation.
Figure 5:
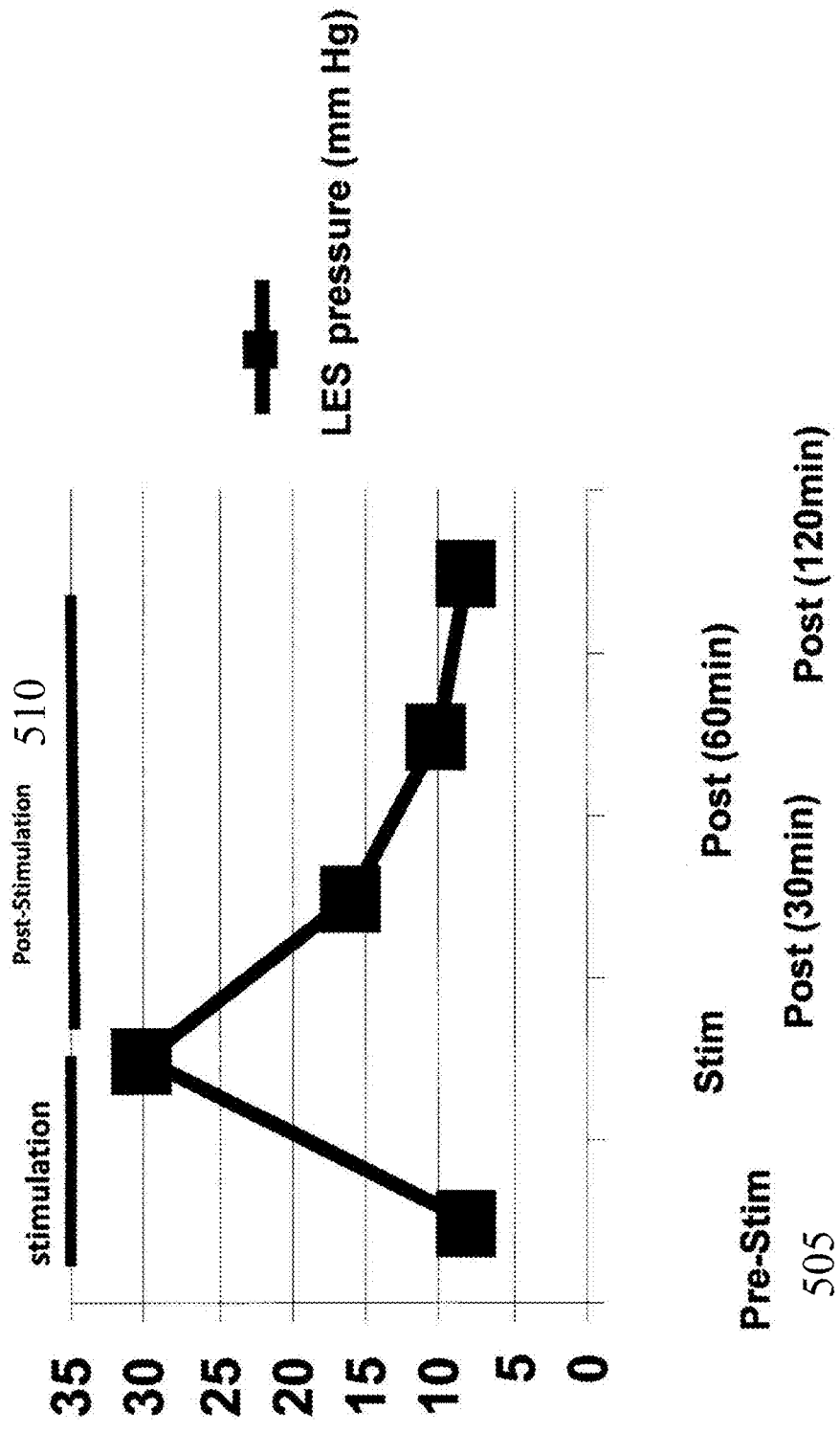
FIG. 5 depicts another exemplary pressure profile, both during stimulation and post-stimulation.
Figure 6:
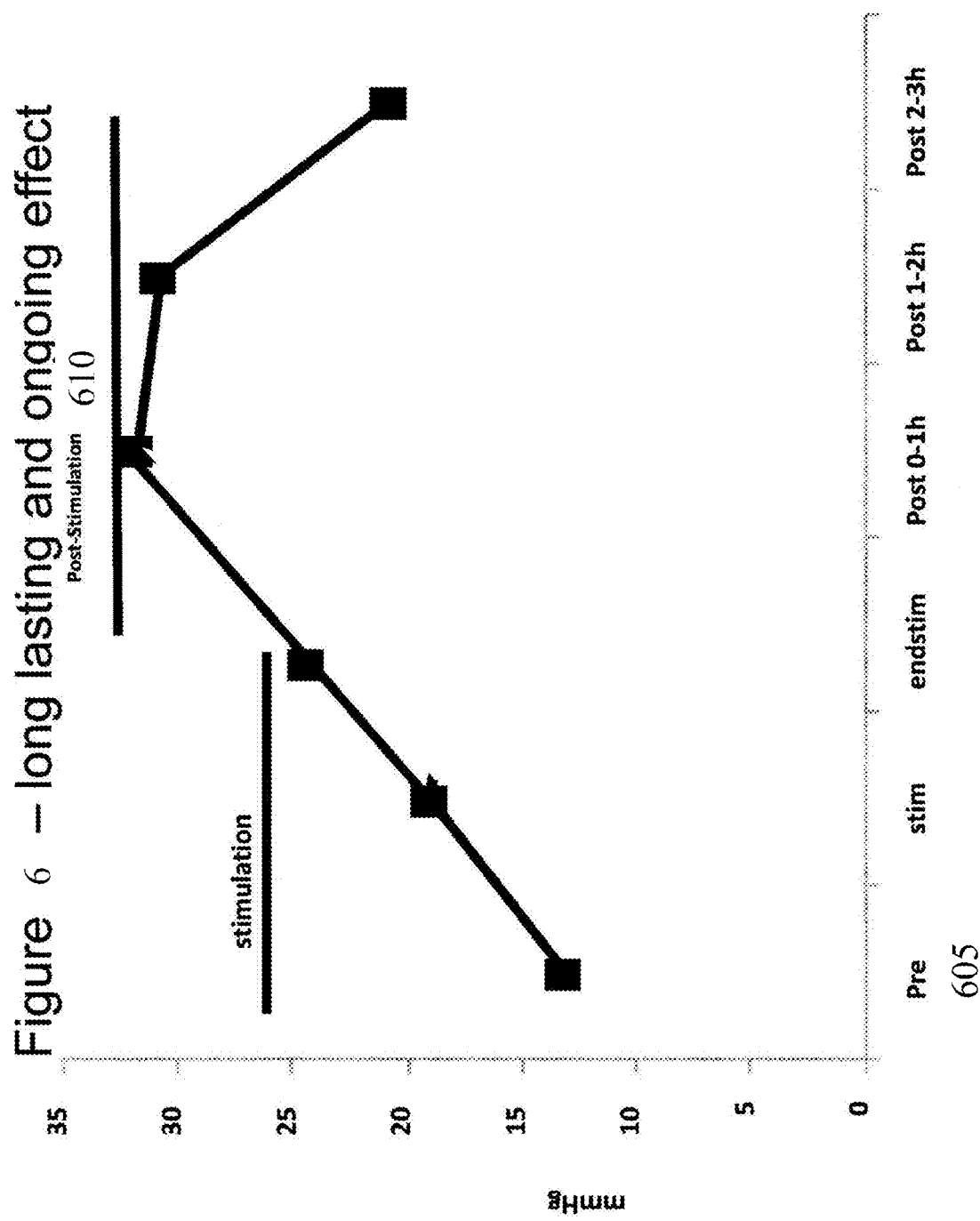
FIG. 6 depicts another exemplary pressure profile, both during stimulation and post-stimulation.

Referring to FIG. 2, in a typical GERD patient, the LES relaxes prior to swallow 205. Post-swallow, the LES increases pressure 210, which can be observed for a short duration following the swallow, and then reverts to a resting tone 215. It should be appreciated, however, that the resting tone 215 is too low to prevent reflux. Referring to FIG. 3, the resting tone 315, both before and after the relaxation 310 associated with a bolus swallow, is significantly increased using the devices and methodologies of the present invention, while still keeping intact the relaxation function 310. This represents a significant improvement over treatments that closed the LES and did not allow the muscle to properly relax during swallows, absent termination of stimulation.

Figure 7:
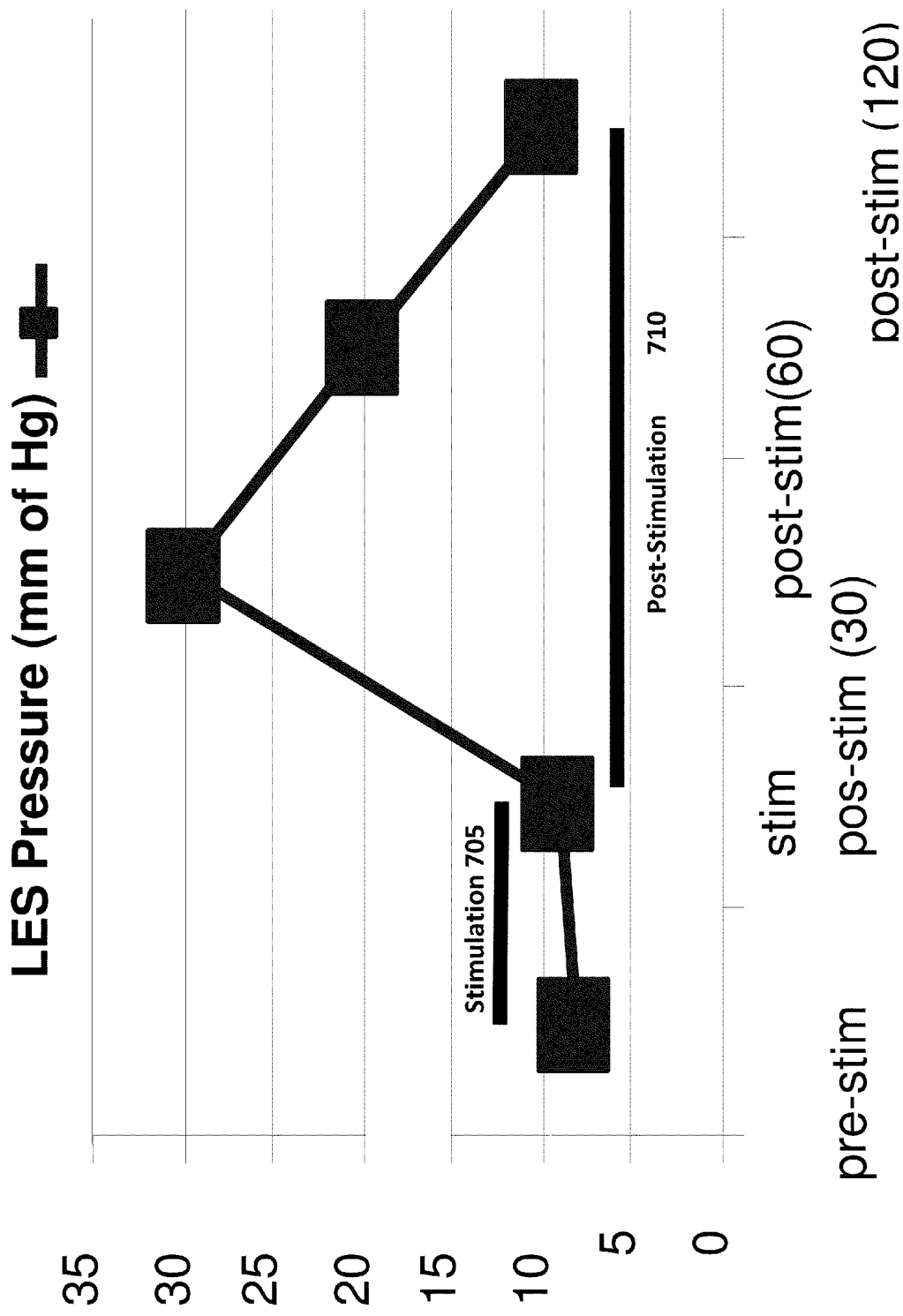
FIG. 7 depicts yet another exemplary pressure profile, both during stimulation and post-stimulation.

Referring to FIGS. 4-7, the presently disclosed methods and systems enable different post-stimulation residual effects, including an increase in LES pressure post-stimulation 410 followed by a decrease in LES pressure down to a stimulation state 405 over a period of 2 to 3 hours (FIG. 4), a slow decrease in LES pressure post-stimulation 510 back to a pre-stimulation LES pressure level 505 over a period of 1 to 2 hours (FIG. 5), a continued increase in LES pressure post-stimulation 610 followed by a decrease in LES pressure which still remains above a pre-stimulation state 605 after a period of 2 to 3 hours (FIG. 6), and minimal to no increase in LES pressure during stimulation 705 and a continued increase in LES pressure post-stimulation 710 followed by a decrease in LES pressure which still remains above a pre-stimulation state after a period of 2 to 3 hours (FIG. 7).

Accordingly, in one embodiment, the present invention encompasses a method for controlling muscle action using electrical stimulation by a modulated electrical signal having carrier frequency in the range of 2 KHz-100 KHz and an on-off modulating signal having an "on" duration in the range of 5 µs to 500 msec and, in particular, 200 µs.

In one embodiment, a pacemaker lead, such as a modified Medtronic 6416 200 cm, is secured to the LES in a submucosal tunnel using endoclips along the body of the lead and exteriorized nasally. Stimulation is applied using a 200 µsec to 3 msec pulse with a pulse amplitude of 1 mAmp to 15 mAmp, more preferably 5 mAmp to 10 mAmp, pulse frequency of preferably less than 1 msec, more preferably 200 µs, and a pulse width of 200 µsec. The patient's resting LES pressure, which is greater than or equal to 5 mmHg, is thereafter increased by at least 5%, more preferably 25-50%. Additionally, transient LES relaxation is improved by at least 5%, LES function is improved by at least 5%, esophageal body pressure is improved by at least 5%, esophageal body function is improved by at least 5%, symptoms of GERD are improved by at least 5%, esophageal acid exposure is improved by at least 5%, quality of life is improved by at least 5%, caloric intake is improved by at least 5%, and/or weight is improved by at least 5%.

These improvements are achieved without any affect on patient's swallow function, adverse symptoms, or cardiac rhythm disturbances. These improvements are also achieved by avoiding continuous electrical stimulation, which yields problems of muscle fatigue, build up of tolerance, tissue damage, and excessively high requirements for local energy storage, such as capacitor size or battery life.

In another embodiment, the stimulator may be operated using a pulse having a frequency of 20 Hz (1-100 Hz), a pulse amplitude of 1 µAmp-1 Amp, more preferably 1-20 mAmp, and a pulse width of 1 µsec-1 msec, and more preferably 100-500 µsec. The stimulator may also be stimulated using a pulse having a frequency of 20 Hz (1-100 Hz), a pulse amplitude of 1-20 mA (1 µAmp-1 Amp), and a pulse width of 1-50 msec (500 µsec-100 msec). The stimulator may also be stimulated using a pulse having a frequency of 5 cpm (1-100 cpm), a pulse amplitude of 1-20 mAmp (1 µAmp-1 Amp), and a pulse width of 100-500 msec (1 msec-1 sec).

In certain applications, there is an advantage to combining neural stimulation with direct muscle stimulation. Such applications include, for example, gastric stimulation for gastroparesis where a combined effect on gastric muscle and neural modulation can be synergistic in improving both gastric emptying rates and symptoms associated with gastroparesis. Another example can be the treatment of chronic reflux disease where both high frequency and low frequency pulses can have desirable effects on maintaining adequate lower esophageal sphincter tone or function while modulating the perception of symptoms associated with GERD.

In certain applications where an implantable electrode or a leadless device is used for delivering electrical stimulation, it is technically more feasible to apply lower pulse width (having higher frequency components) than signals having wider pulse duration. The reason is that irreversible electrochemical effects occur when the total charge transfer through the electrode-tissue interface at any given time increases above a certain threshold. In these cases electrolysis occurs which releases metal ions into the tissue, damages the electrode, and causes dangerous pH changes in the local tissue. This has negative effects on the electrode longevity and on the tissue and should be avoided especially in chronic applications where stimulation of the same site using the same electrode or device is planned for an extended period of time.

Some methods for overcoming the problems of using long pulse durations were developed that attempt to enhance the capacitance of the electrode-tissue interface so as to increase the threshold for irreversible effects thereby increasing the maximal pulse width that can be used chronically. Electrode capacitance can be increased in various ways, such as by enhancing effective electrode surface area by coating (e.g. coating with iridium-oxide or titanium nitride), by changing the electrode material, and/or by geometrical changes in the electrode shape. These methods, however, have some undesirable consequences, such as a significant increase in the manufacturing cost of the electrode and/or making the electrode unsuitable for specific implantation procedures. It is therefore useful to minimize the use of long pulse durations.

Furthermore, it should be noted that the use of square wave pulses, which is very common in conventional electrical stimulation systems, contains energy in frequency bands that are higher than the base rate of the pulse width. In general, when a square wave is used then most of the energy is delivered in the base rate and a portion of the energy is delivered in frequencies that are multiples (harmonics) of such base rate. Consequently, when a wide pulse width is delivered at a low frequency rate, some energy is also delivered in higher bands (multiples of the base rate) and also multiples of the reciprocal value of the pulse width. The practical effect, however, of these higher frequency components (or harmonics) is relatively small since only a small portion of the energy is delivered in these bands. It should further be appreciated that some frequencies, especially very high ones, are not absorbed in most tissues and can therefore be used as carriers to lower frequency signals that modulate them. Accordingly, high frequencies can be used to transfer or carry energy to the tissue without any physiological effect. Recovery of the low frequency signal is performed using a demodulator.

In light of the above, in one embodiment, a combination of low and high frequency signals (e.g. a waveform including both a high frequency component and a low frequency component) are delivered through an electrode or a leadless stimulating device with the purpose of applying two separate effects to the stimulated tissue and positively impacting lower esophageal sphincter tone. The low frequency signal will be modulated on a high frequency carrier known to be neutral to muscle tone whereas the low frequency signal will be demodulated by the tissue itself and deliver a separate impact on the tissue, which is known to occur with a direct muscle stimulation using low frequency signals. The signal is designed to have a zero net charge delivered to the tissue over durations shorter than 1 ms thereby allowing flexibility in electrode design far more than what would be required if using a long pulse duration directly.

Figure 8:
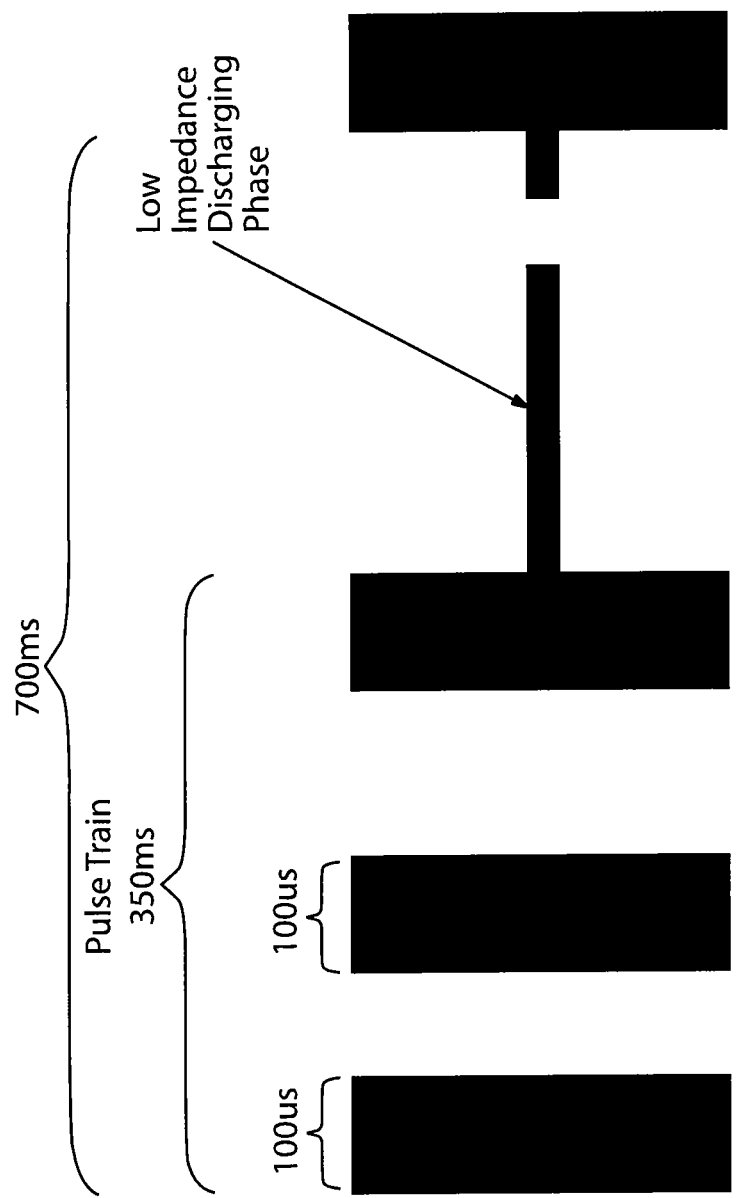
FIG. 8 is a schematic of modulated pulse trains.

In one embodiment, referring to FIG. 8, the modulation is achieved by pulse trains having a base high frequency and duration equal to the desired long pulse width. Here, the stimulation train does not have a net zero charge; therefore, in order to discharge the electrode-tissue capacitance, a 350 msec time period can be deployed, using a low impedance pathway switched by the stimulation device. Alternatively, a single negative discharging pulse can be applied once every 700 msec cycle. The low impedance connection can also preferably be applied following each of the 100 µsec pulses thereby minimizing the maximal net charge accumulated on the electrode-tissue capacitance. There are several advantages of this waveform configuration: 1) the longest pulse duration applied is 100 µsec thereby relaxing the demands on a chronically implantable electrode capacitance that would have been required for a 350 msec pulse duration; 2) a train duration of 350 msec adds a low frequency component which is known to have a direct positive effect on muscle tone; 3) there is a reduced energy requirement from the device, resulting from the lower total pulse durations; and 4) the total stimulation result is optimized by a combination of two different frequency bands, each controlling the muscle through an independent physiological mechanism.

In another embodiment, the present invention encompasses an apparatus comprising a housing, pulse generator capable of generating square waves in the frequency range of 2 KHz-100 KHz, conductive tissue interface, means for fixation of conductive tissue interface to muscle tissue, programmable control unit capable of delivering said pulse generator output to the tissue intermittently whereas each "on" duration can be programmable in the range of 5 μsec to 500 msec and an "off" duration programmable in the same or different range. Optionally, the muscle tissue is the LES, esophagus, or UES. Optionally, the carrier frequency is in the range of 40 KHz-60 KHz and "on" duration is 300-400 msec. Optionally, the signal structure may be triggered by other timing mechanisms, including various patient-specific attributes, activities, and states. Optionally, a control unit, which is separate from a microstimulation device, includes a demodulator and a pulse generator for the high frequency carrier, transmits energy to the microstimulator to power the pulse generator, and includes modulation information using a different carrier frequency. Optionally, the stimulation device comprises multiple leads output and alternates a modulation signal between two or more stimulation locations where, while one location has an "on" state, the other location has an "off" state, and vice-versa.

In another embodiment, the stimulator may be stimulated using an "on" phase and an "off" phase, wherein the on phase is between 1 minute and 1 hour and the off phase is between 1 minute and 1 hour. Preferably, both the on and off phases are between 5 and 30 minutes. In another embodiment, the stimulator or microstimulator may be stimulated using a combination of a low frequency pulse and an intermediate or high frequency pulse. In one embodiment, the low frequency pulses are delivered for a duration that is 1% to 1000% of the intermediate or high pulse duration.

In another embodiment, the stimulator may be stimulated using an "on" phase and an "off" phase, wherein the on phase is between 1 second and 24 hours and the off phase is between 1 second and 24 hours. Preferably, the off phase is longer than the on phase. In this embodiment, the stimulator or microstimulator may be stimulated using a combination of a low frequency pulse and an intermediate or high frequency pulse. In one embodiment, the low frequency pulses are delivered for a duration that is 1% to 1000% of the intermediate or high pulse duration. In another embodiment a combination of same frequency pulse with varying amplitude can be used. For example a patient can receive intermittent or continuous stimulation at a lower amplitude with one or more session of stimulation at a higher amplitude where the high amplitude is at least twice the low amplitude.

It should be appreciated that, wherever stimulation parameters are described, the stimulation may be initiated by "ramping up" to the stated stimulation levels or may be terminated by "ramping down" to an off state. The ramp up and ramp down can be as slow or as fast as required to effectuate the required therapy.

In one embodiment, the programmed duty cycle, pulse frequency, pulse width, pulse amplitude of the stimulator and corresponding electrode configuration are configured to trigger secretion of neurokinin A (NKA) or a similar peptide. The configuration of the frequency and amplitude is set to efficiently achieve a clinically significant secretion with minimal energy. The session duration can make use of the long degradation time of NKA and be configured to turn off stimulation following the expected accumulation of sufficient NKA secretion. Electrode configuration, as further described below, can be adapted so that the desired optimal session duration will alternate in different regions using implantation of electrodes in different regions of the LES. The configuration of the stimulation to impact local NKA level can be designed to achieve the required pressure curve as described in FIGS. 4-7.

It should further be noted that, because the stimulation device enables the therapeutically effective treatment of a plurality of ailments, as described above, at currents below 15 mAmp, one can avoid subjecting the patient to physical pain, sensation, or discomfort. The present system can achieve the therapeutic goals and effectively operate by delivering lower stimulation levels for longer periods of time, such as by delivering 3 mAmp for 10 minutes rather than 15 mAmp for 5 minutes. The pulse frequency can be 20 Hz and the stimulation can be delivered less than five times per day, such as three times per day.

In one embodiment, the presently disclosed methods and devices achieve any of the aforementioned therapeutic objectives by providing or implanting a stimulation device, such as a macrostimulator or microstimulator, adapted to be implanted within the patient's lower esophageal sphincter and adapted to apply electrical stimulation to the patient's lower esophageal sphincter; and programming, using, or operating said stimulation device, wherein said programming, use, or operation defines, uses, or is dependent upon a plurality of stimulation parameters that determine the application of electrical stimulation to the patient's lower esophageal sphincter and wherein said stimulation parameters are selected, derived, obtained, calculated, or determined, at least in part, to account for a latent, delayed, time-delayed, or future response of the patient's lower esophageal sphincter.

In one embodiment, the presently disclosed methods and devices achieve any of the aforementioned therapeutic objectives by providing or implanting a stimulation device adapted to be implanted within the patient's lower esophageal sphincter and to apply electrical stimulation to the patient's lower esophageal sphincter, wherein said lower esophageal sphincter exhibits a latent, delayed, time-delayed, or future response to applied electrical stimulation; and treating said patient by applying electrical stimulation based upon derived from, or dependent upon said latent, delayed, time-delayed or future response.

In one embodiment, the presently disclosed methods and devices achieve any of the aforementioned therapeutic objectives by providing or implanting a stimulation device adapted to be implanted within the patient's lower esophageal sphincter and to apply electrical stimulation to the patient's lower esophageal sphincter; and initiating, activating, beginning, or starting said electrical stimulation prior to a pre-defined or fixed time wherein said pre-defined or fixed time is associated with a GERD triggering event and wherein said initiation occurs prior to said pre-defined or fixed time by a minimum period, such as at least 5 minutes, 10 minutes, 15 minutes, 30 minutes, 1 hour, 2 hours, 3 hours, 12 hours, 24 hours, or any time increment therein.

In one embodiment, the presently disclosed methods and devices achieve any of the aforementioned therapeutic objectives by providing or implanting a stimulation device adapted to be implanted within the patient's lower esophageal sphincter and adapted to apply electrical stimulation to the patient's lower esophageal sphincter; and initiating, activating, beginning, or starting said electrical stimulation prior to a pre-defined or fixed time wherein said pre-defined or fixed time is associated with a GERD triggering event and wherein said initiation occurs prior to said pre-defined or fixed time by a minimum period, such as at least 5 minutes, 10 minutes, 15 minutes, 30 minutes, 1 hour, 2 hours, 3 hours, 12 hours, 24 hours, or any time increment therein; and terminating said electrical stimulation after said pre-defined or fixed time has passed.

In one embodiment, the presently disclosed methods and devices achieve any of the aforementioned therapeutic objectives by providing or implanting a stimulation device adapted to be implanted within the patient's lower esophageal sphincter and adapted to apply electrical stimulation to the patient's lower esophageal sphincter; and programming, using, or operating said stimulation device, wherein said programming, use, or operation defines, uses, or is dependent upon a plurality of stimulation parameters that determine the application of electrical stimulation to the patient's lower esophageal sphincter and wherein said stimulation parameters are selected, derived, obtained, calculated, or determined, at least in part, to treat GERD without inhibiting, hindering, stopping, or preventing the patient from swallowing.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation while the patient swallows, during periods of esophageal motility, or during esophageal peristalsis.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation in accordance with a preset period and wherein said preset period is not dependent upon, influenced by, modified by, lengthened by, or shortened by a physiological state of a patient.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation in accordance with a preset period and wherein said preset period is not dependent upon, influenced by, modified by, lengthened by, or shortened by the patient swallowing, esophageal motility, esophageal peristalsis, or being in a feeding state.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation that is not dependent upon, influenced by, modified by, lengthened by, or shortened by a physiological state, biological parameter, sensed physiological or biological parameters of a patient.

In one embodiment, the presently disclosed methods and devices achieve any of the aforementioned therapeutic objectives by providing or implanting a stimulation device adapted to be implanted within the patient's lower esophageal sphincter; and treating said patient by applying electrical stimulation that is not dependent upon, influenced by, modified by, lengthened by, or shortened by the patient swallowing, esophageal motility, esophageal peristalsis, or being in a feeding state.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying sufficient electrical stimulation to increase said pressure but not to inhibit, hinder, stop, or prevent swallowing, esophageal motility, esophageal peristalsis, or being in a feeding state.

In one embodiment, the presently disclosed methods and devices achieve any of the aforementioned therapeutic objectives by providing or implanting a stimulation device adapted to be implanted within the patient's lower esophageal sphincter, wherein the lower esophageal sphincter has a function, and treating the patient by applying sufficient electrical stimulation to improve the function but not to inhibit, hinder, stop, or prevent swallowing, esophageal motility, or esophageal peristalsis or dissuade a patient from being in a feeding state.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes an increase in said pressure of at least 5% only after an elapsed period of time of at least one minute.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation improves or normalizes lower esophageal function, improves or normalizes LES pressure, or increases LES pressure to a normal physiological range only after an elapsed period of time or only after a delay of at least one minute.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes a non-instantaneous or delayed increase in said pressure.

In one embodiment, the presently disclosed methods and devices achieve any of the aforementioned therapeutic objectives by providing or implanting a stimulation device adapted to be implanted within the patient's lower esophageal sphincter, wherein the lower esophageal sphincter has a function, and treating the patient by applying electrical stimulation, wherein the stimulation causes a non-instantaneous or delayed improvement in the function.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes a non-instantaneous or delayed increase in said pressure and wherein said non-instantaneous or delayed increase in the pressure normalizes LES function, normalizes LES pressure, increases LES pressure to a normal physiological range, or increases LES pressure by at least 3%.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure;

and treating said patient by applying electrical stimulation, wherein said stimulation causes a gradual increase in said pressure.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation, wherein said stimulation causes an increase in said pressure after said electrical stimulation is terminated.

In one embodiment, the presently disclosed methods and devices achieve any of the aforementioned therapeutic objectives by providing or implanting a stimulation device adapted to be implanted within the patient's lower esophageal sphincter, wherein said lower esophageal sphincter has a pressure; and treating said patient by applying electrical stimulation having a first level, wherein said stimulation causes an increase in said pressure after said electrical stimulation is decreased from said first level.

In one embodiment, the presently disclosed methods and devices achieve any of the aforementioned therapeutic objectives by improving the pressure or function of the patient's lower esophageal sphincter.

In one embodiment, the presently disclosed methods and devices achieve any of the aforementioned therapeutic objectives, wherein said patient has a lower esophageal sphincter and wherein said lower esophageal sphincter has a pressure, by increasing the pressure of the patient's lower esophageal sphincter through the application of electrical stimulation to the lower esophageal sphincter or areas proximate thereto.

In one embodiment, the presently disclosed methods and devices achieve any of the aforementioned therapeutic objectives, wherein said patient has a lower esophageal sphincter and wherein said lower esophageal sphincter has a pressure, by increasing the pressure of the patient's lower esophageal sphincter through the application of electrical stimulation to the lower esophageal sphincter or areas proximate thereto, and wherein said pressure does not inhibit or otherwise hinder the patient's ability to swallow.

In one embodiment, the presently disclosed methods and devices achieve any of the aforementioned therapeutic objectives by modifying the pressure or function of the patient's lower esophageal sphincter.

In one embodiment, the presently disclosed methods and devices achieve any of the aforementioned therapeutic objectives by modifying the pressure or function of the patient's lower esophageal sphincter through the application of electrical stimulation to the lower esophageal sphincter or areas proximate thereto.

In one embodiment, the presently disclosed methods and devices achieve any of the aforementioned therapeutic objectives by modifying the pressure or function of the patient's lower esophageal sphincter through the application of electrical stimulation to the lower esophageal sphincter or areas proximate thereto and wherein said pressure does not inhibit or otherwise hinder the patient's ability to swallow.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation in accordance with at least one on period, wherein said on period is between 1 second and 24 hours and is not triggered by, substantially concurrent to, or substantially simultaneous with an incidence of acid reflux, and at least one off period, wherein said off period is greater than 1 second.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation, wherein a pulse amplitude from a single electrode pair ranges from greater than or equal to 1 mAmp to less than or equal to 8 mAmp.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation having a pulse duration of approximately 200 μsec.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation having a pulse duration of approximately 1 msec.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation having a pulse energy level of <10 mAmp, pulse duration of <1 second, and/or pulse frequency of <50 Hz.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation having a pulse energy level of 1 mAmp to 10 mAmp (preferably 1 mAmp), pulse duration in a range of 50 μsec to 1 msec (preferably 215 μsec), a pulse frequency of 5 Hz to 50 Hz (preferably 20 Hz), pulse on time in a range of 10 minutes to 120 minutes (preferably 30 minutes), and/or pulse off time in a range of 10 minutes to 24 hours.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation to increase LES pressure above a baseline or threshold LES pressure, wherein said LES pressure remains above said baseline or threshold LES pressure after termination of electrical stimulation.

In one embodiment, the presently disclosed methods and devices achieve any of the aforementioned therapeutic objectives by providing or implanting a stimulation device adapted to be implanted within the patient's lower esophageal sphincter, and treating said patient by applying electrical stimulation to increase LES tone above a threshold LES tone, wherein said LES tone remains above said threshold LES tone after termination of electrical stimulation.

In one embodiment, the presently disclosed methods and devices provide a macrostimulator programmed, adapted to, or configured to perform any of the aforementioned methods or treatment protocols.

In one embodiment, the presently disclosed methods and devices provide a macrostimulator comprising at least one electrode, an energy source, and a pulse generator in electrical communication with the at least one electrode and energy source, wherein said pulse generator is programmed, adapted to, or configured to perform any of the aforementioned methods or treatment protocols.

In one embodiment, the presently disclosed methods and devices provide a microstimulator programmed, adapted to, or configured to perform any of the aforementioned methods or treatment protocols.

In one embodiment, the presently disclosed methods and devices provide a microstimulator comprising at least one electrode, an energy source, and a pulse generator in electrical communication with the at least one electrode and energy source, wherein said pulse generator is programmed, adapted to, or configured to perform any of the aforementioned methods or treatment protocols.

Such treatment methods may be combined, directed toward any of the aforementioned therapeutic objectives, and/or implemented through stimulating any of the aforementioned anatomical areas. The treatment methods may be further modified by using specific stimulation parameters, open loop data processes, closed loop data processes, the patient's physical position and degree of activity, the patient's eating state, timing, quantity or content thereof, certain physiological parameters sensed by the device, including LES pressure, or anti-habituation methods to prevent anatomical habituation to a specific set of stimulation parameters. Additionally, because the device can operate on a time-based schedule, not necessarily physiological triggers (although a physiological trigger can be an optional embodiment), stimulation schedules can be tailored to user behavior and/or routine. For example, stimulation therapy can be delivered or stimulation energy can be transmitted at times that are most convenient, least disruptive to the patient's activities of daily living, such as only scheduling stimulation while the patient is sleeping, relaxing, or watching TV and scheduling stimulation only after mealtimes. Such additional embodiments are described below.

Open Loop Programming

In one optional embodiment, the stimulation parameters, including pulse width, pulse frequency, pulse amplitude, ramp rates, and/or duty cycle, can be modified by a physician using data sensed by, stored within, or transmitted from the stimulation device, data sensed by, stored within, or transmitted from a sensor implanted in the patient, and/or data captured by an external computing device used by a patient. A stimulator device having a local memory, or a transmitter capable of communicating sensed information to a remotely located memory or memory external to the patient, captures a plurality of sensed data, as discussed in greater detail below. Concurrently, a patient controlled computing device, such as a laptop, personal computer, mobile device, or tablet computer, which is external to the patient is used by the patient to store data input by the patient relevant to evaluating, monitoring, and adjusting the operation of the stimulator. Both the stimulator captured data and patient inputted data is then transmitted to a physician controlled device, as described below, to enable the physician to properly evaluate, monitor, and modify the stimulation parameters.

In one embodiment, the patient-controlled computing device comprises a plurality of programmatic instructions that, when executed, generate a display which prompts a user for, and is capable of receiving input from the user, information regarding the user's food intake, the timing of such food intake, exercise regimen, degree and extent of physical symptoms, incidents of acid reflux, when the user sleeps, when the user lays down, type of food being consumed, quantity of food, among other variables. This data can be captured and stored locally and/or transmitted to a remote server for access by a physician. If accessed remotely by a physician, the physician can transmit alerts back to the patient, via a network in communication with the computing device or conventional communication systems, such as email, text messaging or phone, to confirm dose amounts, patient state information, or provide for therapy adjustment.

In one embodiment, the stimulator captured data includes what stimulation parameters were used and when, the sensed LES pressure profile, including the percentage or amount of time the LES pressure was below a certain threshold level, such as 10 mmHg, or above a $2^{nd}$ threshold level, such as 20 mm Hg, the occurrence of t-LESRs, esophageal pH, supine events, degree of physical movement, among other variables.

The patient-inputted data, when combined with the stimulator captured data, can provide a holistic view of the patient's condition and the efficacy of a stimulation regimen. In particular, as patient symptoms are mapped to stimulation parameters and analyzed in relation to food or drink intake, sleep, and exercise regimens, a physician will be able to determine how best to modify the stimulation parameters, including duty cycle, stimulation initiation times or triggers, stimulation termination times or triggers, pulse width, pulse amplitude, duty cycle, ramp rates, or pulse frequency, to improve patient treatment. As further discussed below, the physician will receive both the patient-captured and stimulation device captured data into a diagnostic terminal that can be used to process the information and transmit new stimulation parameters, if necessary, to the stimulation device. For example, the physician can modify the stimulation parameters in a manner that would lower the incidents of reported acid reflux, generalized pain, pain while swallowing, generalized discomfort, discomfort while swallowing, or lack of comfort during sleeping or physical exercise. The physician can also modify the stimulation parameters, including the initiation and termination of stimulation, to better match one or more GERD triggering events, such as eating, sleeping, lying down, or engaging in physical activity. The physician can also modify the stimulation parameters, including the initiation and termination of stimulation, to better match the patient's personal work or vacation schedule.

Additionally, alerts can be created that can be either programmed into the patient-controlled device or stimulation device which serve to notify the patient of a device malfunction, a recommendation to take a drug, a recommendation to come back for a checkup, among other variables. Those alerts can also be transmitted, via a computing network, to the physician. Furthermore, external data sources, such as demographic data or expert protocols, can be integrated into the physician system to help the physician improve the diagnostic and evaluation process and optimize the programmed set of stimulation parameters.

It should further be appreciated that, as the patient controlled device and stimulator device accumulate data that maps the therapeutic regimen against the patient's activities and symptoms, the patient controlled device will be able to determine, and therefore inform the patient of, patterns which tend to increase or decrease the incidents of GERD, including types of food, quantity of food, timing of eating, among other variables.

Closed Loop Programming

In one optional embodiment, the stimulation parameters, including pulse width, pulse frequency, pulse amplitude, initiation of stimulation, triggers for stimulation, termination of stimulation, triggers to terminate stimulation, ramp rates, and/or duty cycle, can be dynamically and intelligently modified by the stimulation device using data sensed by, stored within, or transmitted from the stimulation device, data sensed by, stored within, or transmitted from a sensor implanted in the patient, and/or data captured by, stored within, and/or transmitted from an external computing device used by a patient.

As discussed above, data maybe captured by a patient-controlled device and/or the stimulator device. In this embodiment, a stimulator is further programmed to intelligently modify stimulation parameters, without physician input, based upon sensed data and/or patient inputs. In one embodiment, a stimulator determines that LES pressure or function fails to improve above a predefined threshold, even after a predefined amount of stimulation, and, accordingly, automatically modifies the stimulation parameters, within a preset range of operation, to yield an improvement in LES pressure increase. In one embodiment, a stimulator determines that LES pressure or function improves significantly above a predefined threshold, after a predefined amount of stimulation, or maintains a level above a predefined threshold and, accordingly, automatically modifies the stimulation parameters, within a preset range of operation, to yield an improvement in LES pressure levels or function.

In one embodiment, a stimulator determines the LES pressure levels remain above a predefined threshold level for a sufficient amount of time such that a subsequent pre-programmed stimulation session or sessions can be postponed or cancelled. In one embodiment, a stimulator device monitors LES pressure and initiates stimulation only when LES pressure falls below a predetermined threshold. Preprogrammed stimulation may be modified in order to continue or increase in energy, duration, or frequency until LES pressure rises above a predetermined threshold. The LES pressure threshold may be dynamically modified based upon sensed data.

In one embodiment, a stimulator determines that esophageal pH is indicative of incidents of acid reflux above a predefined threshold level, and, accordingly, automatically modifies the stimulation parameters, within a preset range of operation, to yield an improvement in LES pressure increase to lower such incidents. In one embodiment, a stimulator receives a communication from an external patient controlled device indicating that the patient is reporting a number of adverse incidents above a predefined threshold, such as acid reflux, generalized pain, pain while swallowing, generalized discomfort, discomfort while swallowing, lack of comfort when sleeping, etc. and, accordingly, automatically modifies the stimulation parameters, within a preset range of operation, to yield a lower level of such incidents. In one embodiment, a stimulator receives a communication from an external patient controlled device detailing a schedule of potentially GERD triggering events, including sleep times, eating times, or exercise times, and, accordingly, automatically modifies the stimulation parameters, within a preset range of operation, to properly account for such GERD triggering events.

In one embodiment, the stimulator operates using both open loop and closed loop programming. Stimulation parameters may be established using open loop programming methods, as described above, and then modified through the aforementioned closed loop programming methods. Stimulation parameters may also be established using closed loop programming methods, as described above, and then modified through the aforementioned open loop programming methods.

Stimulation Modification Based on Sensed Data

It should be appreciated that the stimulation device may stimulate based on a plurality of data, including based on LES pressure registering below a predefined threshold, based on a patient's pH level, based on the patient's physical orientation, based on the patient's meal intake, or based on a predefined time period, among other triggers. It should also be appreciated that the controller may initiate or stop a stimulation based on a plurality of triggers, including based on the LES pressure exceeding a predefined threshold, based on a patient's pH level, based on the patient's physical orientation, or based on a predefined time period, among other triggers.

Using various data sensors, including, but not limited to impedance, electrical activity, piezoelectric, pH, accelerometer, inclinometer, ultrasound-based sensors, RF-based sensors, or strain gauge, the stimulator device can determine whether a patient is eating, how much the patient is eating, how long the patient is eating, and/or what the patient is eating, and, based on that information, adjust stimulation parameters accordingly. In particular, pH data may be used to determine what kind of food a patient is eating, where the type of food is defined in terms of its acidity.

In one embodiment, the stimulator device senses LES pressure and initiates stimulation of the LES when the pressure is below a pre-defined threshold level for a predefined period of time and terminates stimulation of the LES when the pressure is above a pre-defined threshold level for a predefined period of time. LES pressure may be determined by sensing and processing impedance measurements, electrical activity measurements, strain gauge, and/or piezoelectric measurements. One or more of the various measurements are constantly measured to create a contiguous LES pressure profile. Based upon the LES pressure profile, the stimulator can modify stimulation parameters, including pulse amplitude, pulse width, duty cycle, pulse frequency, stimulation initiation time, ramp rate, or stimulation termination time, to achieve, with respect to the LES pressure, an absolute amount of change, a percentage amount of change, increases or decreases above or below a threshold value, increases or decreases based on time, increases or decreases based on a LES pressure slope, among other measures of change.

In another embodiment, the stimulator device uses various data sensors to determine the pulmonary, intra-thoracic, or intra-abdominal pressure and, based on pulmonary, intra-thoracic, or intra-abdominal pressure, create a patient-specific dose, such as a specific pulse amplitude, pulse width, duty cycle, pulse frequency, stimulation initiation time, ramp rate, or stimulation termination time, required to affect LES tone, pressure, or function to the levels needed by that patient.

In another embodiment, the stimulator device uses various data sensors to determine the esophageal temperature and, based on that temperature reading, create a patient-specific dose, such as a specific pulse amplitude, pulse width, duty cycle, pulse frequency, stimulation initiation time, ramp rate, or stimulation termination time.

In another embodiment, the stimulator device uses various data sensors to determine the esophageal pH and, based on that pH reading, create a patient-specific dose, such as a specific pulse amplitude, pulse width, duty cycle, pulse frequency, stimulation initiation time, ramp rate, or stimulation termination time.

In another embodiment, the stimulator device uses a combination of data inputs from the above described sensors to generate a total score from which a stimulation therapeutic regimen is derived. For example, if the patient has not eaten for a long time and lays down, a lower (or no) therapy dose would be delivered. Since GERD is an episodic disease and certain periods are more vulnerable to a reflux event than others, detecting various patient parameters by various means and using them in an algorithm enables clinicians to target those specific reflux events. In addition, in various embodiments, multiple algorithms are programmed into the stimulator device so that treatment can be tailored to various types of GERD, based upon input relayed by the sensors. In one embodiment, data from any combination of one or more of the following parameters is used by an algorithm to determine stimulation protocol: patient feed state including type of intake (via patient input or eating detection by a physical sensor that can detect and/or evaluate liquids/solids/caloric value); patient position (via inclinometer/accelerometer); patient activity (via accelerometer/actimeter); patient reflux profile (via patient input/pH recording); LES pressure; LES electrical activity; LES mechanical activity (via accelerometer in the LES, pressure sensor, impedance measure or change thereof); gastric pressure; gastric electrical activity; gastric chemical activity; gastric temperature; gastric mechanical activity (via an accelerometer in the stomach, pressure sensor, impedance measurement and changes); patient intuition; vagal neural activity; and, splanchnic neural activity. Based on input from one or more of the above parameters, the algorithm quantifies the vulnerability for a reflux event and modifies accordingly the amplitude, frequency, pulse-width, duty cycle, ramp rate, and timing of stimulation treatment. The table below lists the parameters, measurements, and values used in an exemplary treatment protocol of one embodiment of the present invention.

TABLE 3

| Parameter | Measurement | Value |
|---|---|---|
| LES Pressure | Normal | 0 |
|  | Low | 1 |
| Inclination | Upright | 0 |
|  | Supine | 1 |
| Feed State | Fasting/Pre-prandial | 0 |
|  | Post-prandial | 1 |
| Time of the day | Day time | 0 |
|  | Night time | 1 |
| Fat content of meal | Low | 0 |
|  | High | 1 |
| Patient pH Profile | Low-risk period | 0 |
|  | High-risk period | 1 |
| Patient Symptom Input | Low-risk period | 0 |
|  | High-risk period | 1 |
| Gastric Activity | Food Absent | 0 |
|  | Food Present | 1 |
| Upright Activity Level | Low | 0 |
|  | High | 1 |
| Supine Activity Level | High | 0 |
|  | Low | 1 |
| Patient Intuition | Low Likelihood | 0 |
|  | High Likelihood | 1 |

In the table above, each individual parameter is given a score of 1 or 0 depending on the value measured. In one embodiment, a summary score is tabulated using one or more parameters in the above exemplary algorithm scoring system to determine patient vulnerability to a reflux event. Based on the score, the treatment parameter is modified. Patients with a higher summary score are indicated for a greater level of treatment. For example, a patient with normal LES pressure in the upright position and a pre-prandial state will be at minimal risk for a reflux event and no therapy will be indicated. Conversely, a patient with low LES pressure in the supine position and an immediate post-prandial state will be at the highest risk for a reflux event and would receive the highest level of GERD therapy.

In one embodiment, a measured parameter is used as a modifier for another parameter. For example, gastric activity showing food absent does not have an individual score but modifies the feed state score from a post-prandial score to a fasting/pre-prandial score. In another embodiment, a measured parameter has an absolute value that is not impacted by other measured parameters. For example, patient intuition of a high likelihood of a reflux event is an absolute parameter that delivers the highest level of GERD therapy irrespective of other sensed parameters.

In one embodiment, the scoring system for certain individual parameters is a scale rather than a binary score. For example, in one embodiment, the score given to LES pressure is within a range from 0-5 based on duration of low pressure. With each incremental 5 minute duration of low LES pressure, the score increases by one increment.

In another embodiment, different weight is given to different parameters. For example, in one embodiment, low LES pressure is given an absolute score higher than post-prandial feed state.

In another embodiment, the scoring system is tailored to be patient specific. In one embodiment, for example, for a patient with low symptom predictability as ascertained by symptom association with a standard pH test, patient symptom input is given a lower weight. In another embodiment, for a patient with mostly upright reflux on pH testing, the upright position is given a greater weight than the supine position. In yet another embodiment, for a patient with exercise induced reflux, a greater weight is given to upright activity while the same parameter receives a low weight or is eliminated from the algorithm in a patient without exercise induced reflux.

Accelerometer/Inclinometer Based Stimulation System

In one embodiment, the implantable device includes an accelerometer or inclinometer and a pre-programmed supine stimulation mode intended to automatically provide the patient with additional stimulation sessions during extended time periods in which the patient is in the supine position, as noted by said accelerometer/inclinometer. When the mode is enabled by a programmer, a supine position detection triggers additional stimulation sessions based on pre-set programmable conditions. In one embodiment, additional stimulation sessions will be initiated automatically when the following two conditions are met: 1) the patient is supine (based on a programmable range of inclination) for a minimum amount of time (based on pre-set time ranges) and 2) no stimulation was applied recently (maximal time programmable).

In one embodiment, the supine stimulation mode can be enabled or disabled by the user via a programmer interface. The supine stimulation mode is available when the implantable device is in "cyclic" and "dose" modes, but not available (grayed out) when the device is in "continuous" and "off" modes. In another embodiment, the supine stimulation mode can be implemented in conjunction with other stimulation modes, as described above, be the only mode of stimulation, or be disabled. In addition, when active, the supine stimulation mode may or may not override regularly scheduled stimulations or manually applied stimulations, depending on the programming. Further, when active, the supine stimulation mode may or may not deliver the same stimulation therapy profile as programmed in the "cyclic", "dose", or other modes, as applicable, depending on the programming.

In one embodiment, when the supine stimulation mode is enabled, an additional set of specific programmable parameters becomes active on the programmer interface. This set includes the following parameters: supine time; supine time percentage; supine refractory time; supine level; supine retrigger time and, supine cancel.

Supine time defines the period of time that is required for the patient to be in a supine position in order for the first condition listed above to be met. Supine time is programmable to a certain time period by the user. In one embodiment, supine time is set to 1 minute. In another embodiment, supine time is set to 5 minutes. In another embodiment, supine time is set to 30 minutes. In yet another embodiment, supine time is set to 60 minutes, or smaller increments thereof.

Supine time percentage defines the minimum percentage of data points required during the supine time in order for the first condition listed above to be met. Supine time percentage is programmable to a certain percentage by the user. In one embodiment, supine time percentage is set to 50 percent. In another embodiment, supine time percentage is set to 70 percent. In another embodiment, supine time percentage is set to 90 percent, or smaller increments thereof.

Figure 9:
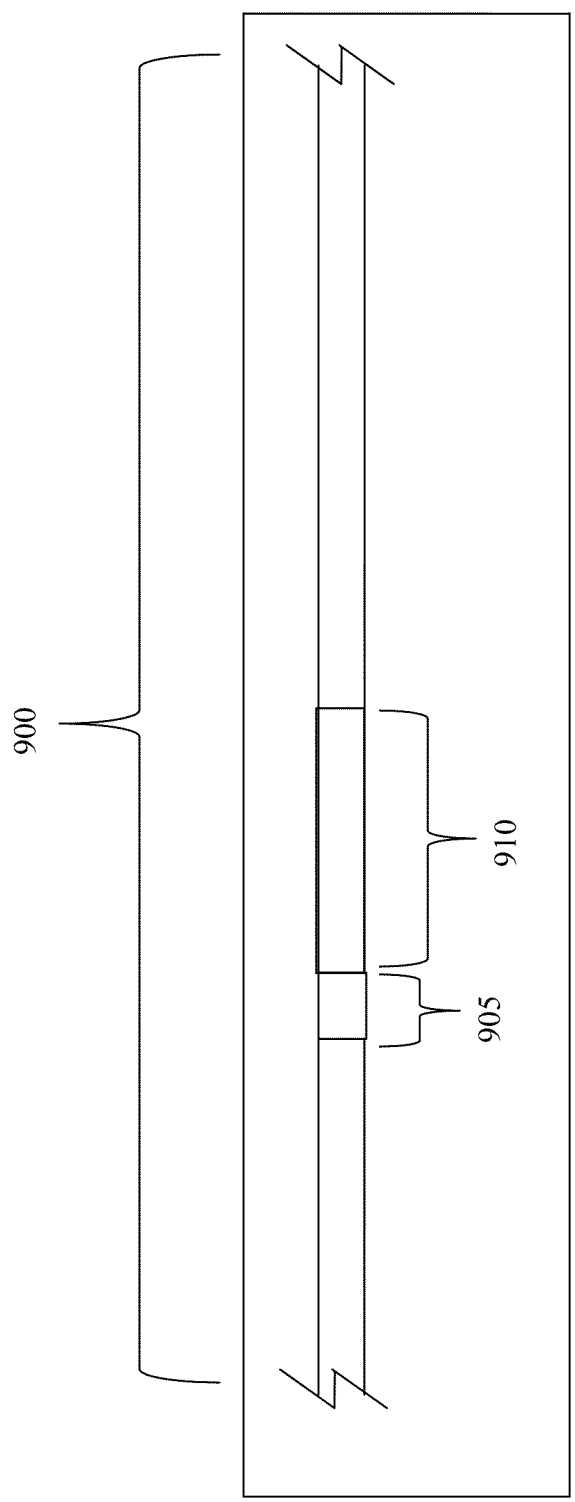
FIG. 9 is an illustration of a timeline depicting a stimulation session followed by a supine refractory time period.

Supine refractory time defines the minimal amount of time required to have passed from the end of the last stimulation session (scheduled, manual, or supine stimulation) before a new stimulation session may be initiated via the supine stimulation mode. Supine refractory time is programmable to a certain time period by the user. In one embodiment, supine refractory time is set to 30 minutes. In another embodiment, supine refractory time is set to 60 minutes. In another embodiment, supine refractory time is set to 120 minutes. In yet another embodiment, supine refractory time is set to 180 minutes. FIG. 9 is an illustration of a timeline 900 depicting a stimulation session 905 followed by a supine refractory time period 910. The supine refractory time period 910 begins immediately after the end of the stimulation session 905 and continues through its pre-programmed duration. No additional stimulation initiated by the supine stimulation mode can begin until the supine refractory time period 910 has ended.

Supine level defines the level of inclination required to achieve a supine posture. Supine level is programmable to a range of degrees by the user. In one embodiment, where the supine level is measured relative to a horizontal body, supine level is set between 170 and 200 degrees. In another embodiment, supine level is set between 160 and 200 degrees. In another embodiment, supine level is set between 150 and 200 degrees. In yet another embodiment, supine level is set between 140 and 200 degrees. In another embodiment, where the supine level is measured relative to a vertical baseline, supine level is set to an angle of 50, 60, 70, or 80 degrees, where 0 degrees is a vertical position and 90 degrees is a horizontal position.

Figure 10:
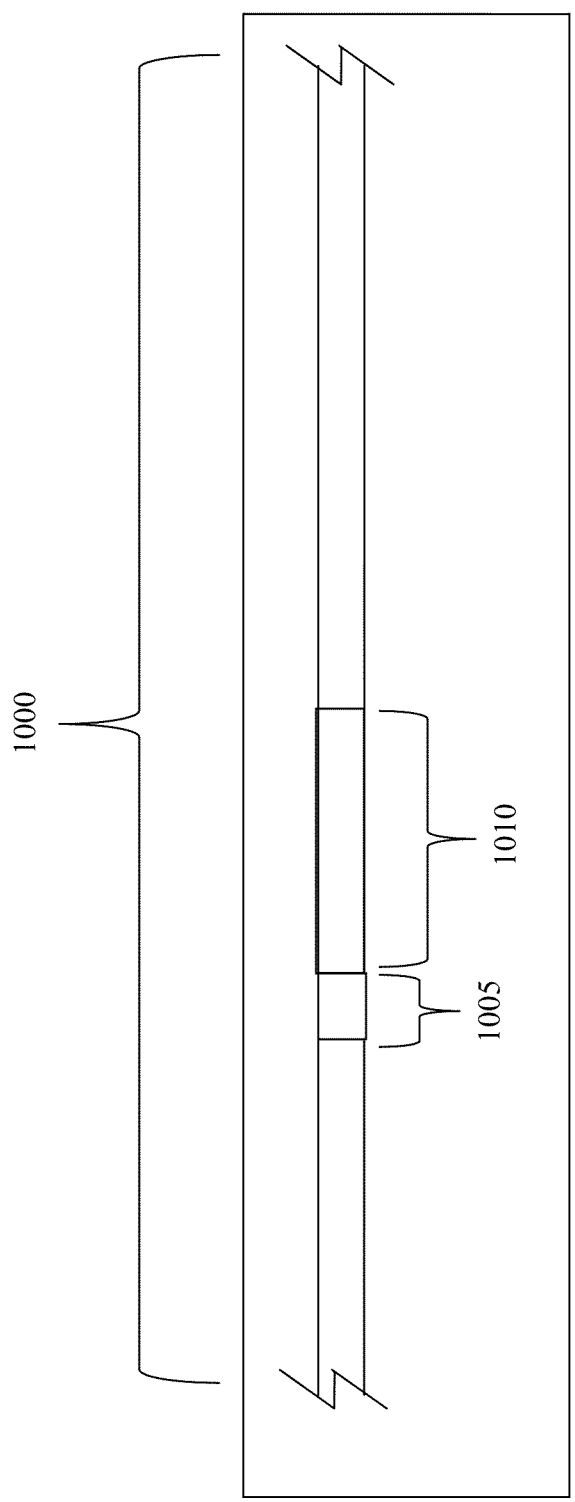
FIG. 10 is an illustration of a timeline depicting a stimulation session triggered by supine stimulation mode followed by a supine cancel period.

Supine cancel defines the maximum amount of time that can elapse between the end of a stimulation therapy session triggered by supine stimulation mode and the start of a regularly scheduled stimulation therapy session that will cancel the regularly scheduled stimulation therapy session. Supine cancel is programmable to a certain time period by the user. In one embodiment, supine cancel is set to 30 minutes. In another embodiment, supine cancel is set to 60 minutes. In another embodiment, supine cancel is set to 120 minutes. In yet another embodiment, supine cancel is set to 240 minutes. FIG. 10 is an illustration of a timeline 1000 depicting a stimulation session 1005 triggered by supine stimulation mode followed by a supine cancel period 1010. The supine cancel period 1010 begins immediately after the end of the supine stimulation mode stimulation session 1005 and continues through its pre-programmed duration. Any regularly scheduled stimulation session scheduled during the supine cancel period 1010 will not be initiated.

Supine retrigger defines the maximum amount of time that may elapse between the end of a stimulation therapy session triggered by supine stimulation mode and the initiation of another stimulation. In one embodiment, the supine retrigger period is programmable and may have a value of 2 4, 6, or 8 hours, or any increment therein. In another embodiment, after a predefined threshold, such as 75%, of a supine retrigger period has passed, the stimulator initiates a post-sleeping stimulation, in anticipation of a breakfast meal event, if a vertical position is sensed. In another embodiment, the stimulator does not initiate a post-sleeping stimulation if a vertical position is sensed if less than a predefined threshold, such as 75%, of a supine retrigger period has passed. It should be appreciated that an automatically set post-sleeping stimulation is optional and that stimulation may simply be preset for a particular time of the day.

Modifications to Prevent Habituation or Fatigue

Stimulation parameters may also be periodically modified, in accordance with a predefined schedule or dynamically by real-time physician or patient control, to reduce, avoid, or prevent the occurrence of muscle fatigue, habituation, and/or tolerance. Manipulation of the length of the "on" and "off" cycles can be performed while still obtaining the desired level of LES function. In one embodiment, the length of stimulation time to achieve the therapeutic goal can be decreased while the stimulation off time required for LES function to return to baseline can be increased. Less time spent in the "on" cycle will result in fewer incidents of muscle fatigue.

In another embodiment, the "on" and "off" cycles, as described previously, can cycle rapidly. For example, during a 30 minute period, the stimulation may be on for 3 seconds and off for 2 seconds during the entire 30 minute period.

In another embodiment, the patient can take a "stimulation holiday". In other words, stimulation can be further stopped for a time period greater than the "off" cycle to allow the muscle to recover. Greatly increasing the time period in which there is no stimulation also serves to avoid muscle fatigue and tolerance.

In another embodiment, stimulation parameters can be intermixed in an attempt to avoid muscle fatigue, habituation, and/or tolerance while still obtaining the desired level of LES function. For example, alternating short pulses can be intermixed with intermediate pulses to stimulate the LES. The variation in stimuli received by the muscle will assist in avoiding fatigue and tolerance.

In another embodiment, LES function can be normalized using the present invention without raising LES pressure above the mid-normal range. This is achieved by minimizing the energy delivered to the muscle to, but not beyond, the point where the LES regains normal function. Less energy delivered results in less fatigue and tolerance.

In another embodiment, the stimulation parameters can be changed, such as by modifying pulse width, frequency, amplitude, ramp rate, or the duty cycle, on a predefined periodic basis to avoid having the muscles habituate to a known and repeated stimulation setting. In such an embodiment, a stimulator may locally store a plurality of different stimulation parameters which are implemented in accordance with a predefined schedule. The stimulator may also store a single set of stimulation parameters, each parameter having an acceptable range of operation, and then randomly implement a stimulation parameter bounded by the acceptable ranges of operation.

Figure 11:
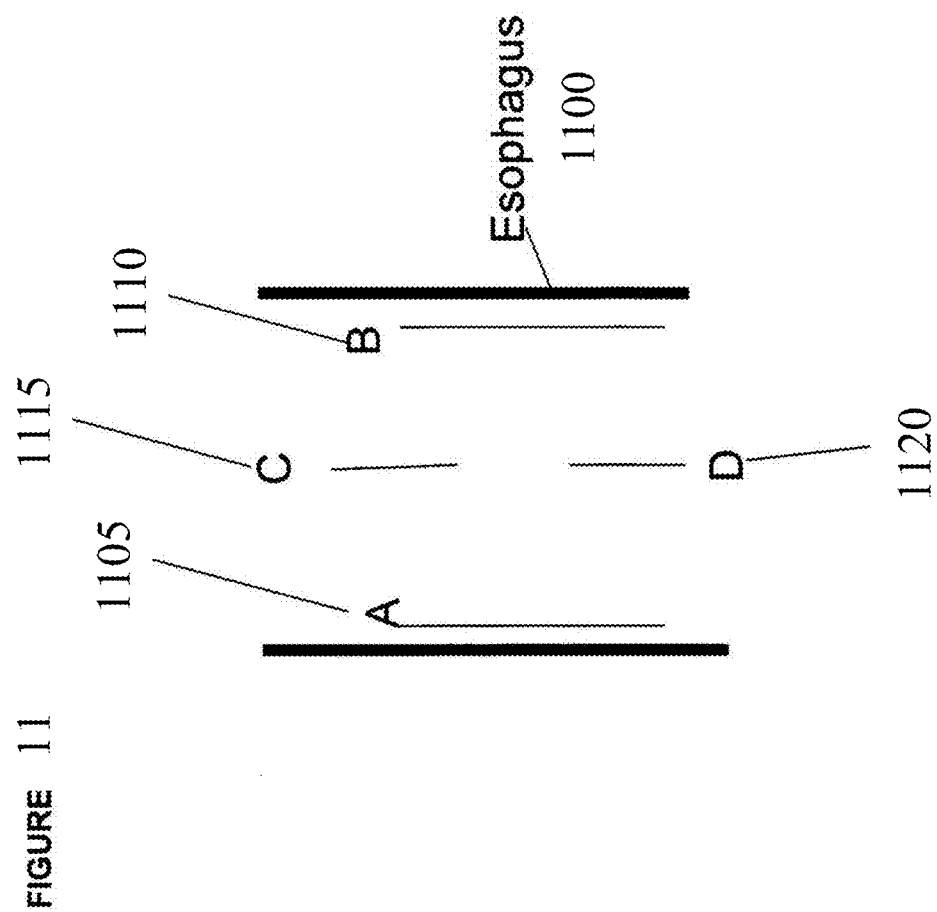
FIG. 11 depicts one exemplary electrode configuration in the esophagus of a patient.

Electrode Configurations and Methods of Placing and Confirming the Placement of Electrodes In one embodiment, the therapeutic objectives described herein are achieved by at least one of a plurality of different electrode configurations, as shown in FIG. 11. It should be appreciated that, in one embodiment, the electrode placement, as shown, at least partly enables the patient's LES function to normalize, post-stimulation, and/or the patient's LES pressure to increase post-stimulation. The electrode configurations described herein may be used in accordance with any of the stimulation parameters, system architectures, and sensing systems described herein.

Within the esophagus 1100, and more particularly the LES, a plurality of different electrode combinations can be used to achieve the therapeutic and operational objectives described herein. In one embodiment, a first electrode 1105 is placed proximate to the left lateral wall of the esophagus 1100 and operated in combination with a second electrode placed proximate to the right lateral wall 1110 of the esophagus 1100. In one embodiment, a first electrode 1105 is placed proximate to the left lateral wall of the esophagus 1100 and operated in combination with a second electrode placed in the anterior proximal wall 1115 of the esophagus 1100. In one embodiment, a first electrode 1110 is placed proximate to the right lateral wall of the esophagus 1100 and operated in combination with a second electrode placed in the anterior proximal wall 1115 of the esophagus 1100. In another embodiment, a first electrode 1105 is placed proximate to the left lateral wall of the esophagus 1100 and operated in combination with a second electrode placed in the anterior, distal wall 1120 of the esophagus 1100. In one embodiment, a first electrode 1110 is placed proximate to the right lateral wall of the esophagus 1100 and operated in combination with a second electrode placed in the anterior, distal wall 1120 of the esophagus 1100. In another embodiment, a first electrode 1115 and a second electrode 1120 are placed proximally and distally in the anterior wall of the esophagus 1100. In another embodiment, more than one of the above described combinations are used serially along the length of the esophagus 1100.

Figure 12:
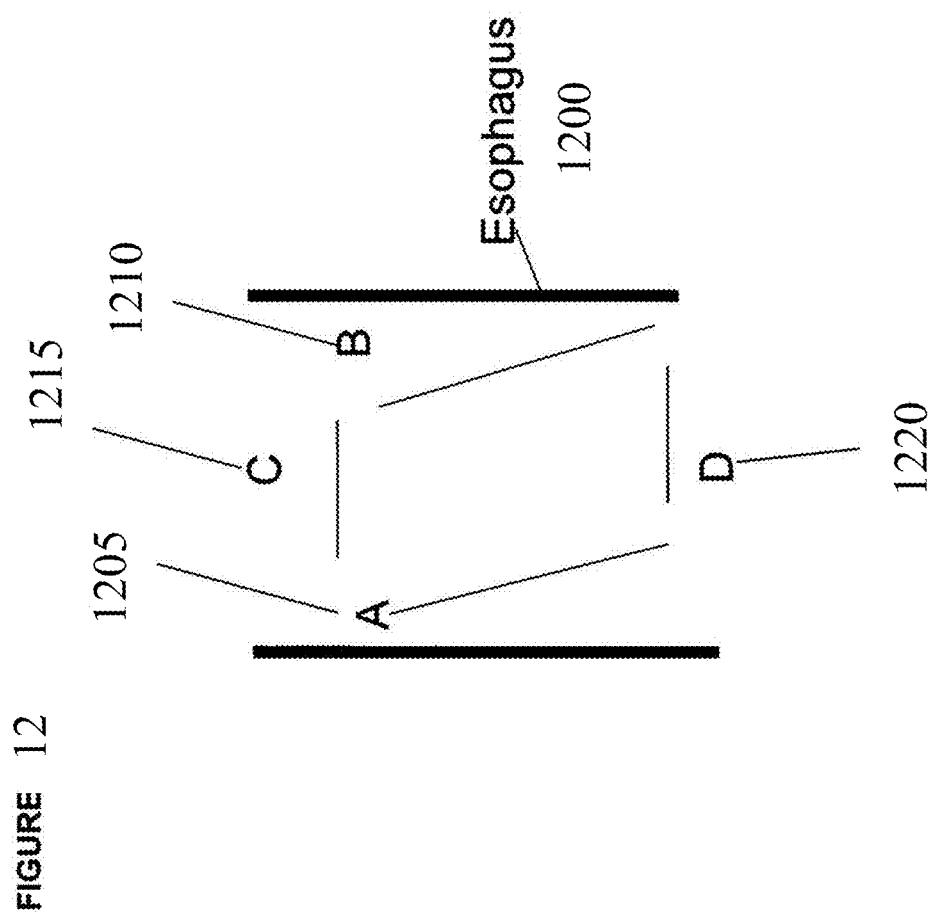
FIG. 12 depicts another exemplary electrode configuration in the esophagus of a patient.

Referring to FIG. 12, the electrodes 1205, 1210, 1215, 1220 can be placed longitudinally or transversely or in any orientation relative to the length of the esophagus 1200 and can be implemented in the same exemplary combinations described in relation to FIG. 11. It should be appreciated that not all of the electrodes shown in FIG. 11 need to be implanted or operated concurrently. For example, to achieve any of the aforementioned therapeutic objectives, only one pair of electrodes, such as 1105 and 1110 or 1115 and 1120 need be implanted and/or operated concurrently.

Figure 13:
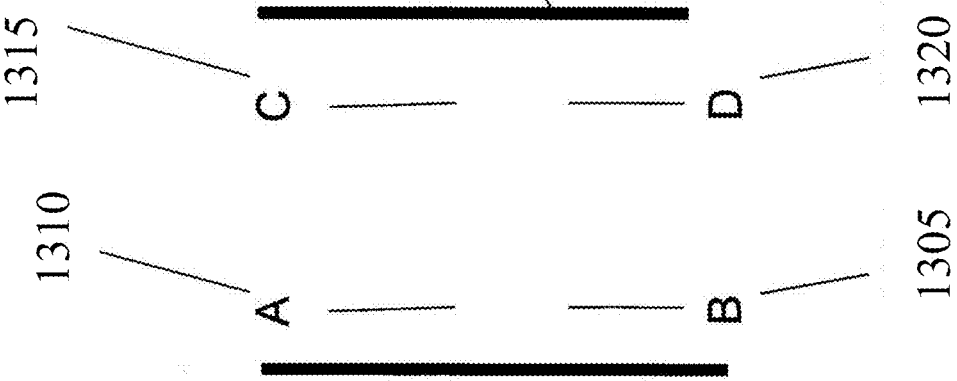
FIG. 13 depicts another exemplary electrode configuration in the esophagus of a patient.

In another embodiment, shown in FIG. 13, electrodes can be implanted in series with two electrodes 1310, 1305 proximate to the left lateral wall of the esophagus 1300 and two electrodes 1315, 1320 proximate to the right lateral wall of the esophagus 1300. These electrodes can be activated in various combinations, as described above, to provide for the optimal normalization of LES pressure, with minimal energy delivered to the tissue and minimal muscle fatigue or depletion of neurotransmitter storages. It should be appreciated that stimulation parameters (amplitude, timing of stimulation session and switching of electrode configuration) will be set so as to activate release of appropriate neurotransmitter. Such parameters can vary between patients due to surgical variation and physiological sensitivity. The electrode activation or implantation combinations can include electrodes 1310 and 1315, electrodes 1310 and 1305, electrodes 1315 or 1320, electrodes 1310/1315 alternating with 1305/1320, and electrodes 1310/1305 alternating with 1315/1320.

It should be appreciated that the length and surface area of the electrode and the distance between the electrodes can affect the degree and duration of the patient's post-stimulation normalization of LES function. It should further be appreciated that the length and surface area of the electrode can affect the current amplitude required to increase LES pressure post-stimulation.

In one embodiment, a patient is treated to achieve any one of the aforementioned therapeutic objectives by implanting the electrodes in a "linear" configuration. This is accomplished by implanting a first electrode axially along the length of the smooth muscle of the LES, shown as 1115 in FIG. 11, and implanting a second electrode 1120 below and substantially in alignment with the first electrode 1115. The bottom of the first electrode 1115 is separated from the top of the second electrode 1120 by a distance of no greater than 5 cm, preferably no greater than 2 cm, and most preferably approximately 1 cm. Each electrode is placed preferably more than 1 mm away from the vagal trunk. This electrode configuration is supplied a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec and a pulse repetition frequency of 20 Hz. A stimulator may further be configured to detect any of the aforementioned biological parameters, including LES pressure. In one embodiment, the LES pressure is derived from a sensor adapted to generate an impedance measurement. In one embodiment, LES pressure is derived from piezoelectric sensors or electrical activity based sensors.

In one embodiment, a patient is treated to achieve any one of the aforementioned therapeutic objectives by implanting the electrodes in a "parallel" configuration. This is accomplished by implanting a first electrode axially along the length of the smooth muscle of the LES, shown as 1105 in FIG. 11, and implanting a second electrode 1110 axially on the other side of the esophagus 1100, parallel to the first electrode 1105. The distance between the first electrode 1105 and the second electrode 1110 is less than half the circumference of the LES. The electrodes 1105, 1110 are implanted in the anterior of the LES, with preferably at least one electrode being in the right anterior (this places the stimulation as far as possible from the heart). Each electrode is placed preferably more than 1 mm away from the vagal trunk. This electrode configuration is supplied a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec. A stimulator may further be configured to detect any of the aforementioned biological parameters, including LES pressure. In one embodiment, the LES pressure is derived from a sensor adapted to generate an impedance measurement. In one embodiment, LES pressure is derived from piezoelectric sensors or electrical activity based sensors.

In one embodiment, a patient is treated to achieve any one of the aforementioned therapeutic objectives by implanting a first electrode transaxially across the length of the smooth muscle of the LES, shown as 1215 in FIG. 12, and implanting a second electrode 1220 substantially parallel to the first electrode and spaced apart from the first electrode 1215 a distance of no greater than 5 cm. This electrode configuration is supplied a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec. A stimulator may further be configured to detect any of the aforementioned biological parameters, including LES pressure. In one embodiment, the LES pressure is derived from a sensor adapted to generate an impedance measurement. In one embodiment, LES pressure is derived from piezoelectric sensors or electrical activity based sensors.

In one embodiment, a patient is treated to achieve any one of the aforementioned therapeutic objectives by implanting a first electrode and a second electrode in a configuration that concentrates current density at two or fewer points close to each electrode. This electrode configuration is supplied a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec.

In one embodiment, a patient is treated to achieve any one of the aforementioned therapeutic objectives by implanting a first electrode and a second electrode in a configuration that avoids distributing substantially all of the current density along the lengths of each electrode. This electrode configuration is supplied a stimulation pulse from a stimulator. The stimulation pulse may be delivered in accordance with any of the aforementioned stimulation parameters. In one embodiment, the stimulation pulse has a pulse amplitude no greater than 15 mAmp and more preferably no greater than 8 mAmp. In one embodiment, the stimulation pulse has a pulse width of approximately 200 μsec.

Variations in the stimulation and placement of electrodes also convey the added benefit of avoiding muscle fatigue and tolerance, as previously discussed. For example, as shown in FIG. 12, two pairs of electrodes, 1205/1210 and 1215/1220, can be implanted and stimulated in alternative succession. In one embodiment, the two pairs of electrodes receive simultaneous stimulations with the same stimulation parameters. In another embodiment, the two pairs of electrodes receive sequential stimulations with the same stimulation parameters. In another embodiment, the two pairs of electrodes receive simultaneous stimulations with different stimulation parameters. In another embodiment, the two pairs of electrodes receive sequential stimulations with different stimulation patterns. Electrode placement can also be manipulated to decrease muscle fatigue and tolerance. In one embodiment, the two pairs of electrodes are placed so that the distance between any set of electrodes is less than 2× the distance between the pair of electrodes, resulting in the stimulation from a set of electrodes stimulating less than 100% of the LES.

Preferably, during the implantation process, electrode configurations are tested to verify that the proper configuration has been achieved. In one embodiment, a catheter or endoscope configured to measure LES pressure in combination with a manometer is proximate to the implantation area while the newly implanted electrodes are stimulated. LES pressure is measured before, during, and/or after stimulation. If the desired LES pressure profile is achieved, the implantation is deemed successful and the testing may terminate. If the desired LES pressure profile is not achieved, the electrode configuration may be modified. LES pressure testing is then repeated until the proper LES pressure profile is achieved. Other sensed data, such as temperature, may also be used in this testing process. It should be appreciated that the testing process can be conducted separate from the implantation procedure. For example, patients can be tested with temporary electrodes, inserted non-invasively (nasogastric, for example), and upon success can be deemed suitable for implant.

Stimulator Energy Storage and Sensing Systems
Non-Sensing Active Implantable Medical Devices The embodiments disclosed herein achieve one or more of the above listed therapeutic objectives using stimulation systems that are energy efficient and do not require sensing systems to identify wet swallows, bolus propagation, or patient symptom changes, thereby enabling a less complex, smaller stimulation device which can more readily be implanted using endoscopic, laparoscopic or stereotactic techniques. The disclosed stimulation methods permit a natural wet or bolus swallow to override the electrically induced stimulation effect, thereby allowing for a natural wet or bolus swallow without having to change, terminate, or modify the stimulation parameters.

It should be appreciated that, in one embodiment, the stimulation device receives energy from a remote energy source that is wirelessly transmitting ultrasound or RF based energy to the stimulation device, which comprises receivers capable of receiving the energy and directing the energy toward stimulating one or more electrodes. It should further be appreciated that the device may be voltage driven or current driven, depending upon the chosen embodiment.

It should be appreciated that, in another embodiment, the stimulation device is a macrostimulator that receives energy from a local energy source, such as a battery, and directs the energy toward stimulating one or more electrodes. It should further be appreciated that the device may be voltage driven or current driven, depending upon the chosen embodiment.

By not requiring sensing systems that identify wet swallows, bolus propagation, or patient symptom changes, at least certain embodiments can operate with increased reliability and also be smaller in size. The smaller device size results in increased patient comfort, allows for placement (implantation) in the patient in more appropriate and/or convenient locations in the patient's anatomy, and allows the use of different surgical techniques for implantation (laparoscopic, endoscopic) and/or smaller incisions, which are less invasive, cause less trauma, cause less tissue damage, and have less risk of infection. The small size can also allow placement of a larger number of devices so as to provide redundancy, improved clinical efficacy, durability and reliability.

In addition to the absence of certain components which, conventionally, were required to be part of such an electrical stimulation system, embodiments of the present invention can achieve the above-listed therapeutic objectives using stimulation systems that operate at low energy level, such as at or below 20 Hz with a current of at or below 8 mAmp, preferably 3 mAmp, and a pulse width of 200 μsec.

As a result of the operative energy range, the following benefits can be achieved: a) a wider range of electrode designs, styles, or materials may be implemented, b) the need to use special protective coatings on electrodes, such as iridium oxide, or titanium nitride, while still maintaining electrode surface areas below 5 mm$^2$, is eliminated, c) one has the option of using small electrode surface areas, preferably below a predefined size with coatings to increase the effective surface area, such as iridium oxide, or titanium nitride, d) one can operate in wireless energy ranges that are within regulatory guidelines and safety limits and do not pose interference issues, such as a RF field strength below a predefined limit and ultrasound field strength below a predefined limit.

It should further be appreciated that the presently disclosed systems can be implemented using a variety of surgical techniques, including laparoscopic and endoscopic techniques. In one embodiment, a laparoscopically implanted device comprises a battery providing local energy storage and only optionally receives energy through wireless transfer, such as RF or ultrasound. In such an embodiment, the device stimulates at a higher amperage for shorter periods of time, relative to embodiments without local energy storage, thereby allowing for longer off cycles, lower duty cycles, and better battery efficiency. In one embodiment, an endoscopically implanted device may or may not comprise a local energy storage device but does comprise a wireless receiver to receive energy wirelessly transmitted from an external energy source and transmission device. In such an embodiment, this device stimulates at a lower energy setting for longer on cycles and shorter off cycles, relative to the embodiment with local energy storage, thereby having a greater duty cycle than a laparoscopic implant.

The stimulators of the present invention, when properly programmed in accordance with the stimulation parameters described herein and associated with the appropriate electrode configurations, exhibit a high degree of energy efficiency. In one embodiment, the electrical stimulation device initiates electrical stimulation based upon an internal clock or a patient activated trigger. Electrical stimulation then continues for a pre-set or predefined period of time. Referencing a 24 hour period of time, the preset or predefined period of time may be equal to an "on" time period that is less than or equal to 24 hours, 12 hours, 1 second, or any increment therein. Upon completion of that predefined period of time, the internal clock then causes the electrical stimulation device to terminate electrical stimulation.

It should be appreciated that any activation by an internal clock can be configured to cycle daily or a few times daily or be synchronized to meal times, as signaled manually by a patient. It should further be appreciated that the timing of meal times or other physiologically relevant events can be saved and/or learned, thereby enabling the device to default to standard initiation of stimulation time or termination of stimulation time based upon past data gathered. The setting of stimulation times may be set by a physician, based on an interview with a patient or based on the detection of eating using pH sensing or some other automated eating detection mechanism. In one embodiment, stimulation is initiated in advance of a predefined meal time to achieve an increase in LES tone before the patient eats. For example, if a patient's predefined meal time is 2 pm, then stimulation is set to initiate in advance of 2 pm, such as 1:30 pm. If the patient then reports symptoms between 4-6 pm, then, in the future, stimulation may be reinitiated at 3 pm. If a patient's predefined meal time is 12 pm, then set stimulation is set to initiate in advance of 12 pm, such as 11:30 am. If the patient then reports symptoms between 2-4 pm, stimulation may be reinitiated at 1 pm.

In another embodiment, the electrical stimulation device initiates electrical stimulation based upon an internal clock or a patient activated trigger. Electrical stimulation then continues for a pre-set or predefined period of time. Upon completion of that predefined period of time, the internal clock then causes the electrical stimulation device to terminate electrical stimulation. This ratio of the predefined period of stimulation relative to the time where electrical stimulation is terminated is less than 100%, up to a maximum duty cycle, such as 70%, 75%, 80%, 85%, 90%, 95%, or any increment therein.

In another embodiment, the electrical stimulation device initiates electrical stimulation based upon an internal clock or a patient activated trigger. Electrical stimulation then continues for a pre-set or predefined period of time. The pre-set or predefined period of time may be equal to a time period that is up to a maximum "on" period, such as 12 hours, during which the device may be continually operating. Upon completion of that predefined period of time, the internal clock then causes the electrical stimulation device to terminate electrical stimulation.

In another embodiment, the electrical stimulation device initiates electrical stimulation based upon an internal clock or a patient activated trigger. Electrical stimulation then continues for a pre-set or predefined period of time. The pre-set or predefined period of time may be equal to a time period that is up to a maximum "off" period, such as 12 hours, during which the device is not operating. Upon completion of that predefined period of time, the internal clock then causes the electrical stimulation device to restart electrical stimulation.

In another embodiment, the electrical stimulation device initiates electrical stimulation based upon an internal clock or a patient activated trigger. Electrical stimulation then continues for a pre-set or predefined period of time. The pre-set or predefined period of time may be equal to a time period that is less than the time required to see a visible change in the LES pressure. Upon completion of that predefined period of time, the internal clock then causes the electrical stimulation device to terminate electrical stimulation. The desired increase in LES pressure occurs post-stimulation, followed by a decrease in LES pressure which still remains above a pre-stimulation state after a period of >1 hour.

It should be appreciated that other stimulation protocols, which result in the desired effect of operating for less than 100% of duty cycle and which have a pre-set or predefined period of non-stimulation, can be achieved using combinations of turning on and off subsets of electrodes at different times. For example, one may turn a first subset of electrodes on, turn a second subset of electrodes on, then turn all electrodes off, followed by turning a second subset of electrodes on, turning a first subset of electrodes on, and then all electrodes off again.

Sensing Active Implantable Medical Devices

It should be appreciated that the present invention can be optionally operated in combination with sensing systems capable of sensing physiological events, such as eating, swallowing, a bolus propagating through the esophagus, muscle fatigue, pH level, esophageal pressure, tissue impedance, LES tone/pressure, patient position, sleep state, or awake state. In such a case, a physiological event can be used to modify the stimulation schedule by, for example, extending the stimulation time period based upon sensed pH level, eating, swallowing, or a bolus propagating through the esophagus or, for example, terminating the stimulation period before the preset time period expires based upon sensed muscle fatigue.

It should also be appreciated that the present invention can be driven by, and fully triggered by, sensing systems capable of sensing physiological events, such as eating, swallowing, a bolus propagating through the esophagus, muscle fatigue, pH level, esophageal pressure, tissue impedance, LES tone/pressure, patient position, sleep state, or awake state. In such a case, a physiological event can be used to initiate the stimulation schedule.

By operating the stimulation system less than 100% duty cycle and having the stimulation device be off during preselected periods, the presently disclosed stimulation system uses less energy than prior art devices. Accordingly, the stimulation systems disclosed herein can effectively operate to achieve the above-listed therapeutic objectives using an energy source local to the stimulator that a) does not include a battery, b) includes a small battery capable of being recharged from an external energy source, c) only includes a capacitor and, more specifically, a capacitor having a rating of less than 0.1 Farads or d) only includes a battery that is not rechargeable.

In one embodiment, a stimulator uses a remote data sensor for automatically adjusting parameters. The stimulator comprises stimulating circuitry contained within a housing that includes a power source, means for delivering stimulation, a receiver to collect data from a remote sensor and a control unit that analyzes the data received from the receiver and adjusts the stimulation parameters based on a plurality of stored programmatic instructions and the received data. The means for stimulation may include any form of leaded or a leadless device. The stimulator element would preferably be implanted either under the skin, in cases where the stimulator comprises a macrostimulator internal pulse generator (IPG), or close to the stimulation area, in cases where the stimulator comprises a microstimulator. The stimulator can also comprise a plurality of separate units, in separate housings, including, for example, an external control unit and receiver and an implantable stimulator, similar to a passive microstimulator.

The stimulator is in wireless or wired data communication with one or more sensor elements. The sensor elements are implanted in an area that allows the sensor to collect physiological data relevant to the controlling the operation of the stimulator. Each sensor element includes means for sensing the required physiological function and means for transmitting the data to the control unit. In one embodiment, the sensor element comprises a capsule adapted to measure physiological pH and transmit pH data from within the lumen of the esophagus to an implantable stimulator device. In another embodiment, the sensor element comprises a pH sensor located within a nasogastric tube and means for transmitting the pH data to an implanted control unit. In another embodiment, the stimulator comprises electrodes implanted in the LES that are wired to an implantable IPG, which is in data communication with a pH measuring element, such as but not limited to a pH capsule or a catheter based device, that is transmitting pH data to the device via uni-directional or bi-directional communication.

In another embodiment, the stimulator/sensing system disclosed herein can locally store a plurality of programmatic instructions that, when executed by circuitry within the IPG, uses data received from a capsule to automatically refine stimulation parameters within a pre-defined range of boundaries. The data may be continuously streamed from the sensing capsule to the IPG and may be subject to continuous monitoring and processing. The data may comprise any one of pH data, pressure data, LES pressure data, temperature, impedance, incline, or other physiological data.

Figure 14:
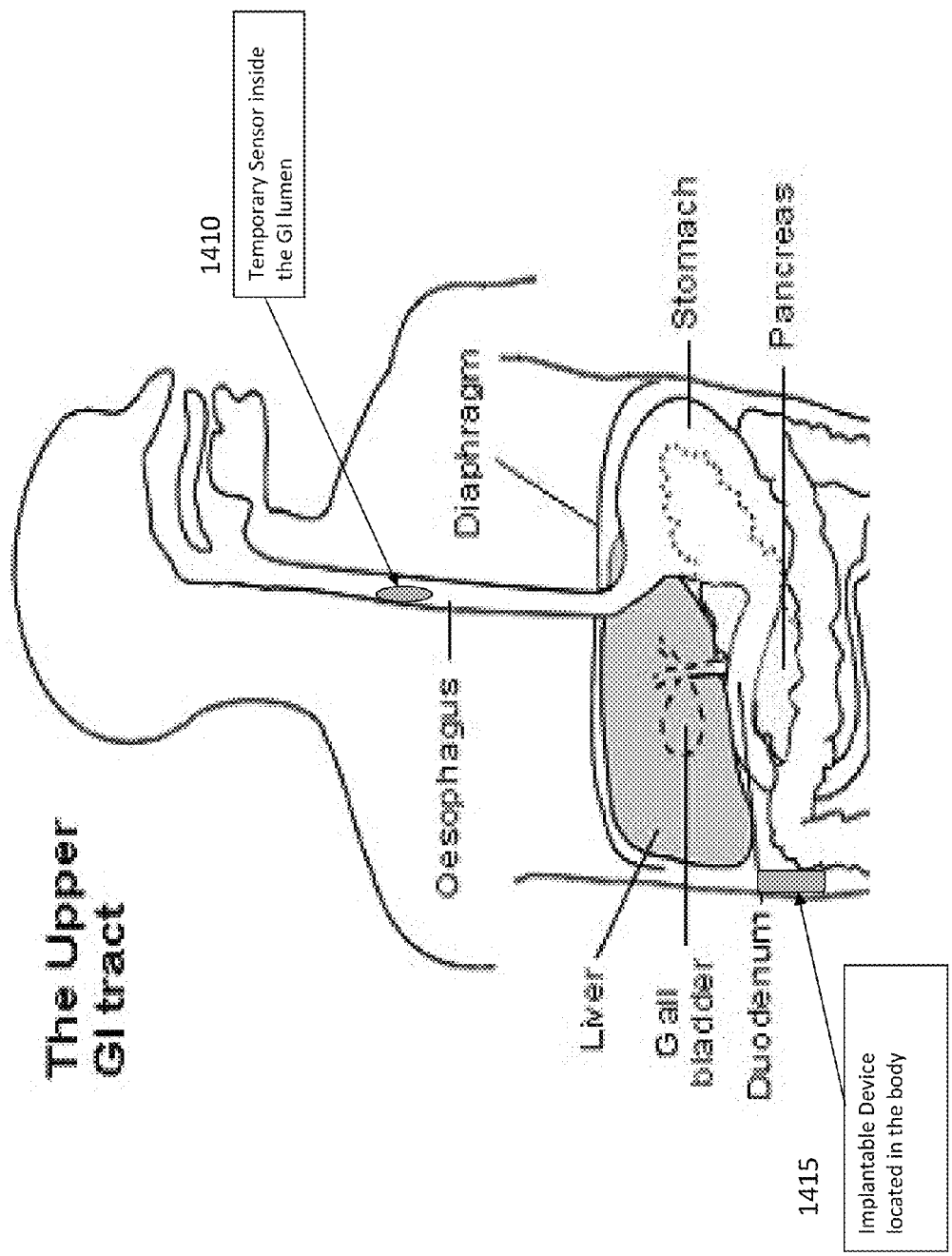
FIG. 14 is a cross-sectional illustration of the upper gastrointestinal tract showing a pH sensing capsule in the esophagus and a stimulator adapted to be implanted within the tissue of the patient.

Referring to FIG. 14, a patient 1400 has implanted within his tissue a stimulator 1415, as further described below. The stimulator 1415 is adapted to dynamically communicate with a temporary sensor 1410, as further described below, which may be located inside the patient's GI lumen. The implanted stimulator 1415 comprises stimulator circuitry and memory having programmatic instructions that, when executed, perform the following functions: transmit an interrogating signal designed to elicit or cause a transmission of sensed data from the temporary sensor 1410 or receive a transmitted signal comprising sensed data from the temporary sensor 1415 and process the sensed data to modify stimulation parameters, such as frequency, duration, amplitude, or timing. Optionally, the stimulator 1415 may also analyze the received sensed data signal to determine if the data is reliable. The implanted stimulator 1415 is adapted to only modify stimulation parameters or otherwise engage in a processing routine adapted to use the sensed data to determine how the simulation parameters should be modified when it senses and receives the sensed data. Optionally, the implanted stimulator 1415 is adapted to modify stimulation parameters or otherwise engage in a processing routine adapted to use the sensed data in combination with patient data inputted into an external device to determine how the simulation parameters should be modified.

For example, where a meal event, sleeping event, or other event which may cause, be related to, or be associated with a GERD event, is expected to occur at a specific time during the day (either because previously sensed data has determined a pattern indicating the existence of such an event or because patient data expressly indicates that such an event should be expected), stimulation parameters may be modified or otherwise established in order to provide the requisite level, degree or amount of stimulation before the anticipated event, such as 5 minutes, 10 minutes, 30 minutes, 45 minutes, 60 minutes, 90 minutes, 120 minutes, or some increment therein. The determination of stimulation parameters, including start time, end time, pulse frequency, duration, ramp rate, duty cycle, and/or amplitude, can be determined independent of the patient's immediate physiological state and not causally related to the patient's existing condition. Rather, historical data patterns from sensors, including pressure data, LES pressure data, temperature, impedance, incline, or other physiological data, can be used to define the GERD profile of a patient, namely when, in the course of a day, a patient is likely to experience a GERD event, and then used to proactively normalize LES function in advance of the GERD event. To properly generate and mine data patterns, it is preferable to capture both the magnitude of the physiological data (i.e. pH<4), the duration (for one hour), and the timing (around 1 pm). It is further preferable to associate different physiological data with each other to see if a predictive pattern may exist between data sets and to further correlate that data with the patient's own reporting of pain, discomfort, acid reflux, or other sensations to better determine when a GERD event is likely to occur in a day.

In one embodiment, the implanted stimulator 1415 is configured to check the reliability of the data by processing it to determine whether the data is indicative of the sensor being in an improper location. In one embodiment where the temporary sensor is a capsule measuring pH data intended to measure esophageal pH, such a determination process may be conducted by: a) monitoring the received pH data over a predefined period of time to determine if it is indicative of a high pH environment, such as the patient's stomach as opposed to the esophagus, b) monitoring the received data signal, such as an RF signal, over a predefined period of time to determine if the signal strength has significantly changed or modified, indicating a change in physical location, or c) monitoring a received accelerometer or inclinometer data signal from the pH capsule, over a predefined period of time, to determine if the capsule is in a proper physical orientation. Depending on the reliability check, the implanted stimulator 1415 may use, or discard, the sensed data. If no reliable data is received by the implanted stimulator 1415, it does not modify stimulation parameters or otherwise engage in a processing routine adapted to use the sensed data to determine how the simulation parameters should be modified. If reliable data is received by the implanted stimulator 1415, it modifies stimulation parameters or otherwise engages in a processing routine adapted to use the sensed data to determine how the simulation parameters should be modified.

The temporary sensor 1410 may store the sensed and transmitted data and transmit the stored data to an external reading device. It should be appreciated that the previously discussed methods for using sensed data, whether from a temporary sensor or permanently implanted sensor, may be performed by an external device. For example, an external device may wirelessly receive sensed data and use the sensed data to determine a pattern indicative of when a GERD event is likely to be experienced by a patient. Any pattern analysis method known to persons of ordinary skill in the art may be used. The data may include some or all of the sense data, externally inputted patient data, or a combination thereof. As discussed above, the external device would use the data to determine the time(s) of day when a patient typically experiences a GERD event and the appropriate stimulation parameters required to normalize LES function prior to such GERD event. The requisite stimulation parameters may be determined by examining historical GERD events in relation to stimulation parameters that had been implemented and modifying the stimulation parameters to increase or decrease the magnitude or duration of the stimulation accordingly. Additionally or alternatively, the implanted stimulator 1415 may store the sensed data and data indicative of how stimulation parameters, such as frequency, duration, amplitude, or timing, were modified based on the sensed data, and transmit the stored data to an external reading device.

Figure 15:
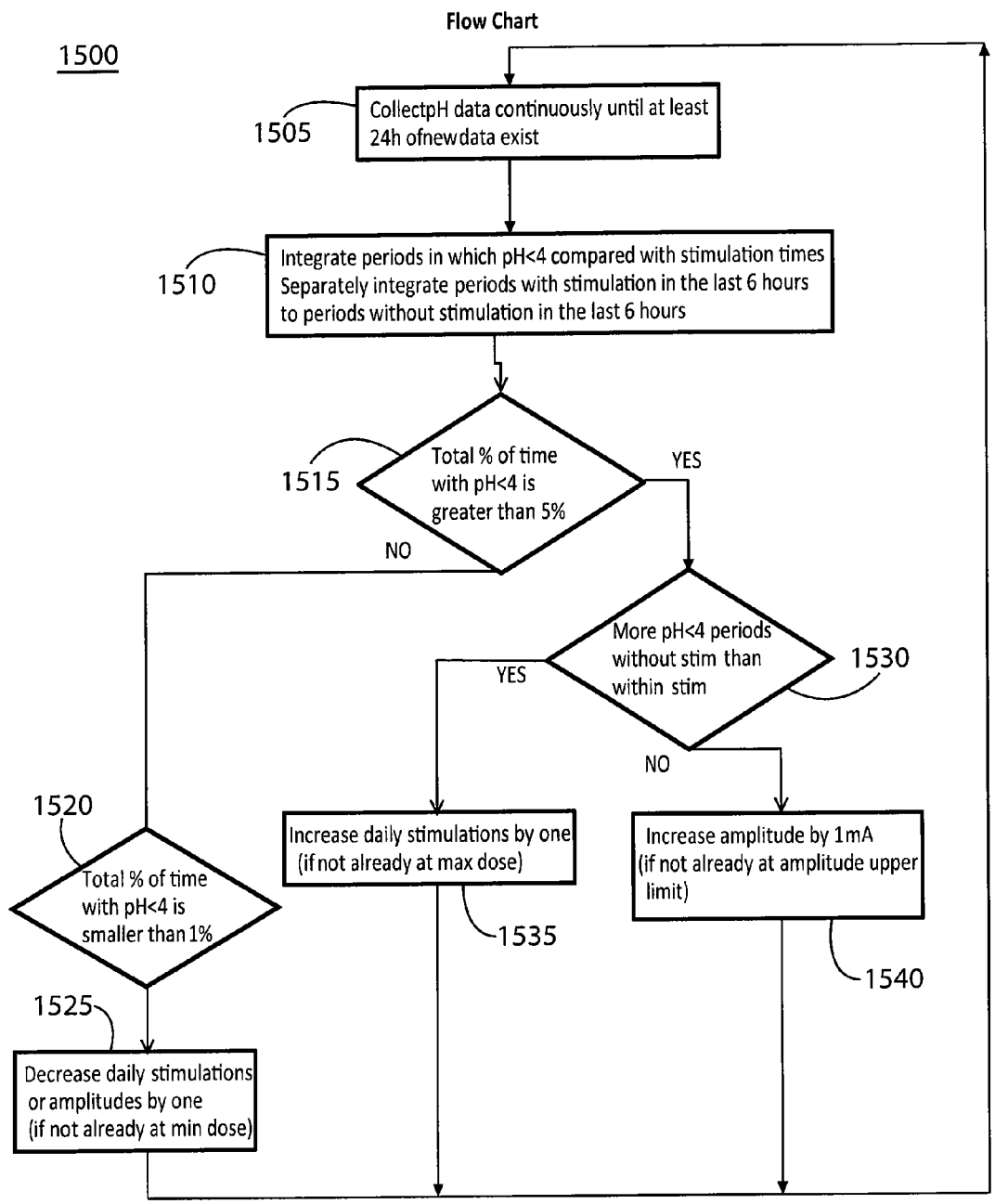
FIG. 15 is a flow sheet depicting a certain parameter setting method of one embodiment of the present invention.

Referring to FIG. 15, in one embodiment, the process 1500 implemented by the stimulator system comprises collecting 1505 pH data periodically or continuously over a predefined period, such as 1, 2, 6, 12, 24, 36, 48, or 60 hours, or any time increment in between. Circuitry within the stimulator analyzes the pH data 1510 to determine if, within the predefined period, such as 24 hours, pH is less than a predefined value, such as 4, for a percentage of time higher than a threshold value, such as 1, 2, 3, 4, 5, 10, 15, or 20 hours, or any increment therein 1515. The processor may analyze pH data 1510 by integrating periods in which the pH is less than the predefined value compared with stimulation times and separately integrate periods with stimulation in a most recent time period (i.e. last 6 hours) to periods without stimulation in the most recent time period.

If the percentage of time with the pH less than the predefined value within a predefined period is lower than a threshold value, such as 1 percent or lower 1520, then the circuitry may adjust stimulation parameters 1525 so as to reduce the timing, frequency, or size of the stimulation doses. In one embodiment, the circuitry decreases daily stimulations or amplitudes by a discrete amount, such as 1 mAmp. In one embodiment, the system may not reduce the timing, frequency, or size of the stimulation doses below a minimum dose.

If the percentage of time with the pH less than the predefined value within a predefined period is greater than a threshold value, such as 5 percent or higher 1515, then the circuitry may further analyze 1530 whether there were more periods with pH being greater than the threshold value during which there was no stimulation than with stimulation. If there were more periods with pH being greater than the threshold value during which there was no stimulation than with stimulation, the circuitry may increase the number of daily stimulations by a discrete amount, such as by 1 1535 or the duty cycle or length of a given stimulation session or duration by a discrete amount, such as 1 minute. By doing so, the system assumes the amount of energy delivered per stimulation is sufficient, but there simply were not enough stimulation events in a day, or the stimulation was not long enough. If there were more periods with pH being greater than the threshold value during which there was stimulation than with no stimulation, the circuitry increases the amplitudes of stimulations by a discrete amount, such as by 1 mAmp 1540. By doing so, the system assumes the amount of energy delivered per stimulation was not sufficient and therefore increases the energy delivered per stimulation. In one embodiment, the system may not increase the timing, frequency, or size of the stimulation doses above a maximum dose.

In general, if the percentage of time within a predefined period during which pH is less than a threshold value, such as 4, is higher than an upper value, such as 5%, then the stimulation parameters will be adjusted so as to increase dose. Also, if the percentage of time within a predefined period during which pH is less than a threshold value, such as 4, is lower than a lower value, such as 1%, then the stimulation parameters may be adjusted so as to reduce dose. The decreasing and increasing of dose will be done based on the temporal behavior of the pH values. It should be appreciated that doses may be incremented by any amount. It should further be appreciated that doses can be effectively decreased or increased by increasing one parameter while reducing another parameter so that the total energy is increased, reduced, or unchanged. Finally, it should be appreciated that all modifiable parameters will be bounded, on at least one of the maximum or minimum boundary, by a range defined by a healthcare provider.

In another embodiment, the operation of the system is augmented with other sensed data. Where the system is being used to stimulate the LES or treat GERD, pH sensor data can be augmented with accelerometer and/or inclinometer data. The accelerometer or inclinometer sensor(s) could be located within the implantable device or in another device on or inside the patient body. This additional data can enable the control unit algorithm to assess patient modes (e.g., sleep, exercise, etc) and thereby to improve the tuning of stimulation parameters for a specific patient, thereby improving device efficacy and/or efficiency. Additional sources of information may include, but not be limited to, pressure measurement or an impedance measurement by a capsule or an eating detection mechanism using one or more sources such as impedance or other electrical or electromechanical measurement from within the tissue or from the lumen. These additional sources of information can further be used by the control unit to adjust the stimulation dose and other parameters and other functions of the implantable device. It should be appreciated that any of the aforementioned data may be used individually or in combination to modify the operation of the system and, in particular, to determine how stimulation parameters should be modified to address an anticipated patient GERD event.

In another embodiment, the system logs the sensed and computed data and downloads the data to an external device for viewing and analyzing by a medical professional or a technician. By permitting on-demand or batch downloading, the system can eliminate the need for the patient to carry an external receiver during pH-sensing, thereby improving the use experience of the patient and potentially improving compliance and allowing for longer measurement periods. The system can download data automatically and without any requirement for user intervention, such as when an appropriately calibrated external device comes within a data communication area of the implanted device, or semi-automatically, such as when initiated by the implantable device when the implantable device is in proximity (communication distance) of the external device and the user has provided a password or other indication of approval via the external wireless interrogation device.

It should be appreciated that the external device receiving the sensed or computed data could be located at the healthcare provider's location or at the patient's home. If captured at the patient's home, the data could be automatically sent to the clinic for physician review and/or approval of suggested parameter changes via any communication medium, including Internet, Ethernet network, PSTN telephony, cellular, Bluetooth, 802.11, or other forms of wired or wireless communication. The transmitted data preferably contain the measured values, the recommended stimulation parameters adjustments, or both. Similarly, the physician approval, or physician suggested parameter changes, could be sent back to the external device located at the patient's home which, in turn, transmits appropriate commands to the implanted device, when the two devices are in proximity, to initiate the suggested parameter changes.

In another embodiment, the system monitors sensor, such as capsule, failure. If the sensor fails an internal diagnostic test, a failure or alert signal is transmitted to the implanted control unit, or the implanted control unit itself logs a failed attempt to communicate with, or obtain uncorrupted data from, the sensor. The control unit then transmits that failure or alert signal data to the external device and, in turn, to the healthcare provider, as described above, thereby alerting a healthcare provider that the patient needs to return to have the sensor fixed or another sensor implanted.

In another embodiment, the system is capable of recognizing and registering a plurality of different sensing devices, such as capsules, and re-initiate newly implanted sensors as required to ensure continuous or substantially continuous measurement. For example, the stimulator can be implanted for a long period of time, such as several months or years, and for a shorter period of time, such as once per annum, a sensor is implanted. The stimulator registers the new sensor and automatically adjusts the new sensor for operation in the particular anatomical region, such as the esophagus.

In addition to failing, sensors may migrate out of the implanted anatomical region. For example, where a sensor, such as a capsule, has been implanted into a patient's esophagus but has migrated to the stomach, the physical location of the sensor can be derived by examining the sensed data. For example, where a pH capsule has moved from the esophagus to the stomach, the capsule will likely transmit data indicative of extensively long periods during which the pH is highly acidic. In that case, the stimulator system can assume the capsule has migrated, report this failure to an external device, and ignore future data being transmitted from the capsule or record the data but not rely upon it for parameter setting. Similarly, the stimulation system may register a weaker or changed signal, indicative of a sensor moving a distance away from the recording device.

The presently disclosed stimulator system may further comprise a receiving antenna integrated into a stimulator system, which may be used for energy transfer to the stimulator system and communication to and from the device. The close proximity between the stimulator, particularly a miniature device, and a sensor, such as the pH capsule, can be used to achieve communication efficiency and increase durability through a miniature antenna in the stimulator that can accept data from the pH capsule. The close distance can effectively reduce power requirements and enables typical low frequency inductively coupled telemetry for transmission through titanium via coils; as well as high frequency RF communication such as MICS or IMS bands via monopole, dipole, or fractal electric field antennas. The communication distance can be further reduced by enabling anchoring of the pH capsule or nasogastric tube to the implanted control unit. This can be facilitated by, for example, a magnetic force between the two units caused by a magnet in both units or a magnet in one unit and a ferrous metal in the other.

One of ordinary skill in the art would appreciate that other means for communication can be used that will take advantage of the close proximity between the stimulating electrodes and the sensing device, such as a pH capsule, even when the control unit is farther away, thereby allowing for a significant reduction in the power consumption and improvement of reliability of communication. The stimulating electrodes in that embodiment would serve as receiving antennas and also simplify the design of the control unit, thereby avoiding the need for a receiving coil, antenna or other electromagnetic receiving means.

Bi-directional communication between the control unit and the sensor unit can be implemented as part of the system to allow, for example, calibration or activation of specific actions such as additional measurements, determination of measurements to be taken, determination of measurement times, local stimulation by the sensor unit, among other variables. The sensor unit can also be used to not only transmit the sensed data, but also to transmit energy for charging and powering the control unit and the stimulating device. For example, pH capsules that further acts as an energy recharging source can be periodically implanted, as required, to deliver energy to the control unit or a micro-stimulator in addition to actually sensing pH data.

Patient Selection Methods

In one embodiment, a person is permitted to practice the treatment systems and methods disclosed herein and, in particular, to have an embodiment of the electrical stimulation systems disclosed herein implanted into him or her only if the person passes a plurality of screening or filtering steps.

In one embodiment, a plurality of physiological measurements are taken of the patient and used to determine whether the patient may therapeutically benefit from the electrical stimulation treatment systems and methods disclosed herein. LES pressure data and/or pH data is collected from the patient. For example, pH measurements are obtained over a period of time, such as 4, 8, 12, 16, 20, or 24 hours or some increment therein. The amount of time within the predefined measurement period during which the pH measurement is above a predefined threshold indicative of acid exposure, such as a pH of 4, is calculated. The number of acid exposure events occurring for more than a predefined period of time, such as more than 1, 3, 10, 15, or 20 minutes, or any increment therein, is determined. The total time for each acid exposure event lasting more than the predefined period of time, i.e. 3 minutes, referred to as a long event, is then summed. If that total time exceeds a predefined threshold, such as 5 minutes to 240 minutes or any increment therein, it may be concluded that the patient would therapeutically benefit from the electrical stimulation treatment systems and methods disclosed herein. For example, if a patient has 4 events of acid exposure lasting 1, 4, 5 and 6 minutes and the predefined threshold is 3 minutes, the total time would be equal to 15 minutes (4+5+6). If the total time threshold is 10 minutes, then the patient can be categorized as an individual who would benefit from the electrical stimulation treatment systems and methods disclosed herein.

Another physiological measurement that may be used to select eligible patients is LES end expiratory pressure (LES-EEP). In one embodiment, a patient's LES-EEP is measured and collected during resting time, e.g. no swallow for at least 30 seconds, and then compared to at least one threshold. For example, the value of the LES-EEP should be below a normal value threshold, such as 10-20 mmHg, preferably 12-18 mmHg, and more preferably 15 mmHg, in order for the patient to qualify for treatment. In another embodiment, a patient's LES-EEP is measured and collected during resting time, e.g. no swallow for at least 30 seconds, and then compared to a range of pressure values, e.g. to two different threshold values. For example, the value of the LES-EEP should be above a lower threshold, which is indicative of the LES having some base functionality, such as 0 mmHg to 3 mmHg or any increment therein and below an upper threshold, such as 8 mmHg to 10 mmHg or any increment therein.

Another physiological measurement that may be used to select eligible patients is the rate of transient LES relaxation events (tLESr). Patients with higher rates of tLESrs which constitute a portion of their acid exposure time above a predefined threshold may benefit less from treatment than patients with lower rates of tLESrs constituting a portion of their acid exposure time above a predefined threshold. In one embodiment, a patient's tLESr rate is determined over a period of time, such as 24 hours or less. The tLESr rate is determined by recording the number and duration of acid exposure events, as described above, and then calculating the number of acid exposure events shorter than a predefined time period, such as shorter a total time threshold, as defined above, shorter than 5 minutes, shorter than 10 seconds or shorter than any increment therein, generally referred to as a short event. The number of such short events per period is then compared to an inclusion threshold, such as a range of 3-50, preferably 5-20. If the number of short events is below the range, the patient may not qualify for treatment or may qualify for a different stimulation regimen that can be programmed into the stimulator.

In another embodiment, a patient's acid exposure times are recorded and then compared to the timing of patient's reported reflux symptoms. The degree of temporal correlation between the acid exposure times and reported symptoms is then determined. Patients with a degree of correlation above a predefined threshold would be eligible for treatment while those below the predefined threshold would not be.

In another embodiment, it is determined whether a patient may therapeutically benefit from the electrical stimulation treatment systems and methods disclosed herein by temporarily stimulating the patient for a period of time, such as less than one week, using a non-permanent implanted stimulator to evaluate the patient's physiological response to stimulation and predict the patient's likely physiological response to a permanent stimulator. In one embodiment, the temporary stimulation is delivered using a temporary pacing lead endoscopically implanted in the patient's LES and connected to an external stimulator, which is either a non-portable system or a portable battery-operated device. The temporary stimulation system delivers periodic stimulations over a period of time, from 30 minutes to two weeks or more, during which the patient's symptoms, acid exposure events, and physiological response are recorded and correlations between the three are determined. The temporary stimulation data can then be used to determine the likely timings of GERD events and the required stimulation parameters to proactively normalize the patient's LES in advance of the GERD events, as previously discussed. Once the temporary stimulation period is complete, the electrode can be removed and a decision can be made regarding whether the patient would therapeutically benefit from a permanent implant based, for example, on the patient's physiological response to the temporary stimulation, improvement in symptoms, normalization of pH levels, and/or normalization of LES pressure.

In one embodiment, the temporary stimulator is in the shape of a small capsule-like device that is self-contained and includes all required components for stimulation including a power source or a receiver that allows power to be received wirelessly from outside the body and one or more electrodes. The device is adapted to stimulate the LES tissue. The device also includes an anchoring component, such as a hook, corkscrew, rivet, or any other such mechanism, which temporarily connects it to the LES wall. The capsule is implanted through an endoscopic or catheterization procedure to the LES wall. Such a capsule is expected to remain attached to the LES wall for a period of one day to two weeks or longer and then detach by itself and leave the body naturally. Further the device can include a sensor for detecting when it is attached to the wall, which will only stimulate when it detects that the device is still attached to the LES wall. Additionally the device may include wireless communication to allow telemetry and/or commands to be delivered from outside the body. The capsule can additionally include pH measurement, manometry measurement or other physiological measurement devices or sensors so that the short term efficacy of the stimulation can be more easily evaluated. Additional standard measurements can be made as needed for obtaining more information.

It should be appreciated that any form of temporary stimulator could be used. For example, a stimulator can include a) a plurality of implantable leads adapted to be temporarily implanted into the LES tissue through endoscopy, laparoscopy or other minimally invasive methods and further adapted to deliver stimulation to the LES, b) a housing which includes a control unit and circuitry for generating electrical stimulation where the housing is adapted to be temporarily implantable and/or be integrated with the leads such that the housing itself can deliver stimulation or externally located and wired to the leads without being implantable and/or c) an additional unit capable of recording the physiological data, stimulation data, and various patient inputs (symptoms, eating, sleeping events, etc.) and adapted to be used for turning stimulation on or off. Optionally, the additional unit is controlled by a physician and wirelessly programmable using a physician's computer system. Optionally, the stimulator can also be configured to include sensors or communicate with sensors that measure the aforementioned physiological measures.

Other approaches for selecting patients based on physiological data and/or temporary stimulation can also be implemented. It should be clear to person skilled in the art that the above selection methods could be integrated in various ways to result in an optimal selection of patients. For example one integrated method can be used to screen patients by qualifying candidates according to pH long events, the manometry value of LES-EEP, or the number of short events, or any combination thereof. Additionally, a combination of the measures can be used such as dividing the total length of long events by the rate of short events and comparing this value against a properly adjusted threshold, such that patients with a ratio above the threshold are included and others are excluded. Once qualified, the patient can undergo the permanent implant procedure or undergo the temporary stimulation process to further qualify the patient.

Physician Diagnostic and Programming Systems and Methods

Different patients may require different therapeutic regimens, depending upon implant depth, anatomical variations, treatment objectives, and severity of the disease condition. Each patient has a different resting lower esophageal sphincter (LES) pressure and different responses to stimulation (due to expected variability in sphincter muscle condition and also in the implant location). Furthermore, changes to the patient's anatomy, for example arising from normal healing after implantation, chronic stimulation or age, can also change the optimal stimulation dosage. Accordingly, it is preferred for a patient to first undergo a diagnostic process to determine whether, and to what extent, the patient can be treated by one of a plurality of therapeutic processes, as further described below. It is also preferred for a patient to periodically visit a physician to have the efficacy of the stimulation system checked, optimized, and possibly reprogrammed, as provided below.

In one embodiment, because the goal is to keep the sphincter at a pressure or function which eliminates or greatly reduces the chances for acid exposure, it is unnecessary for the muscle to always have high pressure but, rather, it is desirable to have (1) some average pressure sustained at all times with a certain permitted range of variability around it and a minimal pressure that the sphincter will never be, or will rarely be, below or (2) some average function sustained at all times with a certain permitted range of variability around it and a minimal function that the sphincter will never be, or will rarely be, below or a combination thereof. Continuous non-stop stimulation is not optimal because the acute response of enhanced pressure may diminish over time due to neuro-muscular tolerance or muscle fatigue. Furthermore, a simple "on-off" regime during which the muscle is stimulated for a first duration and then the stimulation is turned off for a second duration may be effective; however, different muscle properties, variations in the patient condition, and variations in the implant may require a different selection of the "on" and "off" periods for each patient and may also require a change in the initial selection of the "on" and "off" periods over time in the same patient.

In one embodiment, a patient's average pressure (AP) and minimal pressure (MP) is set by conducting a parameter setting test, in which a stimulator is controlled by an operator and a manometry measurement of LES pressure is made. During this test, the operator turns on the stimulation and then observes the LES pressure while keeping the stimulation on until the pressure crosses a first threshold, defined, for example, by AP+(AP-MP). When the observed pressure passes this first threshold, the stimulation is either turned off or kept on for an additional short period of up to 5 minutes and then turned off. The operator notes the time when the stimulation is turned off.

The operator continues to observe the pressure and once the pressure reaches MP, the operator turns on the stimulation again and notes the time. This measurement process continues for several hours, such as 2 to 5 hours, so that several stimulation on-off periods can be recorded. At the end of the test period, a chronic "on" time is selected to be the median of the measured "on" periods and a chronic "off" period is selected to be the median of the measured "off" periods. It should be appreciated that the initiation of stimulation, turning off of stimulation, recordation of time periods, and recordation of LES pressure can be performed automatically, based on a pre-programmed set of threshold values, by a computing device comprising a processor and memory storing the threshold and control instructions as a set of programmatic instructions.

In another embodiment, a patient's average pressure (AP) and minimal pressure (MP) is set by conducting a parameter setting test, in which a stimulator is controlled by an operator and a manometry measurement of LES pressure is made. During this test, the operator turns on the stimulation, notes the electrode impedance value, and then observes the LES pressure while keeping the stimulation on until the pressure crosses a first threshold, defined, for example, by AP+(AP-MP). When the observed pressure passes this first threshold, the stimulation is either turned off or kept on for an additional short period of up to 5 minutes and then turned off. The operator notes the time when the stimulation is turned off and the electrode impedance value when the stimulation is turned off.

The operator continues to observe the pressure and once the pressure reaches MP, the operator turns on the stimulation again and notes the time and electrode impedance value. This measurement process continues for several hours, such as 2 to 5 hours, so that several stimulation on-off periods can be recorded. Electrode impedance is measured every time the stimulation is turned "on" or "off". At the end of the test period, a chronic "on" time is selected to be the median of the measured impedance value for the "on" periods and a chronic "off" period is selected to be the median of the measured impedance value for the "off" periods. Rather than setting a stimulation device to operate based on fixed time periods, a stimulation device is programmed to turn off and on based upon the measured impedance values, where the device turns on when a patient's impedance value approaches the measured mean, median, or any other calculated impedance value for the on periods and turns off when a patient's impedance value approaches the measured median, mean, or any other calculated impedance value for the off periods. It should be appreciated that the initiation of stimulation, turning off of stimulation, recordation of time periods, recordation of electrode impedance, and recordation of LES pressure can be performed automatically, based on a pre-programmed set of threshold values, by a computing device comprising a processor and memory storing the threshold and control instructions as a set of programmatic instructions. It should be appreciated that, in addition to the above embodiments, a patient's LES pressure may be recorded by conducting a parameter setting test, in which a stimulator is controlled by an operator and a manometry measurement of LES pressure is made. The recorded LES pressures are compared to a predefined threshold to determine a maximum pressure which should preferably not be exceeded. The aforementioned on and off periods are then set or modified based on this maximum pressure data.

It should be appreciated that the use of impedance values is useful, relative to manometry measurements, if the values of the "on" and "off" periods in the acute phase do not converge to a small range within a few minutes. It should further be appreciated that other measurements, instead of impedance, can be used, including physical tension sensors (i.e. implantable strain gauge) or sensors of the muscle electrical activity or sensor of muscle pressure. Furthermore, it should be appreciated that both of the aforementioned tests can be used, and/or combined, to fix time windows for the "on" and "off" periods and rely on impedance measurements in order to adapt, modify, or change the time windows to account for a possible drift in muscle status In another embodiment, a doctor makes a determination regarding the LES electrical stimulation therapy (LES-EST) available to a patient by first engaging in a process for evaluating a plurality of appropriate dosing values for a patient. The evaluation process comprises subjecting a patient to a plurality of pulse sequences and measuring the corresponding LES pressure.

TABLE 4

| Phase # | Electrical Stimulation Type | Pulse Frequency | Pulse Duration | Pulse Amplitude |
|---|---|---|---|---|
| 1 | Short Pulse | 20 Hz | 200 μsec | 5 mAmp |
| 2 | Short Pulse | 20 Hz | 200 μsec | 3 mAmp |
| If #1 reaches ≥20 mmHg | | | | |
| 3 | Short Pulse | 20 Hz | 200 μsec | 7 mAmp |
| If #1 does not reach ≥20 mmHg | | | | |
| 4 | Short Pulse | 20 Hz | 200 μsec | 10-15 mAmp |
| If #3 does not reach ≥20 mmHg | | | | |
| 5 | Intermediate Pulse | 20 Hz | 3 ms | 3-15 mAmp using the same sequence as 1-4 |
| 6 | Optimal Pulse | 20 Hz | Optimal Pulse | Optimal amplitude |

As shown above, each of phases 1-4 is applied for 20-30 minutes with a 20-30 minute interval between sessions. The pulse increments can range from 0.1 mAmp to 15 mAmp. The pulse in Phase 6 is intermittently applied for 5 hours, during which stimulation is turned on until pressure is greater than or equal to 20 mmHg for at least 5 minutes (on period) and then turned off until pressure drops to less than 10 mmHg or patient's baseline whichever is higher (off period), and then turned on again until it is greater than or equal to 20 mmHg again (on period), repeating thereafter. These on-off sessions continue while the time durations are recorded. These recorded periods are then used to determine the optimal duty cycle for the patient during the treatment phase (patient-specific LESEST). It should be appreciated that, if a subject experiences pain or discomfort for any given stimulation sequence, the pulse amplitude is decreased in 1 mAmp increments until stimulation is tolerable. Once the effective tolerable setting is established, the patient-specific LES-EST is initiated with the defined stimulation parameters, as determined by the parameter setting stage described above. Preferably, the patient-specific LES-EST is checked at a set schedule (every 6 months or once a year) or when a patient starts reporting GERD symptoms using manometry and the patient-specific LESEST parameters are then modified to achieve ideal LES pressure.

It should be appreciated that the aforementioned diagnostic processes account for a plurality of variables that substantially affect treatment quality, treatment efficacy, and patient compliance, including, but not limited to, patient's disease condition and the corresponding stimulation energy level and frequency required to achieve a positive therapeutic effect, patient willingness to manually apply stimulation, and form factor of the stimulation source, among other variables.

The variables generated in the course of the diagnostic processes can be used to automatically program a controller, which may be used to control a stimulator. In one embodiment, a diagnostic terminal executing on a conventional computer generates at least one variable, such as stimulation pulse width, frequency, amplitude, ramp rate, or a duty cycle, that substantially affects treatment quality, treatment efficacy, and patient compliance, including, but not limited to, patient's disease condition and the corresponding stimulation energy level and frequency required to achieve a positive therapeutic effect, patient willingness to manually apply stimulation, and form factor of the stimulation source, among other variables. The diagnostic terminal is in data communication with a controller configuration terminal that electronically receives a controller into an interface or wirelessly communicates with the controller that is responsible for executing the stimulation parameters. Upon generating the variables, the diagnostic terminal transmits the variables, which are eventually received by the controller and saved in an appropriate memory location. The controller then uses the variables to control one or more stimulation settings.

In another embodiment, the stimulation parameters are checked by a physician using a data terminal, such as a laptop, tablet computer, mobile device, or personal computer. As discussed above, data relevant to the efficacy of the stimulation parameters can be wirelessly obtained from the stimulation device memory or from a patient controlled computing device, such as a tablet computer, laptop, personal computer, or mobile device. The physician can modify the stimulation parameters in accordance with the received data and, using the data terminal, issue modified stimulation parameters to the controller of a stimulator as described above.

Exemplary Therapies

The following description is intended to provide examples of how the therapies, described above, may be specifically implemented. They should not be viewed as limiting the general scope of the inventions described herein.

Therapy One: Patient Timed and Delivered Stimulation Using a Handheld Device

In a first therapy, a patient can be effectively therapeutically treated with intermittent wireless short bursts of stimulation applied a plurality of times during a day. For example, in one embodiment, a patient can be treated by applying a burst of stimulation for a period of five minutes or less at a frequency of 5 times or less per day. In another embodiment, the stimulation occurs less than 5 times a day for a period of 30 minutes or less per stimulation. This stimulation frequency is effective to treat certain symptoms of a patient, including diminishing or eliminating a patient's heartburn, regurgitation or both.

Figure 16:
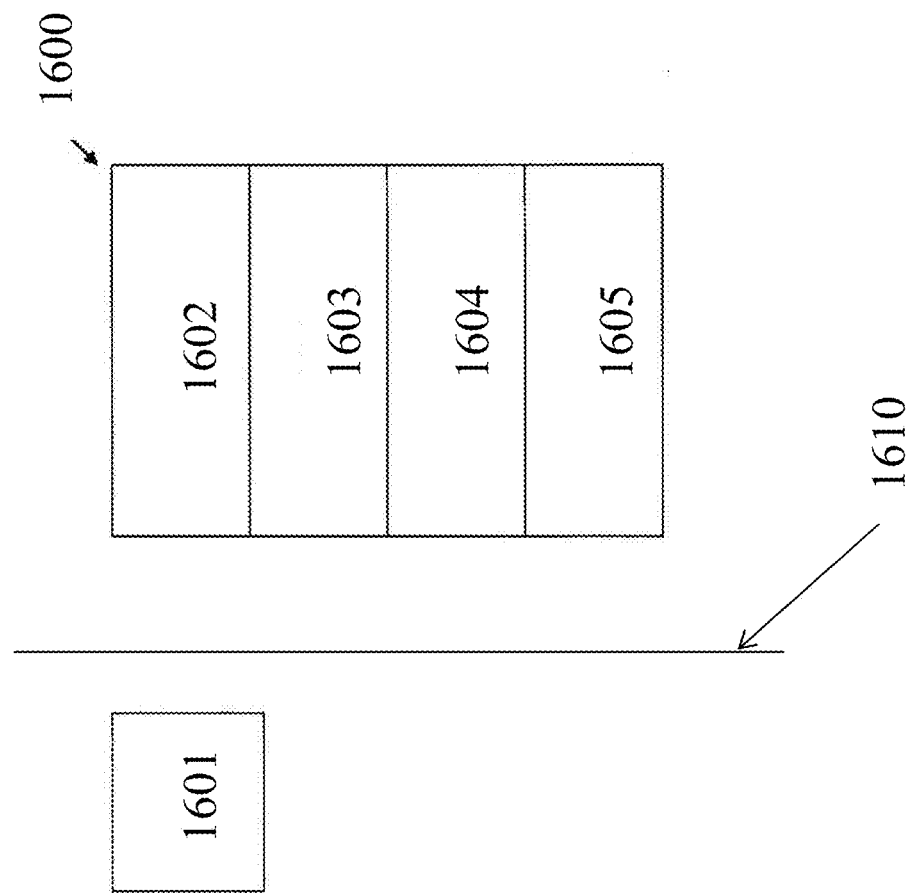
FIG. 16 is a first embodiment of a block diagram of certain modules of the present invention.

In this treatment method, a patient can be effectively treated by having the patient apply an external power source over a predefined area on the patient's body and manually initiate a stimulation. FIG. 16 is a first embodiment of a block diagram of certain modules of the present invention. In one embodiment, the stimulation system comprises a stimulation source 1600 and a microstimulator 1601. As shown in FIG. 16, the stimulation source 1600 comprises a controller 1602, transducer 1603, waveform generator 1604, and power source 1605, such as a battery. The stimulation source 1600 directs energy, such as ultrasound or RF energy, across the patient's skin 1610 and toward a microstimulator 1601 that is implanted directly on the site being stimulated. The stimulation source 1600 can generate a plurality of different pulse widths, amplitudes, frequencies, or combinations thereof, as further described below.

In certain situations, the device may require an energy supply to power the implantable pulse generator, but it is difficult or undesirable to include an implantable battery that would be wired to the device due to size limitations, restrictions arising from the implant location, or the need to decrease device costs. In one embodiment, a rechargeable battery is wired to the stimulator. The rechargeable battery stores a smaller amount of charge, and therefore can be small in size, but is configured or adapted to be replenished using wireless transmission of energy.

In another embodiment that requires an implanted device size which is even smaller than that which is possible with a rechargeable battery and associated recharging circuit, the device comprises a passive circuit that receives, in real time, transmitted wireless energy from a transmission source external to the patient. The implanted passive circuit would control the extraction of the transmitted energy and the delivery of the energy to the rest of the stimulator device. The external energy transmission device would control the timing of stimulation and any sensing and/or triggering mechanisms related thereto. One limitation to the wireless transmission of energy is the amount of energy that can be wirelessly transmitted in any given time due, for example, to safety or interference requirements. Such wireless energy transmission limitations narrow the applicable stimulation amplitude and waveform that can be applied to the tissue, thereby limiting the clinical application and benefit of such systems.

In another embodiment, the microstimulator comprises a means for storing a charge locally, such as a short-term energy storage component or a capacitor, and an associated trigger mechanism. During an on-off duty cycle for stimulating the microstimulator, the off-time of the stimulation duty cycle can be used to temporarily store a charge, thereby enhancing the maximal amplitude and variety of waveform that can be applied. The implanted device circuit is configured to control and time the stimulation in response to energy or control information from a controller that is external to the patient and communicates wirelessly with the implanted device. The implanted circuit extracts the transmitted energy or control information and, in response thereto, shapes the waveform within the off-time of each stimulation cycle using components such as capacitors, diodes, inductors, transistors and resistors.

The operating characteristics of a capacitor integrated with, or local to, the implanted device will be determined, at least in part, by the required pulse duration and the ratio of required stimulation pulse amplitude to minimal expected extracted supply current within the implantable device. The capacitor characteristics will also be a function of the load impedance. For example, assuming a required pulse duration of 200 μs to be applied every 50 ms and a required amplitude of 10 mAmp, the device will need to provide a charge of 2 μC (10 mAmp×200 μs). Assuming an impedance of 100 ohms with a voltage of 1 V (10 mAmp×100 ohm), then the minimum required capacitor will have a value as approximated by the following equation:

$$C=Q/V=2\ uC/1V=2\ uF$$

This value will need to be adjusted so that it is not fully discharged during stimulation and to compensate for losses within the implantable device. For an overall cycle of, for example, 50 ms the theoretical minimal extracted supply current that can drive the required pulse will be:

Minimal extracted current=10 mAmp×200 μs/(50 ms−200 μs)=0.04 mAmp

Adjusting for internal losses within the stimulator will yield a practical limit of about 0.1 mAmp or 100 μAmp. Higher available supply currents can allow for shorter cycles or longer pulse duration as necessary and can be extrapolated from the above.

In one embodiment, energy need not be stored between cycles and the passive circuit responds, in real-time, to the wireless transmission of energy. For example, the implanted circuit may initiate a stimulation pulse in response to a stimulation pulse wirelessly sent by the external energy transmitting unit, where the energy transmission is above a pre-defined time period, is characterized by the intermittent ceasing of energy transmission, or is characterized by another combination of "on"-"off" energy signals.

In one embodiment, the stimulation source 1600 directs ultrasonic energy to the microstimulator 1601 which comprises an ultrasonic receiver. The microstimulator 1601 is implanted into the area to be stimulated via an endoscope. The microstimulator 1601 can function either as a pass-through for energy and stimulation parameters or comprise an energy storage and programmatic memory to deliver short stimulation bursts, using the stored energy, at predetermined time intervals, pursuant to the programmed memory.

In one embodiment, the stimulation source 1600 directs radio frequency (RF) energy to the microstimulator 1601 which comprises an RF receiver. The microstimulator 1601 is implanted into the area to be stimulated via an endoscope. The microstimulator 1601 can function either as a pass-through for energy and stimulation parameters or comprise an energy storage and programmatic memory to deliver short stimulation bursts, using the stored energy, at predetermined time intervals, pursuant to the programmed memory.

In one embodiment, the stimulation source 1600 comprises a controller 1602, transducer 1603, waveform generator 1604, and power source 1605, such as a battery. Operationally, the controller 1602, via a processor in data communication with a memory storing programmatic instructions, causes the waveform generator 1604 to generate a predefined waveform, having an associated pulse width, amplitude, and frequency, which is transmitted via the transducer 1603 to the endoscopically implanted microstimulator 1601. A patient applies the stimulation source 1600 intermittently for a short time period, preferably 30 minutes or less, over the microstimulator 1601 site. Where the microstimulator 1601 comprises a local memory for storing programmatic instructions, in particular stimulation parameters and processes, the stimulation source 1600 need not comprise a controller and memory for storing such programmatic instructions and may simply transmit a predefined amount of energy to the micro stimulator.

Figure 17:
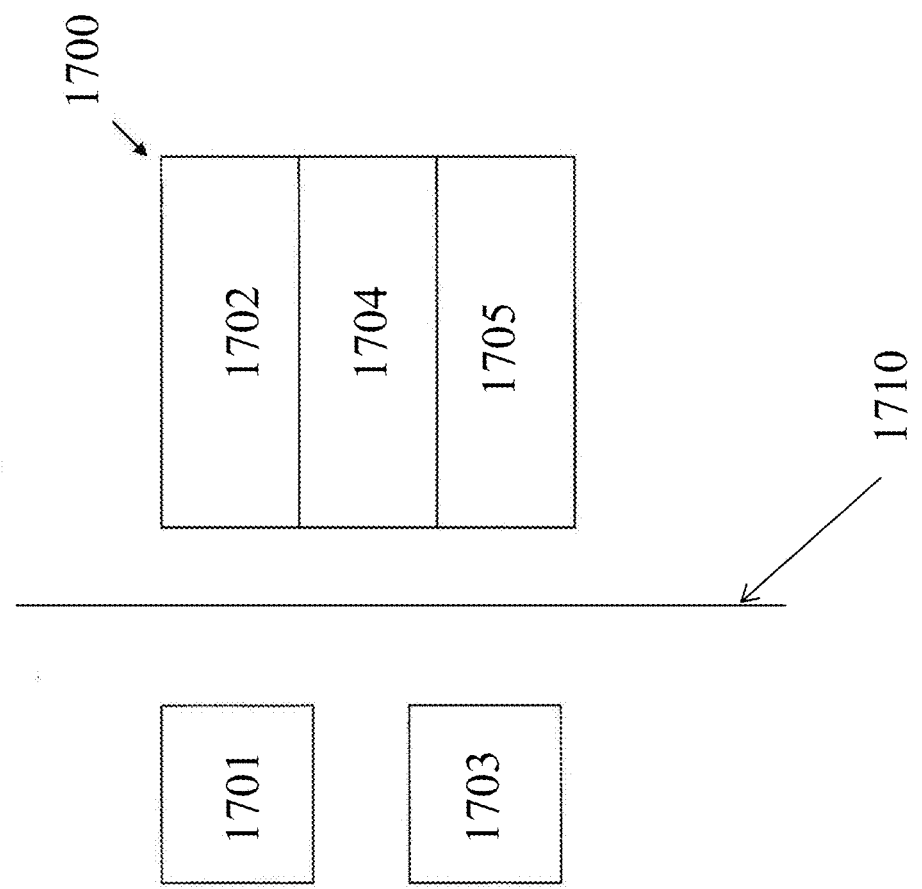
FIG. 17 is a second embodiment of a block diagram of certain modules of the present invention.

In another embodiment, referring to FIG. 17, the stimulation source 1700 comprises a controller 1702, waveform generator 1704, and power source 1705, such as a battery. It wirelessly communicates with, and/or transfers energy to, a transducer 1703 that is implanted subcutaneously. The subcutaneous transducer 1703 receives the wirelessly transmitted energy, such as RF or ultrasound, through the patient's skin surface and transmits it, via a wired or wireless connection, to an endoscopically implanted microstimulator 1701. Operationally, the controller 1702, via a processor in data communication with a memory storing programmatic instructions, causes the waveform generator 1704 to generate a predefined waveform, having an associated pulse width, amplitude, and frequency, which is transmitted wirelessly into the patient's subcutaneous region and into the transducer 1703, which further transmits the energy to the microstimulator 1701. A patient applies the stimulation source 1700 intermittently for a short time period, preferably thirty minutes or less, over the transducer site. Where the microstimulator 1701 comprises a local memory for storing programmatic instructions, in particular stimulation parameters and processes, the stimulation source 1700 need not comprise a controller and memory for storing such programmatic instructions and may simply transmit a predefined amount of energy to the transducer 1703 and, thus, to the microstimulator 1701. It should be appreciated that, regardless of the type, the stimulation source 1700 can be integrated into a plurality of different housings, including a miniature flashlight, cell phone case, or smart card. In one embodiment, the subcutaneous transducer 1703 receives lower frequency electromagnetic energy and commands from the stimulation source 1700 and converts the energy into high frequency RF energy. The frequency conversion will be less efficient than direct RF transmission but the use of the subcutaneous transducer will assist in eliminating heating issues. In addition, the subcutaneous transducer can also be used as a simple energy storage unit. In another embodiment, the subcutaneous transducer 1703 receives lower frequency electromagnetic energy and commands from the stimulation source 1700 and converts the energy into ultrasound energy.

Figure 18:
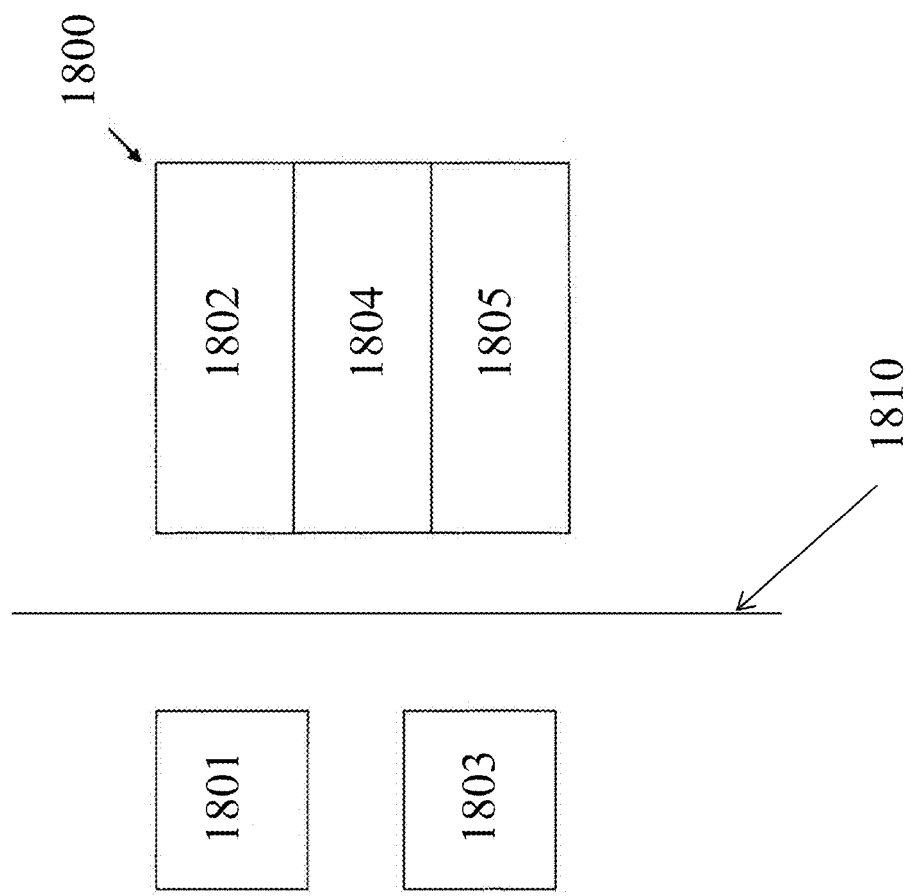
FIG. 18 is a third embodiment of a block diagram of certain modules of the present invention.

In another embodiment, referring to FIG. 18, a patient is treated by laparoscopically implanting a plurality of electrodes or electrodes 1801 (within the anatomical area to be stimulated) in wired communication with a transducer 1803 (comprising an antenna) proximate to the skin surface. The transducer 1803 wirelessly communicates with an external energy source 1800 (comprising a controller 1802, waveform generator 1804, and power source 1805, such as a battery) across the surface of the patient's skin 1810. The external energy source 1800 can be applied to the stimulation site by a patient, as described above. With close energy source application, radio frequency, ultrasound, or inductive/magnetic energies can be used.

As further discussed below, the stimulation source 1600, 1700, 1800 can initiate or terminate stimulation, when properly placed over the appropriate site, based on any of a plurality of triggers, including manually by a patient, patient activity, or other sensed patient states. The stimulation source 1600, 1700, 1800 can generate a plurality of different pulse widths, amplitudes, frequencies, or combinations thereof, as further described below.

Therapy Two: Controller Timed and Delivered Stimulation

In a second therapy, a patient may not be effectively therapeutically treated with intermittent wireless short bursts of stimulation applied a plurality of times during a day. Rather, a patient requires bursts of stimulation for a period greater than a predefined period of time, or for a frequency of more than a predefined number of times per day. Accordingly, a patient is subjected to stimulation that is initiated, effectuated, or otherwise triggered by a programmed controller. This more frequent, or continuous, stimulation is effective to treat certain symptoms of a patient, including treatment of heartburn or regurgitation, or reaching a predetermined LES pressure, muscle tension or electrode impedance.

Figure 19:
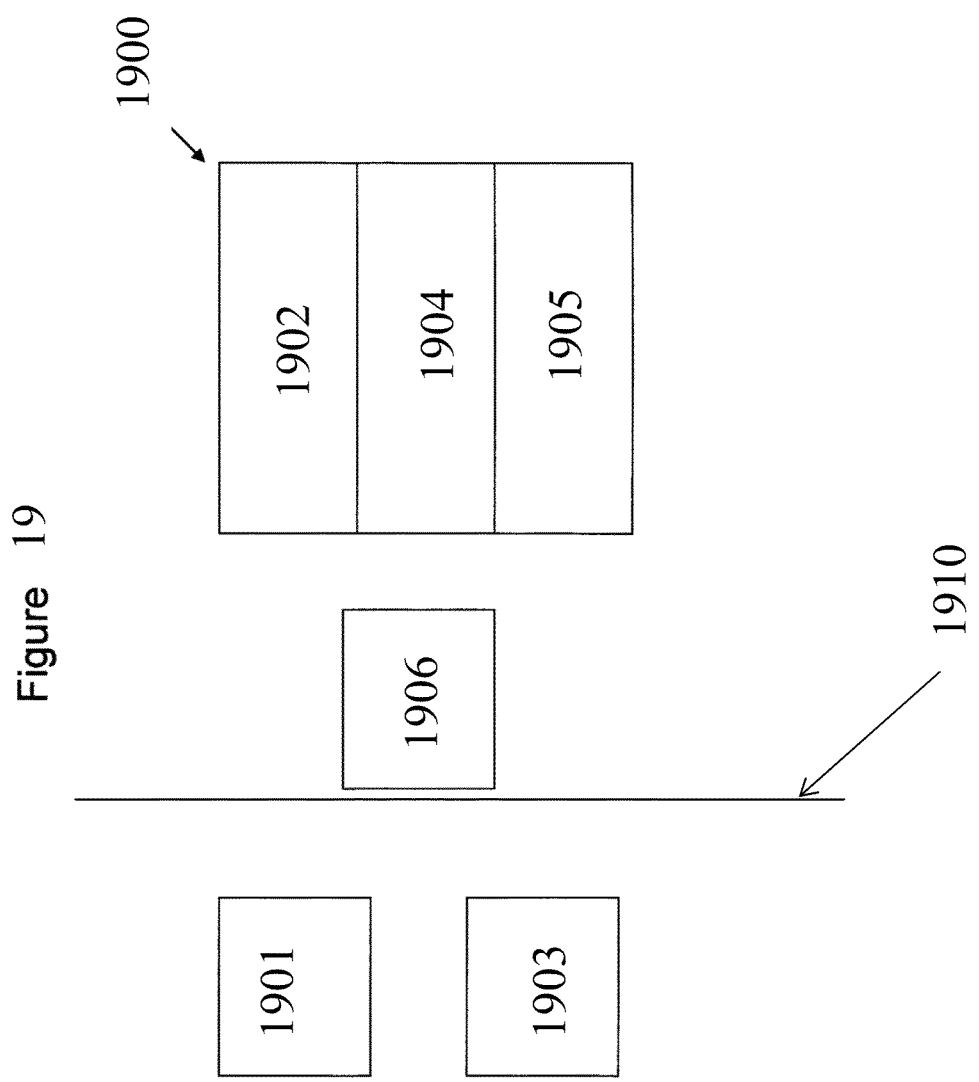
FIG. 19 is a fourth embodiment of a block diagram of certain modules of the present invention.

In this treatment method, a patient can be effectively treated by a plurality of embodiments, including:

1) Referring to FIG. 19, endoscopically implanting a microstimulator 1901 (having a receiver and placed within the anatomical area to be stimulated) in wireless or wired communication with a subcutaneously implanted transducer 1903 that, in turn, wirelessly communicates with a transducer 1906 (comprising at least one antenna and an adhesive surface) applied to the patient's skin surface 1910 which is wired to, and receives signals from, a stimulator source 1900 (comprising a controller 1902, waveform generator 1904, and power source 1905, such as a battery). The controller 1902 can be programmed to initiate or terminate stimulation based on a plurality of patient-specific triggers, such as pH level, LES pressure, fasting state, eating state, sleeping state, physical incline, or patient activity state, among other triggers as further described below. The stimulation source 1900 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mAmp and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 20:
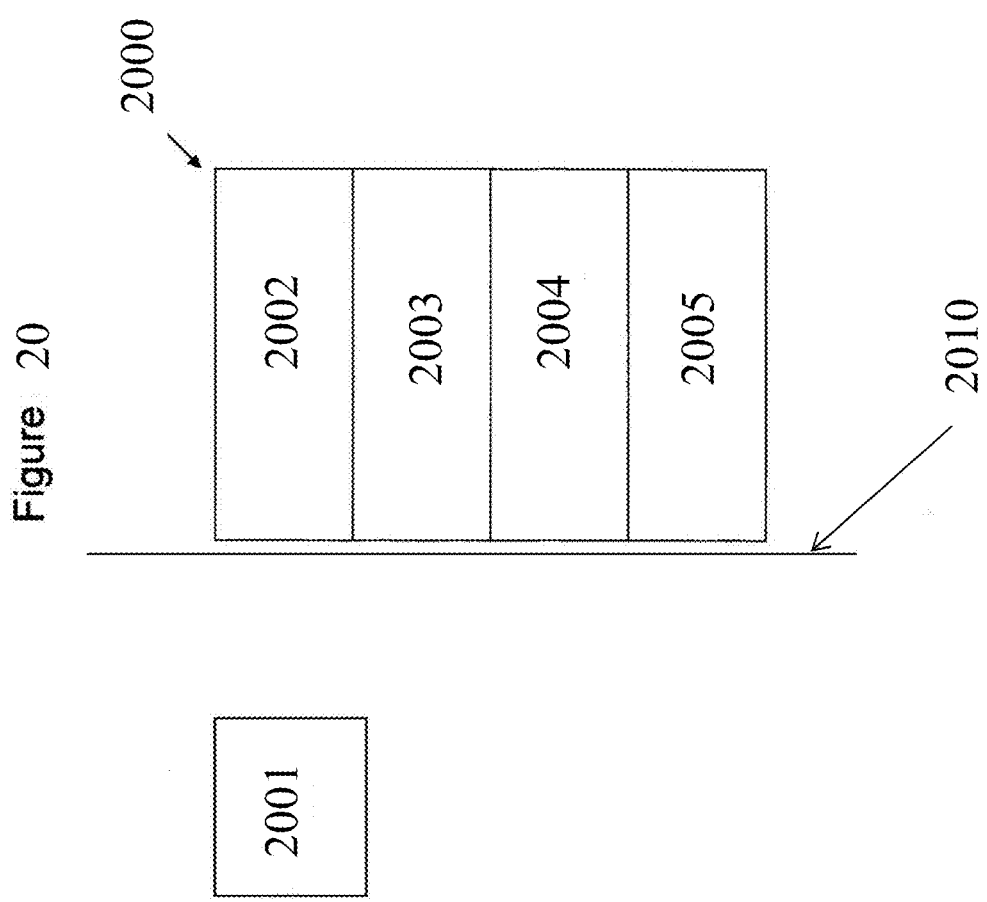
FIG. 20 is a fifth embodiment of a block diagram of certain modules of the present invention.

2) Referring to FIG. 20, endoscopically implanting a microstimulator 2001 (having a receiver and placed within the anatomical area to be stimulated) in wireless communication with a stimulator source 2000 (comprising a controller 2002, transducer 2003, waveform generator 2004, and power source 2005, such as a battery and which is held against a patient's skin 2010 over the microstimulator site, such as with straps, adhesives, garments, or bindings). The controller 2002 can be programmed to initiate or terminate stimulation based on a plurality of patient-specific triggers, such as pH level, LES pressure, fasting state, eating state, sleeping state, physical incline, or patient activity state, among other triggers as further described below. The stimulation source 2000 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mAmp and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 21:
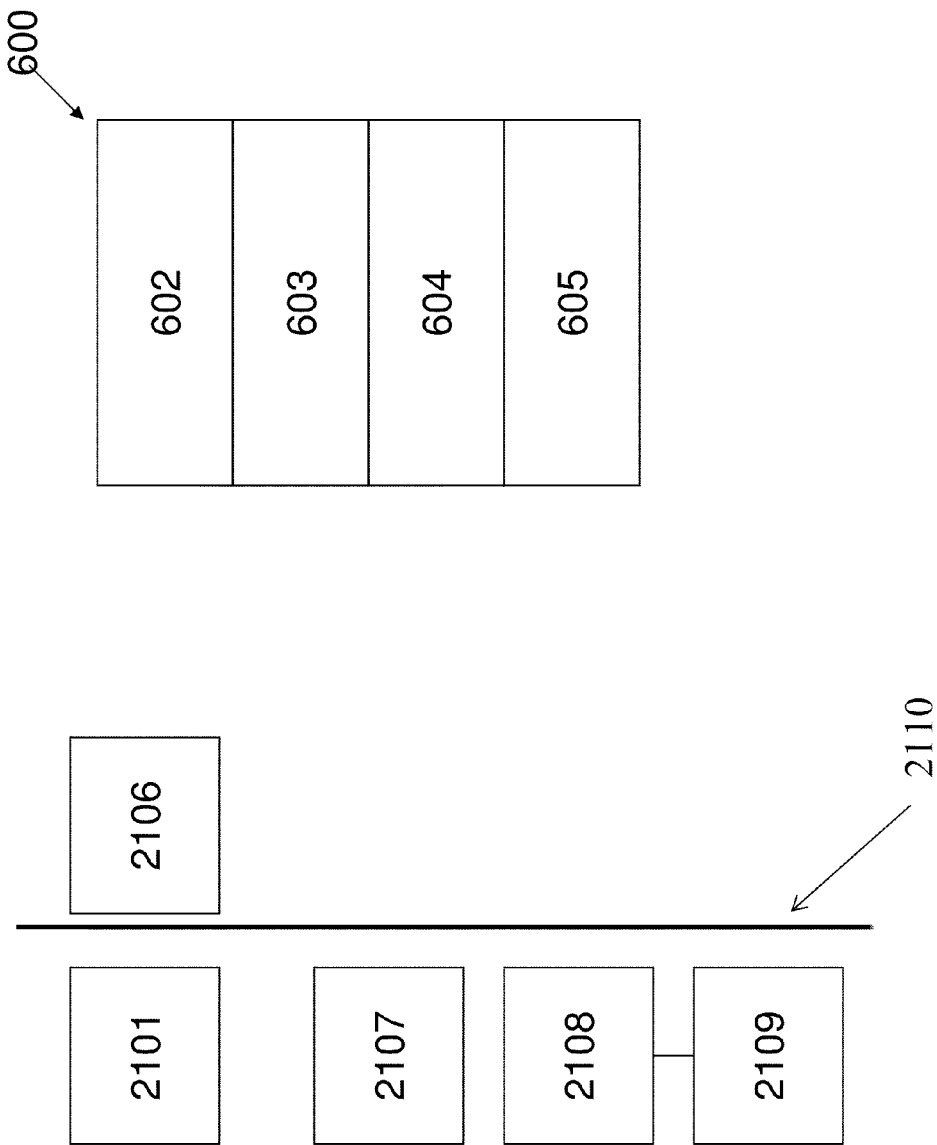
FIG. 21 is a sixth embodiment of a block diagram of certain modules of the present invention.

3) Referring to FIG. 21, endoscopically implanting a microstimulator 2101 (having a receiver and placed within the anatomical area to be stimulated) in wireless communication with a relay device 2106 worn over the stimulation site 2110 that is in wired communication with an external stimulator 2100, in wireless communication with an implanted adapter 2107 that is in wireless communication with an external stimulator 2100, or in wireless communication with an implanted transducer 2108 that is in wired communication, via an electrode, to an implanted stimulator 2109. The stimulator 2100 (comprising a controller 2102, transducer 2103, waveform generator 2104, and power source 2105, such as a battery) can be programmed to initiate or terminate stimulation based on a plurality of patient-specific triggers, such as pH level, LES pressure, fasting state, eating state, sleeping state, physical incline, or patient activity state, among other triggers as further described below. The stimulation source 2100 can generate and transmit radio frequency or ultrasound energy and can generate a plurality of different pulse widths, amplitudes, frequencies, or combinations thereof, as further described below. In one embodiment, the radio frequency or ultrasound pulse is designed to operate over a wireless distance of 6 inches or less, through the human body, with a maximum pulse amplitude of 10 mA and a maximum pulse width of 10 msec. It should be appreciated that if one parameter is lowered, such as the wireless distance (lowering it to one inch), another parameter can be modified accordingly, such as the amplitude (increasing it to 30 mAmp).

Figure 22:
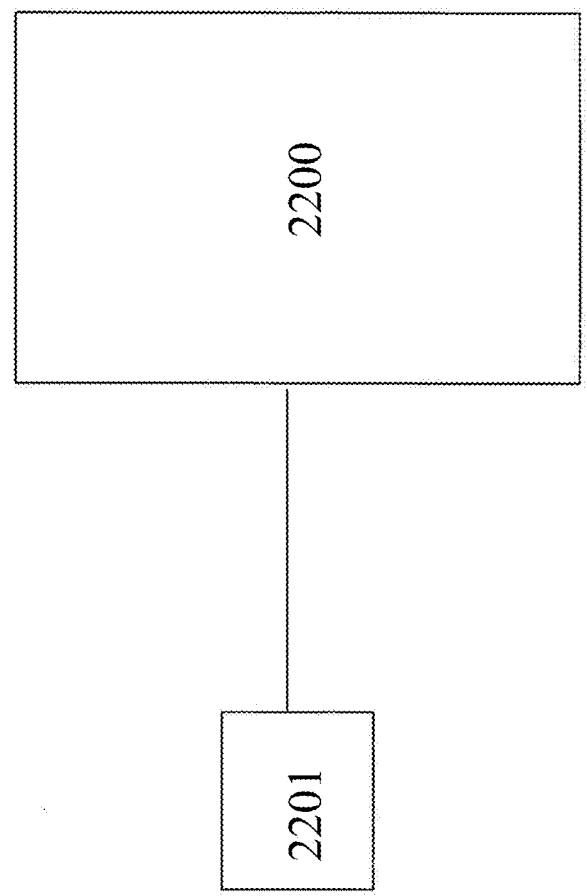
FIG. 22 is a seventh embodiment of a block diagram of certain modules of the present invention.

4) Referring to FIG. 22, laparoscopically implanting a plurality of electrodes 2201 (within the anatomical area to be stimulated) in wired communication with an implanted stimulator 2200 (comprising a primary cell that provides energy and a memory with programmatic instructions for defining appropriate stimulation parameters) which can be programmed to generate stimulation either continuously or periodically based on a predefined program or based on patient-specific triggers, such as pH level, LES pressure, LES impedance, fasting state, eating state, sleeping state, physical incline, or patient activity state, among other triggers as further described below. The stimulator 2200 may also wirelessly receive control data or information from an external device, which may be controlled, at least in part, by a physician or patient. The stimulator 2200 can generate a plurality of different pulse widths, amplitudes, frequencies, or combinations thereof, described above.

Figure 23:
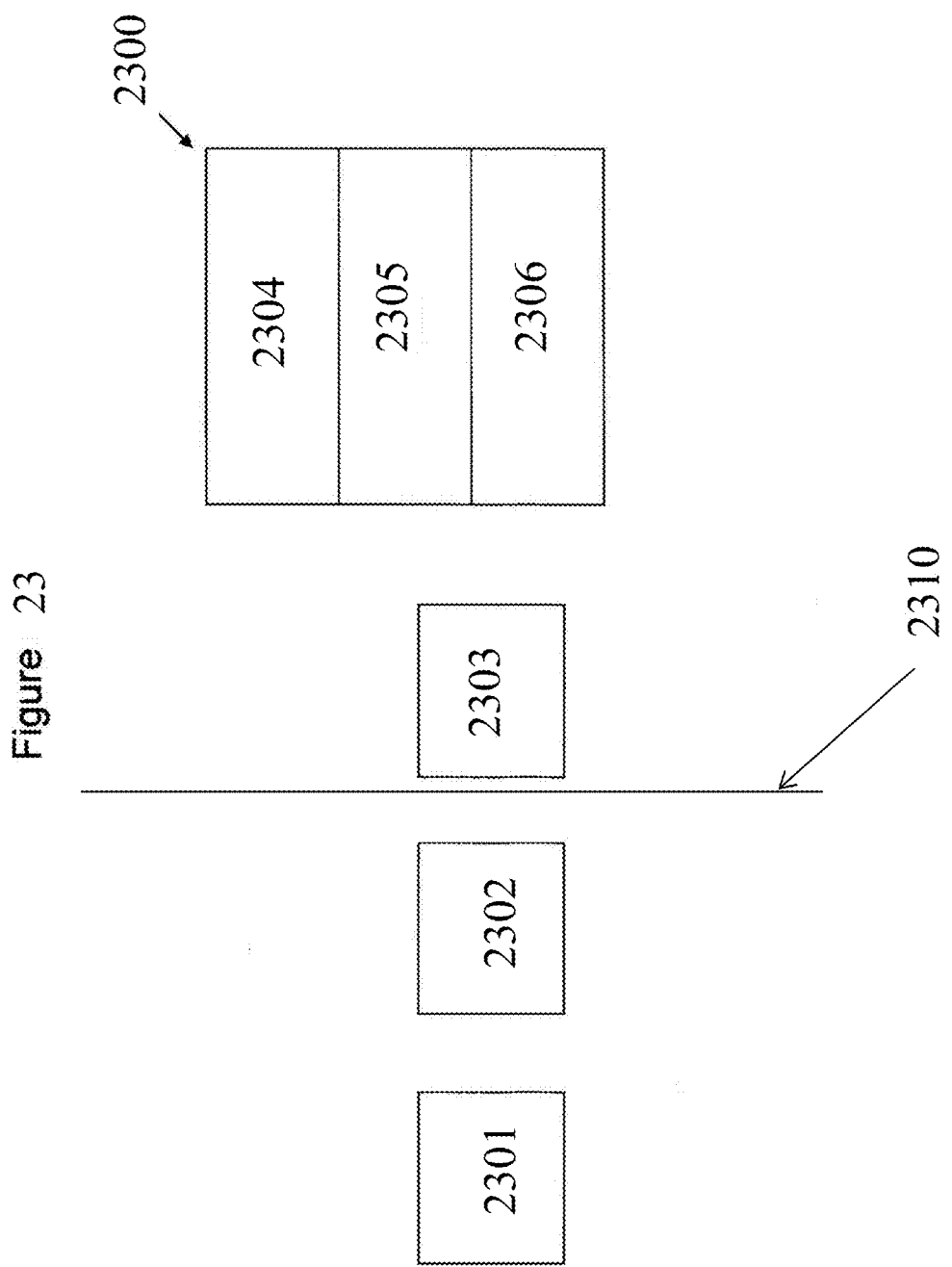
FIG. 23 is a eighth embodiment of a block diagram of certain modules of the present invention.
Figure 24:
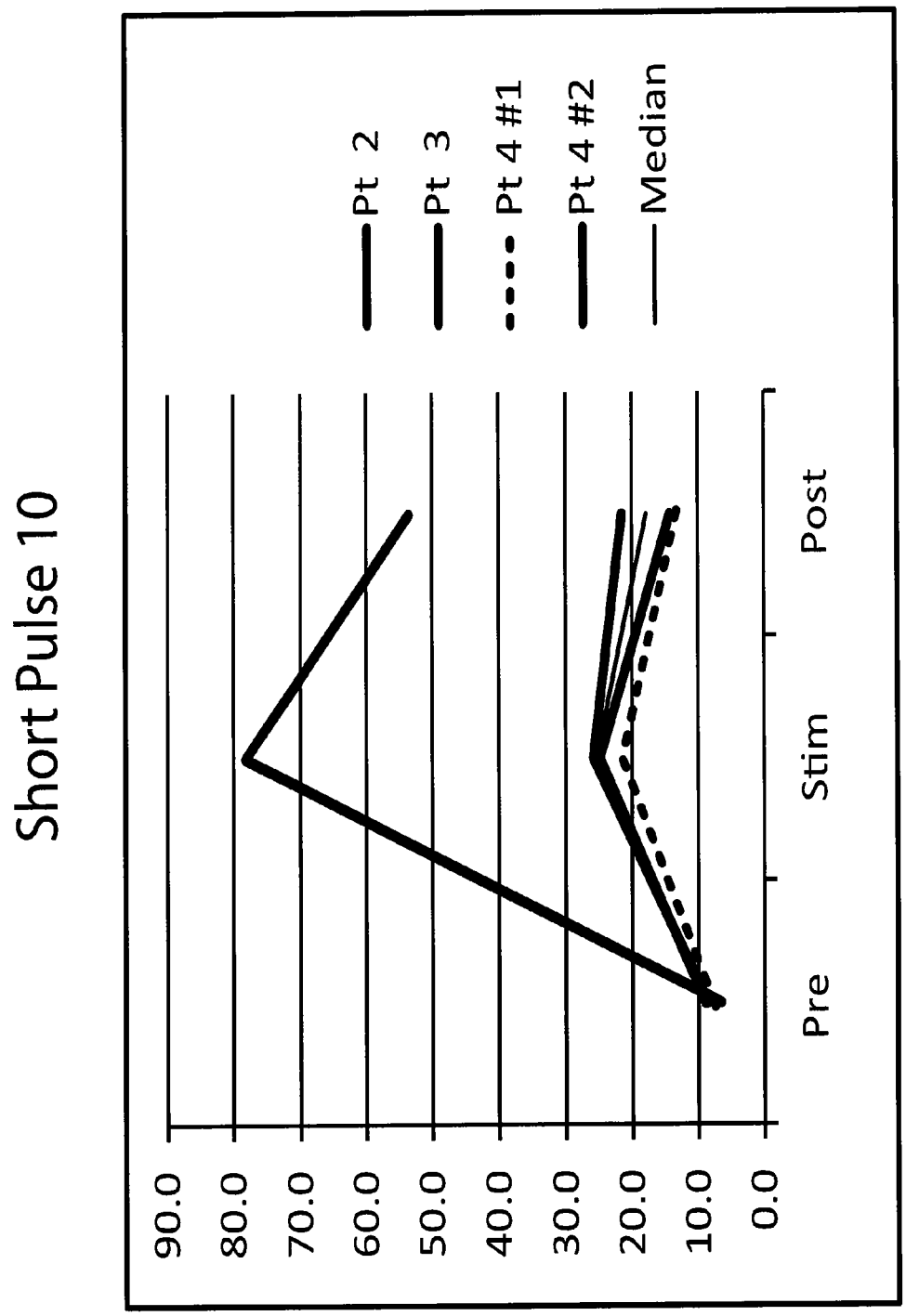
FIG. 24 is a graph relating pressure increases to baseline, stimulation, and post-stimulation periods.

5) Referring to FIG. 23, laparoscopically implanting a plurality of electrodes 2301 (within the anatomical area to be stimulated) in wired communication with a subcutaneously implanted transducer 2302 that, in turn, wirelessly communicates with a stimulator source or a transducer 2303 (comprising at least one antenna and an adhesive surface) applied to the patient's skin surface 2310 which is wired to, and receives signals from, a stimulator source 2300 (comprising a controller 2304, waveform generator 2305, and power source 2306, such as a battery). The controller 2304 can be programmed to initiate or terminate stimulation based on a plurality of patient-specific triggers, such as pH level, LES pressure, fasting state, eating state, sleeping state, physical incline, or patient activity state, among other triggers as further described below. The stimulation source 2300 can generate and transmit radio frequency or ultrasound energy and can generate a plurality of different pulse widths, amplitudes, frequencies, or combinations thereof, as further described below.

It should be appreciated that, while the disclosed system can use RF, inductive coupling, magnetic coupling or ultrasound, in one embodiment, the system can combine the use of RF inductive coupling, magnetic coupling, and ultrasound to take best advantage of transmission efficiencies in various media. In one embodiment, the external stimulator source generates RF waveforms, which wirelessly transmits RF energy to an intermediary receiver, that can be implanted subcutaneously and that converts the received RF energy into an ultrasound waveform. The intermediary receiver has an RF receiver, an ultrasound waveform generator, and an ultrasound transmitter. In another embodiment, the device comprises a means for storing a charge locally, such as a short-term energy storage component, such as a capacitor, and an associated trigger mechanism, as described above.

It should further be appreciated that the microstimulator (or, where a laparoscopically implanted stimulation electrode and stimulator are used, the stimulator) can locally store energy, be used with RF or US, and rely on an external device for stimulation control and/or energy recharge. Specifically, the microstimulator can comprise a means for storing a charge locally, such as a capacitor. It should further be appreciated that the anatomical region to be stimulated, such as the LES, areas within 2 cm of the LES, the esophagus, or the UES, may be stimulated using a plurality of microstimulators or electrodes, including an array of microstimulators or electrodes affixed to a mesh or other substrate. It should further be appreciated the microstimulator or implanted stimulator can store enough energy to function as a backup, or otherwise fill in gaps in energy transfer from an external source when, for example, wireless transmission coupling is interrupted or inefficient. In another embodiment, the microstimulator or implanted stimulator receives an energy stream from an external stimulator and, in real-time, forms the requisite waveform based on parameters encoded in a wireless control stream or embedded in the energy stream. In another embodiment, the microstimulator or implanted stimulator receives a preformed waveform from an external stimulator.

As discussed above, the endoscopic therapeutic treatments are part of the diagnosis process in which a microstimulator is endoscopically implanted and used in combination with an external device for an initial period. Data is gathered regarding frequency of stimulation required, amount of energy required, and other factors. A patient then receives a laparoscopically implanted permanent system operating in accordance with the gathered data.

Exemplary Use No. 1

In one embodiment, patients with diagnosis of GERD responsive to PPI, increase esophageal acid on 24 h pH monitoring off GERD medications, basal LES pressures ≥5 mm Hg, hiatal hernia <2 cm and esophagitis ≤LA Grade B had a stimulator placed endoscopically in the LES by creating a 3 cm submucosal tunnel. The stimulator was secured to the esophagus muscularis or serosa. Electrical stimulation (EST) was delivered 6-12 hours post-implant per following protocols 1) Short-pulse (SP) 200 μsec, 20 Hz, 10 mAmp; if no response in LES pressure increase to 15 mAmp; if increase in LES pressure decrease to 5 mAmp and 2) Intermediate-pulse (IP) 3 msec, 20 Hz, 5 mAmp for 20 minutes; if no response, increase to 10 mAmp. Each session of EST lasted 20 minutes and was followed by a washout period of 20 minutes or time needed for LES pressure to return to baseline, whichever was longer. High-resolution manometry was performed using standard protocol pre-, during and post-stimulation. Symptoms of heartburn, chest pain, abdominal pain and dysphagia pre-, during and post-stimulation were also recorded. Continuous cardiac monitoring was performed during and after the stimulation to look for any adverse cardiac events associated with EST.

Three patients underwent successful stimulator implantation. One patient was stimulated using 200 μsec, 20 Hz, 3 mAmp (SP 3) and had a significant increase in the LES pressure (Baseline=5.7 mm Hg; post-stimulation=42 mm Hg). As shown in FIGS. 24-30, patients had a significant increase in the LES pressure with all sessions of EST (Table 5). There was no effect on swallow induced relaxation and improvement in post-swallowing LES pressure augmentation with EST. There were no adverse EST related symptoms or any cardiac rhythm abnormalities.

TABLE 5

| | Median LES pressure (mmHg) | | |
|---|---|---|---|
| EST Protocol | Pre-Stimulation | Stimulation | Post-Stimulation |
| SP-10 mAmp | 8.1 | 25.3 | 17.9 |
| SP-5 mAmp | 9.7 | 37.7 | 17.8 |
| IP-5 mAmp | 6.5 | 26.0 | 29.2 |

Accordingly, in patients with GERD, EST results in significant increase in LES pressure without affecting patient swallow function or inducing any adverse symptoms or cardiac rhythm disturbances. EST delivered via a wired or wireless electrical stimulator offers a novel therapy to patients with GERD.

Exemplary Use No. 2

In one embodiment, a patient with diagnosis of GERD has a baseline LES pressure of 4-6 mmHg and impedance was about 320 ohms. A stimulation having a pulse of 200 μs and 5 mAmp was applied. After 15 minutes, a sustained LES tone of 25-35 mmHg was observed, which remained high for over 90 minutes after stopping stimulation. After 3 hours, the LES pressure returned to baseline. This patient was than treated using a patient specific stimulation protocol of 200 μs pulse, 5 mAmp amplitude, 20 Hz frequency, an ON phase of 20 minutes and an OFF phase of 2 hours. His LES was restored to normal function and his GERD was controlled.

Exemplary Use No. 3

In one embodiment, a patient with diagnosis of GERD has a baseline LES pressure of 4-6 mmHg and impedance was about 320 ohms. A stimulation having a pulse of 200 μs and 10 mAmp was applied. After 15 minutes, a sustained LES tone of 25-35 mmHg was observed. The patient was instructed to engage in a wet swallow. The patient engaged in a wet swallow, while stimulation was being applied, without feeling any substantive inhibition of the swallow function. This patient was then treated using a patient specific stimulation protocol of 200 μs pulse, 5 mAmp amplitude, 20 Hz frequency, an ON phase of 20 minutes and an OFF phase of 2 hours. His LES was restored to normal function and his GERD was controlled. Optionally, a pressure sensor was implanted in the LES and used to terminate the ON phase when a sustained LES pressure of greater than 20 mmHg for 5 minutes was achieved and used to terminate the OFF phase when a sustained LES pressure reaching 10 mmHg or the patient's baseline, whichever is higher, was achieved.

Exemplary Use No. 4

In one embodiment, patients are subjected to a series of diagnostic tests to determine a plurality of therapeutic stimulation parameters and to select stimulation parameters with the lowest average charge which is still able to elicit a pressure response in the range of at least 15-20 mmHg sustained for at least 5 minutes as measured in manometry. The diagnostic tests include subjecting patients to a series of stimulation sequences, as provided in the table below:

TABLE 6

Stimulation Sequence Settings

| Sequence # | Electrical Stimulation Type | Pulse Frequency | Pulse Duration | Pulse Amplitude |
|---|---|---|---|---|
| 1 | High-Frequency | 20 Hz | 200 μsec | 5 mAmp |
| 2 (only if #1 does not reach 20 mmHg or invoke a sufficiently positive response) | High-Frequency | 20 Hz | 200 μsec | 10-15 mAmp (preferably 10 mAmp) |
| 3 (only if #2 does not reach 20 mmHg or invoke a sufficiently positive response) | Mid-Frequency | 20 Hz | 3 ms | 5-15 mAmp (preferably 10 mAmp) |
| 4 (only if #3 does not reach 20 mmHg or invoke a sufficiently positive response) | Mid-Frequency | 20 Hz | 3 ms | 5-15 mAmp |
| 5 (only if #4 does not reach 20 mmHg or invoke a sufficiently positive response) | Low-frequency | 6 cycles/min | 375 ms | 5 mAmp |
| 6 (only if #5 does not reach 20 mmHg) | Low-frequency | 6 cycles/min | 375 ms | 5-15 mAmp |

Each selected stimulation parameter is applied for 5 hours during which stimulation is turned on until pressure is greater than or equal to 20 mmHg for at least 5 minutes (or until the time of duration reaches 60 minutes) and then stimulation is turned off until the pressure drops to less than 10 mmHg, or the patient's baseline, whichever is higher. Stimulation is then turned on again until reaching greater than or equal to 20 mmHg again for at least 5 minutes. This on-off process continues while the time duration between each on-off cycle is recorded. If the patient experiences pain or discomfort for any given stimulation sequence, the pulse amplitude is decreased in 1 mAmp increments until stimulation is tolerable. Once the tolerable setting is established, the stimulation period is re-initiated. Optionally, there is a washout period between sequences to remove any residual effect from the application of a prior sequence. That washout period can be equal to one hour or until LES pressure returns to the patient's baseline, whichever is longer. Optionally, continuous manometry is performed during the post-stimulation period to assess any delayed effect from a failed sequence or to measure the duration of effect from a successful sequence.

During the last two hours of the diagnostic session, stimulation is turned "on" and "off" at fixed durations based on the measured values recorded in the first part of the test. Impedance measurements are performed periodically during this phase using an external impedance measurement device or by measuring the resulting voltage waveform from stimulation using a floating oscilloscope.

Optionally, a second dosing evaluation process is performed building on the sequence results as performed above. In one embodiment, a patient's baseline LES pressure is evaluated over a 20 minute period. Simulation is applied for 125% of the on time period, as determined from the first set of sequence measurements. Stimulation is then stopped for 75% of the off time period, as determined from the first set of sequence measurements, or until LES pressure falls below 10 mmHg or baseline, whichever is higher. Restart stimulation for 125% of the on time period and monitor LES pressure. If LES pressure does not reach 20 mmHg, then continue stimulation for up to 150% of the on time period or until pressure reaches 20 mmHg (whichever comes first). Repeat the off time period and continue cycling between the prior on time period and off time period until achieving 6 hours of LES pressure above 10 mmHg. Conduct esophageal manometry with wet swallows post stimulation sequence.

Exemplary Use No. 5

In one embodiment, patients are subjected to a series of diagnostic tests to determine a plurality of therapeutic stimulation parameters and to select stimulation parameters with the lowest average charge which is still able to elicit a pressure response in the range of at least 15-20 mmHg sustained for at least 5 minutes as measured in manometry. The diagnostic tests include subjecting patients to a series of stimulation sequences, as provided in the table below:

TABLE 7

| Sequence # | Electrical Stimulation Type | Pulse Frequency | Pulse Duration | Pulse Amplitude | Stimulation Duration |
|---|---|---|---|---|---|
| 1 | Baseline | 0 Hz | 0 μsec | 0 mAmp | 0 minutes |
| 2 | High-Frequency | 20 Hz | 200 μsec | 5 mAmp | 30 minutes |
| 3 (only if #2 does not reach 20 mmHg or invoke a sufficiently positive response) | High-Frequency | 20 Hz | 200 μsec | 10-15 mAmp (preferably 5 mAmp) | 60 minutes |
| 4 (only if #3 does not reach 20 mmHg or invoke a sufficiently positive response) | High-Frequency | 20 Hz | 200 μsec | 10 mAmp | 30 minutes |
| 5 (only if #4 does not reach 20 mmHg or invoke a sufficiently positive response) | High-Frequency | 20 Hz | 200 μsec | 5-15 mAmp (preferably 10 mAmp) | 60 minutes |
| 6 (only if #5 does not reach 20 mmHg or invoke a sufficiently positive response) | High-Frequency | 20 Hz | 200 μsec | 15 mAmp | 30 minutes |
| 7 (only if #6 does not reach 20 mmHg) | High-Frequency | 20 Hz | 200 μsec | 15 mAmp | 60 minutes |

Stimulation is turned on until pressure is greater than or equal to 20 mmHg for at least 5 minutes (or until the list time duration is reached) and then stimulation is turned off until the pressure drops to less than 10 mmHg, or the patient's baseline, whichever is higher. Stimulation is then turned on again until reaching greater than or equal to 20 mmHg again for at least 5 minutes. This on-off process continues while the time duration between each on-off cycle is recorded. If the patient experiences pain or discomfort for any given stimulation sequence, the pulse amplitude is decreased in 1 mAmp increments until stimulation is tolerable. Once the tolerable setting is established, the stimulation period is re-initiated.

Optionally, there is a washout period between sequences to remove any residual effect from the application of a prior sequence. That washout period can be equal to one hour or until LES pressure returns to the patient's baseline, whichever is longer. Optionally, continuous manometry is performed during the post-stimulation period to assess any delayed effect from a failed sequence or to measure the duration of effect from a successful sequence. Optionally, continuous manometry is performed during the post-stimulation period from the successful sequence to determine the duration of the effect, that is, until the LES pressure is below 10 mm Hg or reaches baseline, whichever is higher.

The stimulation sequences listed above may be repeated, if no success is achieved, except using a 3 msec dose instead of the 200 μsec dose.

Optionally, a second dosing evaluation process is performed building on the sequence results as performed above. In one embodiment, a patient's baseline LES pressure is evaluated over a 20 minute period. Simulation is applied for 125% of the on time period, as determined from the first set of sequence measurements. Stimulation is then stopped for 75% of the off time period, as determined from the first set of sequence measurements, or until LES pressure falls below 10 mmHg or baseline, whichever is higher. Stimulation is restarted for 125% of the on time period and LES pressure is monitored. If LES pressure does not reach 20 mmHg, then continue stimulation for up to 150% of the on time period or until pressure reaches 20 mmHg (whichever comes first). Repeat the off time period and continue cycling between the prior on time period and off time period until achieving 6 hours of LES pressure above 10 mmHg. Conduct esophageal manometry with wet swallows post stimulation sequence. Additional stimulation measurements can be made, including baseline manometry with wet swallows, repeating successful sequences for an extended period, such as 12 hours, or manometry measurements with wet swallows after conducting a successful stimulation sequence.

Exemplary Use No. 6

In one embodiment, 10 patients (9 females, 1 male mean age 52.6 years, range-40-60 years) with symptoms of GERD responsive to PPI's, low resting LES pressure and abnormal 24-hr intraesophageal pH test were enrolled. All had symptoms of heartburn and/or regurgitation for at least 3 months, which was responsive to therapy with proton pump inhibitors (PPI's). Preoperative evaluation included an upper GI endoscopy, esophageal manometry and ambulatory 24-hr esophageal pH recording. To be included, the patient's resting LESP had to be 5-15 mmHg, and the intraesophageal pH had to be less than four more than 5% of the time. Patients with hiatal hernia >3 cm, erosive esophagitis more severe than Los Angeles grade C, Barretts esophagus or non-GERD related esophageal disease were excluded.

Bipolar stitch electrodes were placed longitudinally in the LES during an elective laparoscopic surgery, secured by a clip and exteriorized through the abdominal wall. It consisted of two platinum-iridium electrodes with an exposed length of 10 mm. They were implanted longitudinally in the right and left lateral aspects the LES and secured by a clip. The electrode was then exteriorized through the laparoscopic port in the abdominal wall in the left upper quadrant and connected to a macrostimulator.

Following recovery, an external pulse generator delivered 2 types of stimulation for periods of 30 minutes: 1) low energy stimulation; pulse width of 200 µsec, frequency of 20 Hz amplitude and current of 5 to 15 mA (current was increased up to 15 mA if LESP was less than 15 mmHg), and 2) high energy stimulation; pulse width of 375 msec, frequency of 6 cpm and amplitude 5 mA. Resting LESP, amplitude of esophageal contractions and residual LESP in response to swallows were assessed before and after stimulation. Symptoms of chest pain, abdominal pain and dysphagia were recorded before, during and after stimulation and 7-days after stimulation. Continuous cardiac monitoring was performed during and after stimulation.

The high frequency, low energy stimulation was delivered as square-wave pulses with a width of 200 microseconds at a frequency of 20 Hz and a current of 5-15 mA. If LESP did not increase to over 15 mmHg using the 5 mA stimulus, the current was gradually increased up to 15 mA. The low frequency, high energy stimulation was delivered as square-wave pulse with a width of 375 milliseconds at a frequency of 6 CPM and current of 5 mA. The current was not varied during low frequency stimulation.

If resting LESP rose above 15 mmHg during ES, the stimulus was terminated and LESP was allowed to return to its pre-stimulation baseline. A different stimulation was given when LESP returned to baseline. Stimulations were given in random order, with patients unaware of the type or timing of its delivery (frequent checks of impedance were mixed with stimulation). Five water swallows were given before and after termination of each session of ES. All studies were done under continuous cardiac monitoring, and patients were supervised closely. Patients were instructed to report any unusual symptom, and in particular dysphagia, palpitations, and chest/abdominal pain.

Nine subjects received high frequency, low energy and four subjects received low frequency, high energy stimulation. Both types of stimulation significantly increased resting LESP: from 8.6 mmHg 95%, CI 4.1-13.1 to 16.6 mmHg, 95% CI 10.8-19.2, p<0.001 with low energy stimulation and from 9.2 mmHg 95% CI 2.0-16.3 to 16.5 mmHg, 95% CI 2.7-30.1, p=0.03 with high energy stimulation. Neither type of stimulation affected the amplitude of esophageal peristalsis or residual LESP. No subject complained of dysphagia. One subject had retrosternal discomfort with stimulation at 15 mA that was not experienced with stimulation at 13 mA. There were no adverse events or any cardiac rhythm abnormalities with either type of stimulation.

With respect to high frequency, low energy stimulation, there was a consistent increase in resting LESP in all subjects, observed within 15 minutes of initiating ES, and increased further before the end of stimulation. High frequency, low energy stimulation had no effect on the amplitudes of esophageal contractions or residual LESP in response to 5 cc water swallows. One subject had chest discomfort when the stimulation current was increased to 15 mA, but resolved when the current was decreases to 13 mA.

With respect to low frequency, high energy stimulation, resting LESP consistently increased during stimulation. It had no effect on the amplitudes of peristaltic pressure waves in the smooth muscle esophagus or residual LESP produced by 5 cc water swallows. No abnormalities of cardiac or esophageal function were seen, and no adverse events occurred with either type of stimulation.

Both types of stimulation, high and low energy stimulation, caused a consistent and significant increase in LES pressure. Importantly, both LES relaxation and esophageal contractile activity in response to wet swallows were not affected, indicating that the integrity of the neuromuscular reflex pathways activated by swallows is maintained during stimulation. Stimulation was well tolerated. No patient reported dysphagia. Only one patient reported chest discomfort, with amplitude of 15 mA, that was not experienced when current was reduced to 13 mA. There was no evidence of cardiac adverse effects in any of the patients. Accordingly, short-term stimulation of the LES in patients with GERD significantly increases resting LESP without affecting esophageal peristalsis or LES relaxation.

Exemplary Use No 7

Six patients with GERD resistant to medical therapy and documented by pH testing underwent electrode implantation in the LES using laparoscopy. All patients had LES pressures in the range of 5-15 mm Hg. A macrostimulator was placed in the subcutaneous pocket using sterile techniques. Within 24 hours after the implant, LES electrical stimulation therapy was started using 215 µsec pulse at 3 mAmp and 20 Hz. For certain patients, the macrostimulator comprised an accelerometer/inclinometer which was used to program the delivery of stimulation twice daily, once every 12 hours, and then increased to 3 times daily, once every 8 hours.

The LES electrical stimulation therapy resulted in significant improvement and normalization of LES pressure as measured by high-resolution manometry and clinically significant decreases in esophageal acid as measured by 24 hour pH testing. All patients had decreases in symptoms measured by patient symptom diaries and improvements in health related quality of life measured by a Health Related Quality of Life survey, short form 12 (GERD HRQL). All patients were successfully taken off proton pump inhibitors medications, nor did the patients use the PPIs on an as-needed basis. None of the patients had treatment related symptoms or adverse events. All patients maintained a normal swallow function.

Referring to FIGS. 24 to 28, the treatment methodologies disclosed herein provide for a sustained improvement in patient LES pressure, a decrease in esophageal acid exposure, and decrease in reported symptoms. Relative to a baseline pressure 2410, patient LES pressure can achieve a greater than 2× increase during stimulation 2415 relative to baseline 2410 and can still retain an elevated pressure, relative to baseline 2410, after stimulation is terminated 2420.

Figure 25:
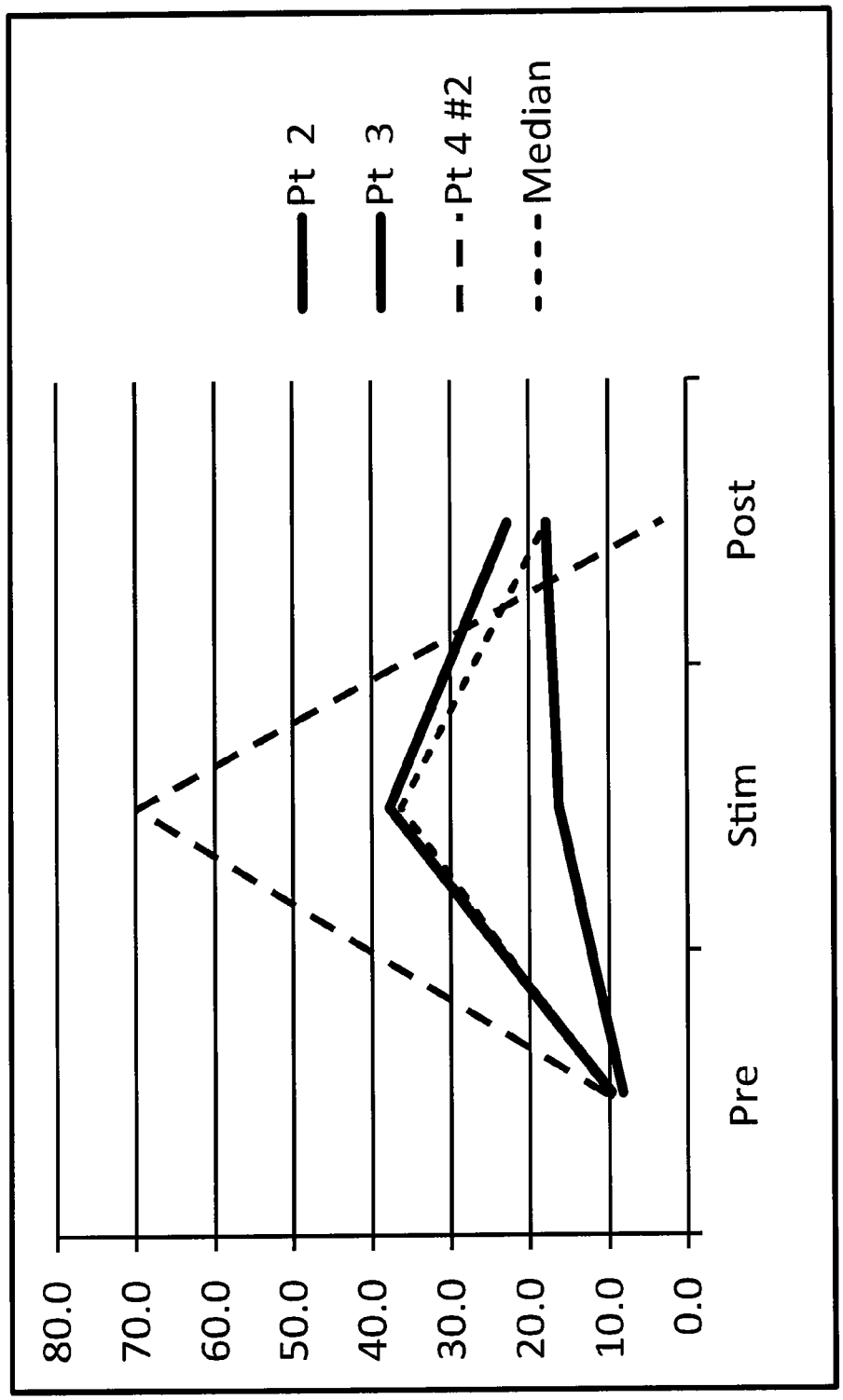
FIG. 25 is a graph showing an improved LES pressure profile over time.
Figure 26:
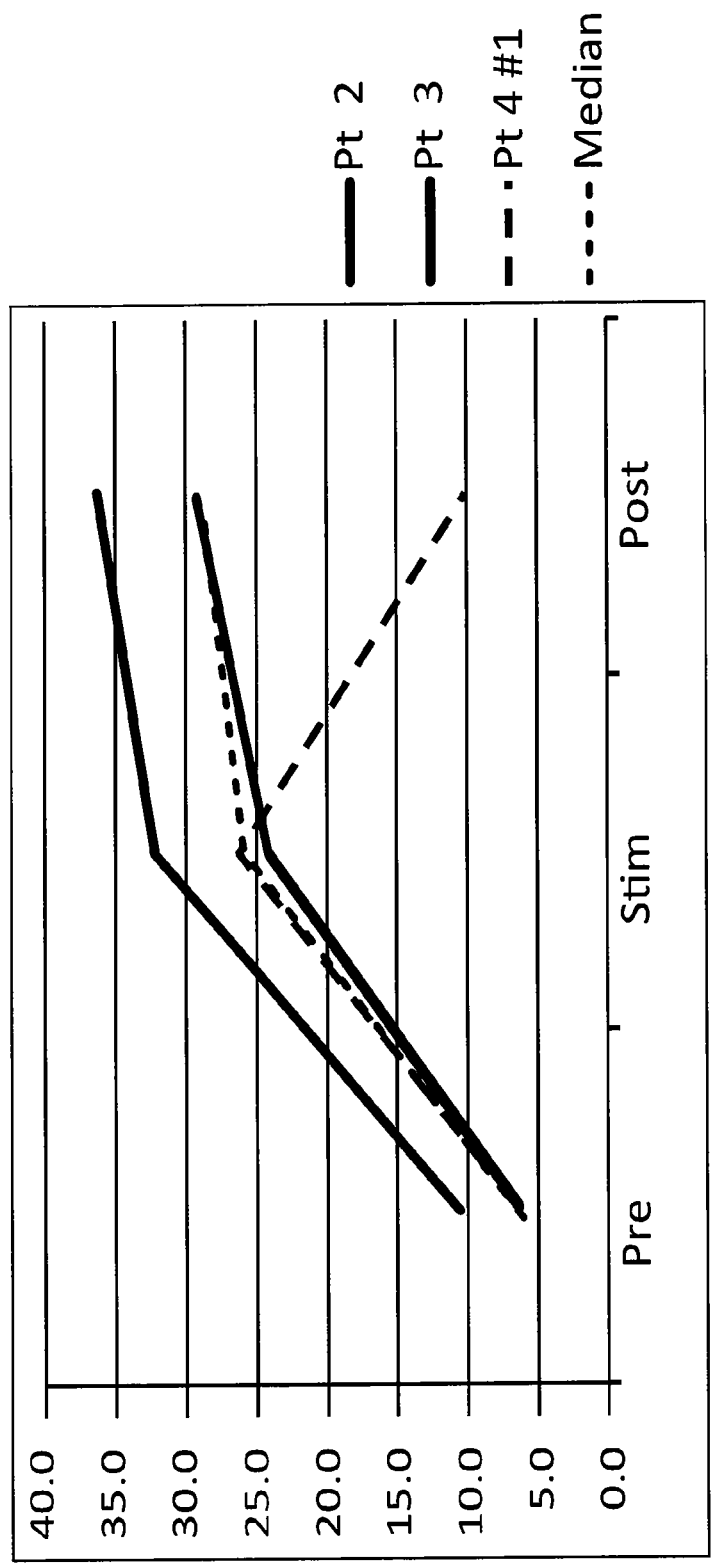
FIG. 26 is a graph showing a decrease in esophageal acid exposure over time.
Figure 27:
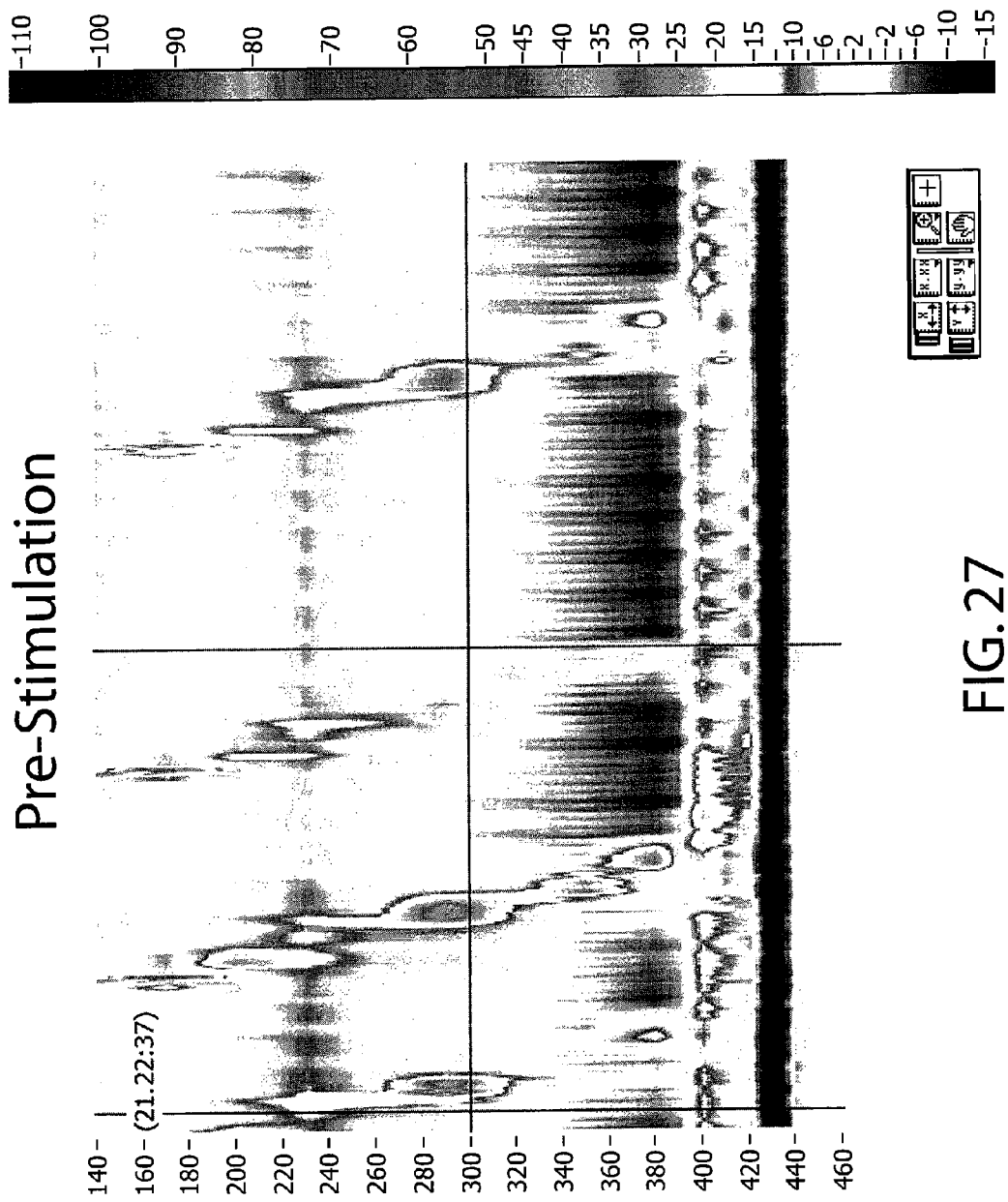
FIG. 27 is a graph showing a decrease in adverse symptoms over time.
Figure 28:
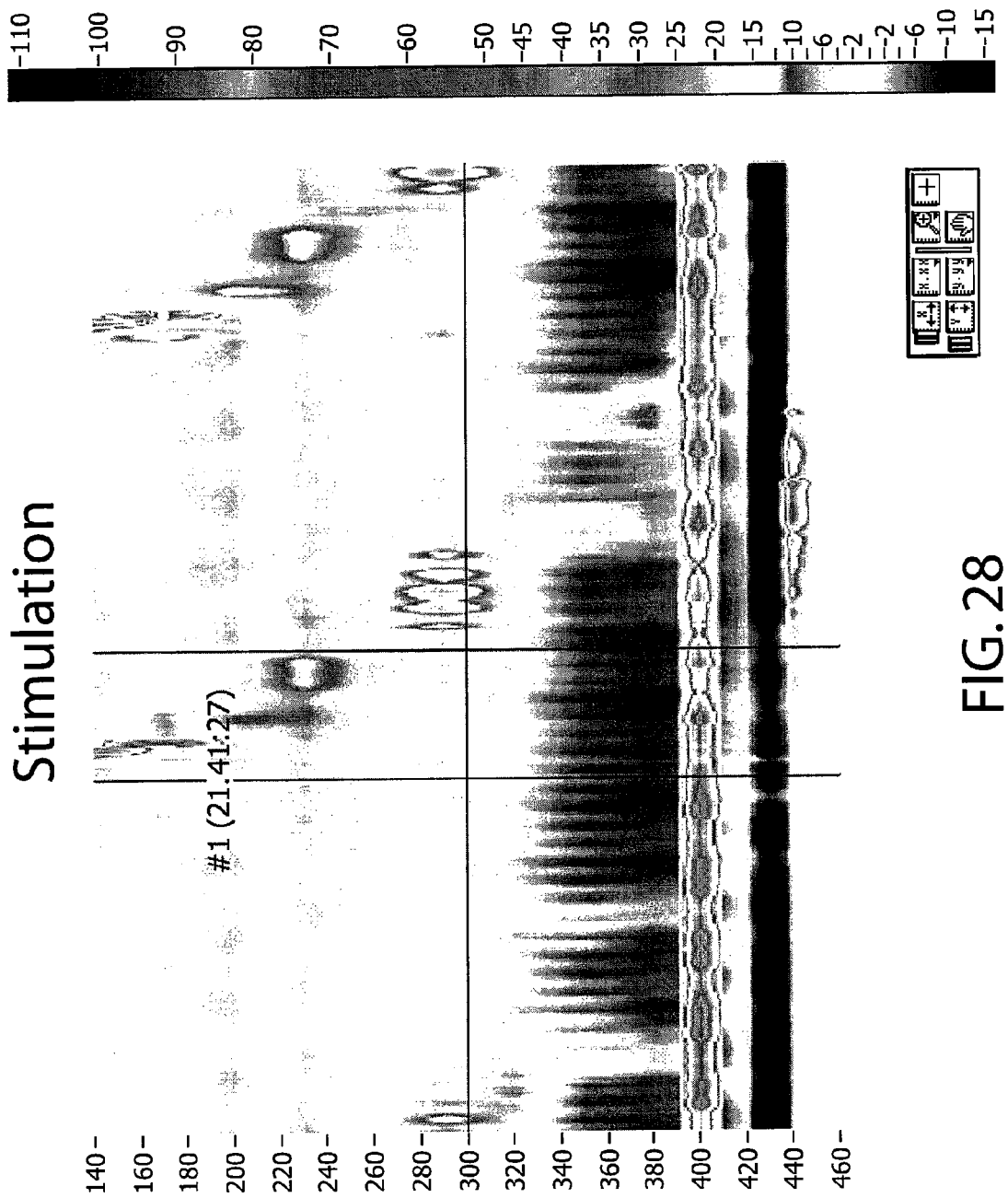
FIG. 28 is a graph showing an improved LES pressure profile over time.
Figure 29:
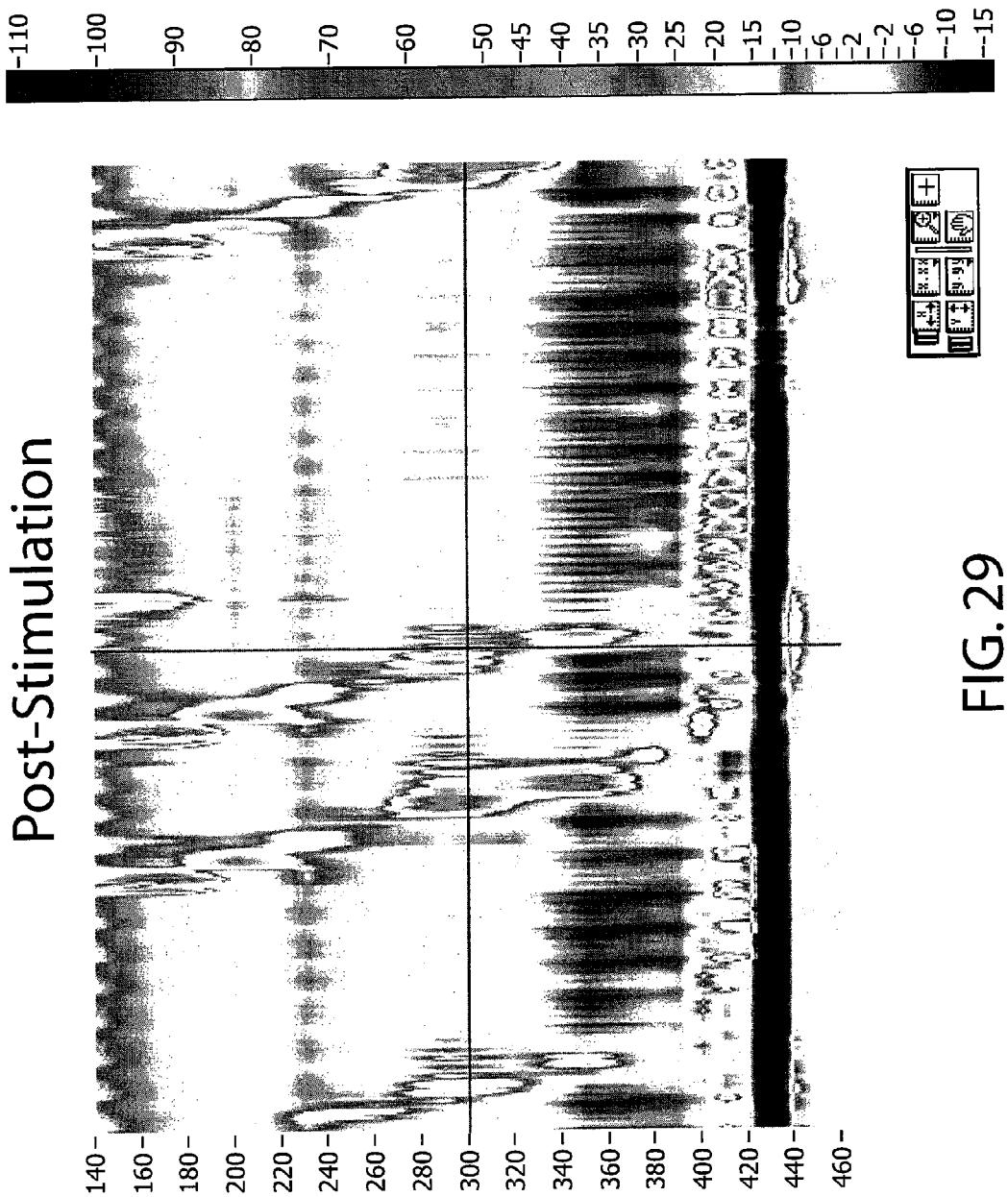
FIG. 29 is a graph showing an improved LES pressure profile over time.
Figure 30:
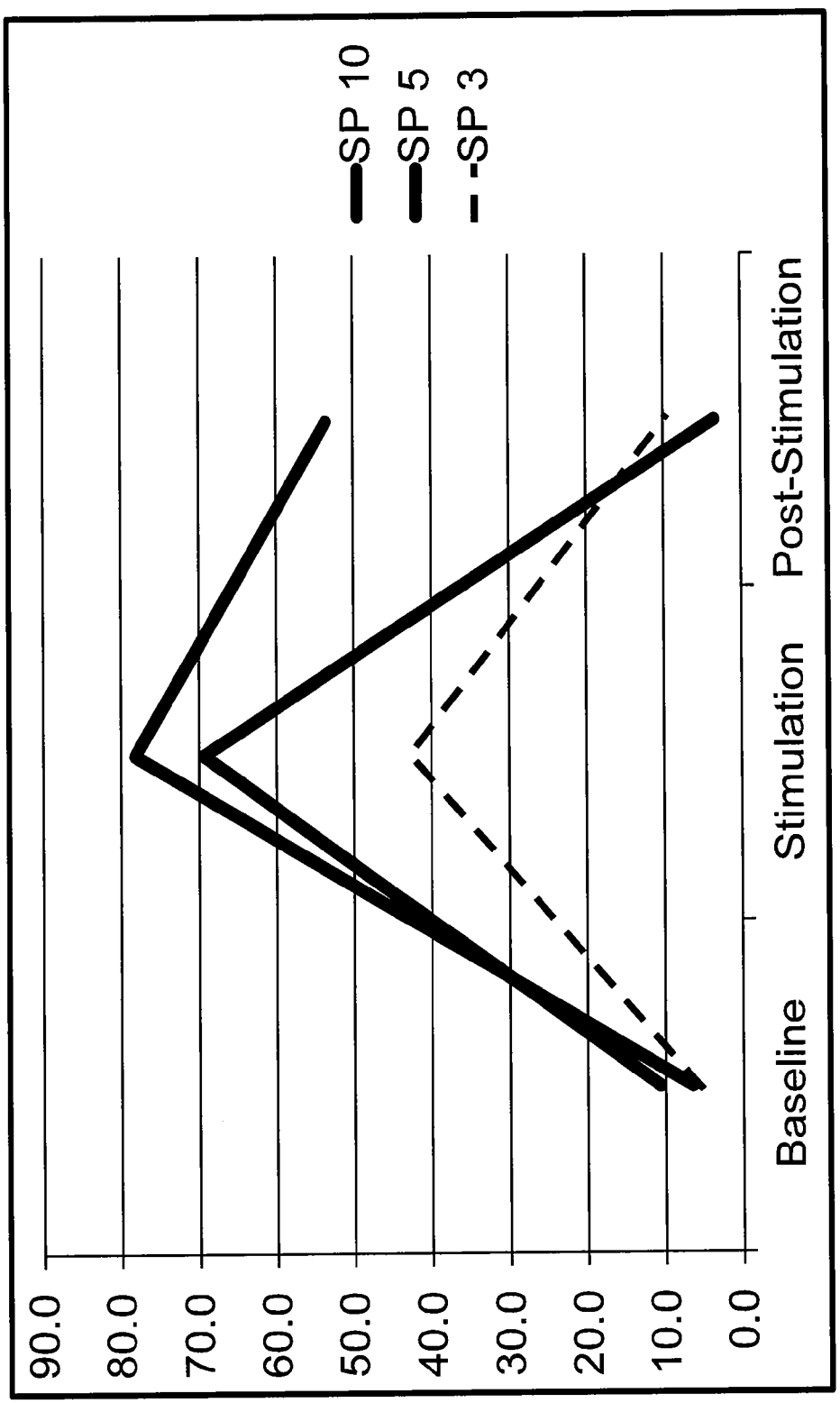
FIG. 30 is a graph showing the pressure profile of the three patients over time.

Additionally, as shown in FIG. 25, a patient's LES pressure can be reliably maintained 2515 within a normal pressure range, 15-25 mmHg, for weeks 2505 after LES stimulation is initiated. As a result, a patient's esophageal acid exposure 2615 can be brought within a normal pH range within one week after initiating treatment and maintained for several weeks thereafter 2605. Similarly, a patient's adverse symptoms, associated with GERD, 2715 can be brought within a normal range, as measured by GERD HRQL evaluations, within one week after initiating treatment and maintained for several weeks thereafter 2705. The benefits of the present therapy can also be obtained within hours after initiating and terminating stimulation. As shown in FIG. 28, relative to a pre-stimulation baseline 2820, a patient's LES pressure can be reliably maintained 2815 within a normal pressure range for hours 2805 after LES stimulation is terminated 2830.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

What is claimed is:

1. A system for increasing pressure of a patient's lower esophageal sphincter (LES), comprising: at least one electrode configured to contact the LES; a waveform generator coupled to the electrodes; and a controller configured to electrically stimulate the LES to increase the pressure of the LES, and maintain an average pressure of the LES above a pressure level which reduces at least one of a frequency of occurrence or an intensity of acid reflux symptoms in the patient both during and after stimulation by controlling the waveform generator to repeatedly: a) generate and apply an electrical pulse train to the LES through the electrodes for a stimulation period, and b) terminate the electrical pulse train for a rest period, wherein at least one of an amplitude, frequency, or duration of said pulse train is defined such that pressure of the LES normalizes after at least five minutes from when stimulation is initiated.

2. The system of claim 1, wherein the maintained average pressure does not induce dysphagia in the patient and allows the patient to swallow a bolus during both the stimulation period and rest period.

3. The system of claim 1, wherein the controller is configured to determine parameters of the electrical pulse train that maintain the average pressure of the LES above the pressure level during the rest period.

4. The system of claim 1, wherein the controller is configured to control the waveform generator to stimulate the LES based on a predetermined trigger of at least one of time of day and supine of the patient.

5. The system of claim 1, wherein the controller is configured to adjust a length of the stimulation period and a length of the rest period to maintain the average pressure of the LES above the pressure level.

6. The system of claim 1, including a sensor coupled to the controller for sensing physiological data of the patient, the sensor sensing at least one of pH level at the LES and pressure of the LES, wherein the controller is configured to control the waveform generator based on the sensed physiological data.

7. The system of claim 1, wherein the controller and the waveform generator are enclosed in a common housing and implanted in the patient.

8. The system of claim 1, including an external programming device for configuring the controller to adjust at least one of the energy per stimulation period, duration of the stimulation period, frequency of the stimulation period, and a number of stimulation periods per day based on at least one of the frequency of occurrence or the intensity of acid reflux symptoms in the patient.

9. The system of claim 1, including a disposable battery coupled to the waveform generator and the controller for powering the waveform generator and the controller.

10. The system of claim 1, wherein the controller is configured to control the waveform generator to set a pulse width of the electrical pulse train in a range from 1 µs to 1 second.

11. The system of claim 1, wherein the controller is configured to control the waveform generator to set a frequency of the electrical pulse train in a range from about 1 Hz to about 100 Hz.

12. The system of claim 1, wherein the controller is configured to control the waveform generator to set a current of pulses in the electrical pulse train in a range from 1 µAmp to 50 mAmps.

13. The system of claim 1, including a sensor coupled to the controller for sensing physiological data of a patient; and a memory coupled to the controller for storing the sensed data of the patient, wherein the controller is configured to control the waveform generator to adjust parameters of the electrical pulse train applied to the LES based on an analysis of the stored data.

14. The system of claim 1, including at least one of an accelerometer and inclinometer coupled to the controller for sensing posture data of the patient, wherein the controller is configured to control the waveform generator to adjust parameters of the electrical pulse train applied to the LES based on an analysis of the posture data.

15. The system of claim 1, including an antenna coupled to the controller for wirelessly receiving instructions for instructing the controller to adjust parameters of the electrical pulse train applied to the LES, wherein the instructions are set by at least one of the patient and a trained professional.

16. The system of claim 1, wherein the controller is configured to perform a diagnostic test on the patient by controlling the waveform generator to adjust an amount of electrical energy stimulating the LES over a treatment period based on at least one of the frequency of occurrence or the intensity of acid reflux symptoms in the patient.

17. A system for normalizing functionality of a patient's lower esophageal sphincter (LES), comprising: at least one electrode configured to contact the LES; a waveform generator coupled to the electrodes; and a controller configured to control the waveform generator to generate and apply an electrical pulse train to the LES through the electrodes during a stimulation period to produce said normalization of function in the LES during a rest period after termination of the electrical pulse train which reduces at least one of a frequency of occurrence or an intensity of acid reflux symptoms in the patient, wherein at least one of an amplitude, frequency, or duration of said pulse train is defined such that swallowing of the patient is not hindered by said stimulation.

18. The system of claim 17, wherein, prior to stimulation, the controller is configured with a length of the stimulation period and an electrical current of the pulse train that increases a pressure of the LES above a pressure level that reduces at least one of a frequency of occurrence or an intensity of acid reflux symptoms in the patient during the rest period.

19. The system of claim 17, wherein, prior to stimulation, the controller is configured to determine a length of the rest period that allows a pressure of the LES to increase above a pressure level that reduces at least one of a frequency of occurrence or an intensity of acid reflux symptoms in the patient and does not allow the pressure of the LES to decrease below the pressure level.

20. The system of claim 17, wherein the controller is configured with parameters of the electrical pulse train that produce a first increase in LES pressure during the stimulation period, and a second increase in LES pressure during the rest period.

21. The system of claim 17, wherein the controller is configured to determine parameters of the electrical pulse train that produce an increase in the LES pressure at a first rate during the stimulation period and at a second rate during the rest period.

22. A system for normalizing a function of a patient's lower esophageal sphincter (LES), comprising: at least one electrode configured to contact the LES; a waveform generator coupled to the electrodes; and a controller configured to control the waveform generator to generate and apply an electrical pulse train to the LES through the electrodes to normalize the function of the LES, which reduces at least one of a frequency of occurrence or an intensity of acid reflux symptoms in the patient while allowing the patient to swallow during electrical stimulation wherein at least one of an amplitude, frequency, or duration of said pulse train is defined such that said function of the LES normalizes after at least five minutes from when stimulation is initiated.

23. The system of claim 22, wherein the bolus has a volume of greater than 1 cubic centimeter (cc).

24. The system of claim 22, wherein the controller is configured to control the waveform generator so that an increased pressure level of the LES is below a pressure level that prevents the patient from swallowing a bolus.

25. The system of claim 22, wherein the controller is configured to control the waveform generator so that an increased pressure level of the LES is below a pressure level that restricts the opening capacity of patient's LES when swallowing a bolus.

26. The system of claim 22, wherein the controller is configured to control the waveform generator so that the electrical stimulation does not inhibit a patient's esophageal motility.

27. A system for increasing pressure of a patient lower esophageal sphincter (LES), comprising: at least one electrode configured to contact the LES; a waveform generator coupled to the electrodes; a battery powering the waveform generator; and a controller configured to control the waveform generator to generate and apply an electrical pulse train to the LES through the electrodes to increase the pressure of the LES, the electrical pulse train being controlled by the controller so that an amount of electrical energy consumed from the battery when stimulating the LES is an energy amount that maintains an average pressure of the LES above a pressure level which reduces at least one of a frequency of occurrence or an intensity of acid reflux symptoms in the patient while maintaining at least a minimum charge on the battery to electrically power the waveform generator for a predetermined time period, wherein the controller is configured to control the waveform generator so that the increased pressure level of the LES is below a pressure level that prevents the patient from swallowing a bolus.

28. The system of claim 27, wherein the controller is configured to determine a stimulation time for stimulating the LES to reduce at least one of the frequency of occurrence or the intensity of acid reflux symptoms in the patient, and electrically power the waveform generator for the predetermined time period.

29. The system of claim 27, wherein the controller is configured to determine at least one of a pulse width, electrical current, frequency and energy of the electrical pulse train to reduce at least one of the frequency of occurrence or the intensity of acid reflux symptoms in the patient, and electrically power the waveform generator for the predetermined time period.

30. The system of claim 27, wherein the controller is configured to consume between 30 nano-amp hours and 3 micro-amp-hours of energy during a stimulation period to reduce the acid reflux symptoms in the patient for at least one hour, and does not consume more than 3 micro-amp hours of energy per stimulation period.

31. The system of claim 27, wherein the controller is configured to cumulatively consume between 300 nano-amp hours and 30 micro-amp-hours of energy over a plurality of stimulation periods to reduce the acid reflux symptoms in the patient for at least 24 hours, and does not consume more than 30 micro-amp hours of energy per day.

32. A method of treating a patient with acid reflux symptoms, wherein said patient has a lower esophageal sphincter (LES) and wherein said LES has a pressure, the method comprising: maintaining an average pressure of the LES above a pressure level which reduces at least one of a frequency of occurrence or an intensity of the acid reflux symptoms both during and after stimulation by applying an electrical pulse train to the LES through electrodes for a stimulation period to increase the pressure of the LES above the pressure level, and terminating the electrical pulse train for a rest period wherein at least one of an amplitude, frequency, or duration of said pulse train is defined such that the increased pressure of the LES is below a pressure level that prevents the patient from swallowing a bolus.

33. The method of claim 32, wherein the LES is repeatedly stimulated to maintain the average pressure of the LES in a pressure range which is above a first pressure level to at least one of the frequency of occurrence or the intensity of the acid reflux symptoms in the patient and below a second pressure level to allow the patient to swallow during both the stimulation period and rest period.

34. The method of claim 33, wherein a controller determines parameters of the electrical pulse train that maintain the average pressure of the LES above the pressure level during the rest period.

35. The method of claim 34, wherein the controller controls a waveform generator to stimulate the LES when the pressure of the LES decreases to a third pressure level during the rest period.

36. The method of claim 34, wherein the controller adjusts a length of the stimulation period and a length of the rest period to maintain the average pressure of the LES above the pressure level.

37. The method of claim 34, wherein the controller is configured to control the waveform generator to set a pulse width of the electrical pulse train in a range from about 1 µs to about 1 second.

38. The method of claim 34, wherein the controller is configured to control the waveform generator to set a frequency of the electrical pulse train in a range from about 1 Hz to about 100 Hz.

39. The method of claim 34, wherein the controller is configured to control the waveform generator to set a current of pulses in the electrical pulse train in a range from about 1 µAmp to about 50 mAmps.

40. The method of claim 34, wherein the controller is configured to perform a diagnostic test on the patient by controlling the waveform generator to vary parameters of the electrical pulse train to determine a pressure response of the LES based on different electrical stimulation.

41. The method of claim 32, wherein: achieving said pressure level occurs after a minimum period selected from the group consisting of at least 5 minutes, 10 minutes, 15 minutes, 30 minutes, 1 hour, 2 hours, 3 hours, 12 hours, 24 hours, or any time increment therein.

42. The method of claim 32, wherein: said electrical stimulation is initiated prior to a predetermined time; said predetermined time is associated with an acid reflux triggering event; and said initiation occurs prior to said predetermined time by a minimum period selected from the group consisting of at least 5 minutes, 10 minutes, 15 minutes, 30 minutes, 1 hour, 2 hours, 3 hours, 12 hours, 24 hours, or any time increment therein.

43. The method of claim 32, further comprising: programming said stimulation device, wherein said programming is dependent upon a plurality of stimulation parameters that determine the application of electrical stimulation to the patient LES, and wherein said stimulation parameters are selected, at least in part, to treat acid reflux without inhibiting patient swallowing.

44. The method of claim 32, wherein electrical stimulation is applied to the patient LES while the patient swallows, during periods of esophageal motility, or during esophageal peristalsis.

45. The method of claim 32, wherein electrical stimulation is applied to the patient LES in accordance with a preset period and wherein said preset period is not dependent upon a physiological state of a patient.

46. The method of claim 32, wherein electrical stimulation is applied to the patient LES in accordance with a preset period and wherein said preset period is not dependent upon the patient swallowing, esophageal motility, esophageal peristalsis, or being in a feeding state.

47. The method of claim 32, wherein electrical stimulation is applied to the patient LES that is not dependent upon a physiological state of the patient.

48. The method of claim 32, wherein electrical stimulation is applied to the patient LES that is not dependent upon a sensed physiological state of the patient.

49. The method of claim 32, wherein electrical stimulation is applied to the patient LES that is not dependent upon the patient swallowing, esophageal motility, esophageal peristalsis, or being in a feeding state.

50. The method of claim 32, wherein sufficient electrical stimulation is applied to the patient LES to increase said pressure but not to inhibit patient swallowing, esophageal motility, or esophageal peristalsis.

51. The method of claim 32, wherein electrical stimulation is applied to the patient LES causing an increase in said pressure of at least 5% only after an elapsed period of time of at least one minute.

52. The method of claim 32, wherein said electrical stimulation normalizes lower esophageal function, normalizes LES pressure, or increases LES pressure to a normal physiological range only after an elapsed period of time of at least one minute.

53. The method of claim 32, wherein said stimulation causes a non-instantaneous or delayed increase in said pressure.

54. The method of claim 32, wherein said electrical stimulation causes a delayed increase in said pressure and wherein said delayed increase in the pressure normalizes LES function, normalizes LES pressure, increases LES pressure to a normal physiological range, or increases LES pressure by at least 3%.

55. The method of claim 32, wherein said electrical stimulation causes an increase in said pressure after said electrical stimulation is terminated.

56. The method of claim 32, wherein said electrical stimulation has a first level, wherein said stimulation causes an increase in said pressure after said electrical stimulation is decreased from said first level.

57. The method of claim 32, wherein said electrical stimulation is applied in accordance with at least one on period, wherein said on period is between 1 second and 24 hours and is not triggered by, substantially concurrent to, or substantially simultaneous with an incidence of acid reflux, and at least one off period, wherein said off period is greater than 10 seconds.

58. The method of claim 32, wherein said electrical stimulation is applied having a current from a single electrode pair ranging from about 1 mAmp to about 8 mAmp.

59. The method of claim 32, wherein said electrical stimulation has a pulse duration within a range of 5 μsec to 1 second.

60. The method of claim 32, wherein said electrical stimulation has a pulse duration of approximately 1 msec.

61. The method of claim 32, wherein said electrical stimulation has a pulse duration of approximately 200 μsec.

62. The method of claim 32, wherein the device incorporates an accelerometer or inclinometer to measure patient positional activity; and applying electrical stimulation based upon one or more of the following parameters as measured by said accelerometer or inclinometer: time spent in the supine position or level of inclination.

63. A macrostimulator programmed, adapted to, or configured to perform the method of claim 32.

64. A macrostimulator comprising at least one electrode, an energy source, and a pulse generator in electrical communication with the at least one electrode and energy source, wherein said pulse generator is programmed, adapted to, or configured to perform the method of claim 32.

65. A macrostimulator implanted in a patient configured to perform the method of claim 32.

66. A macrostimulator implanted in a patient comprising at least one electrode, an energy source, and a pulse generator in electrical communication with the at least one electrode and energy source, wherein said pulse generator is programmed, adapted to, or configured to perform the method of claim 32.

67. A macrostimulator programmed, adapted to, or configured to perform the method of claim 32 wherein electrical stimulation is initiated, terminated or otherwise modified based upon sensed data.

68. A macrostimulator comprising at least one electrode, an energy source, and a pulse generator in electrical communication with the at least one electrode and energy source, wherein said pulse generator is programmed, adapted to, or configured to perform the method of claim 32 wherein electrical stimulation is initiated, terminated or otherwise modified based upon sensed data.

69. A macrostimulator implanted in a patient configured to perform the method of claim 32 wherein electrical stimulation is initiated, terminated or modified based upon sensed data.

70. A macrostimulator implanted in a patient comprising at least one electrode, an energy source, and a pulse generator in electrical communication with the at least one electrode and energy source, wherein said pulse generator is programmed, adapted to, or configured to perform the method of claim 32 wherein electrical stimulation is initiated, terminated, or otherwise modified based upon sensed data.

71. A macrostimulator programmed, adapted to, or configured to perform the method of claim 32 wherein electrical stimulation is initiated or terminated based upon sensed data and wherein the sensed data is at least one of LES pressure, esophageal pH, inclinometer data, temperature, or accelerometer data.

72. A macrostimulator comprising at least one electrode, an energy source, and a pulse generator in electrical communication with the at least one electrode and energy source, wherein said pulse generator is programmed, adapted to, or configured to perform the method of claim 32 wherein electrical stimulation is initiated or terminated based upon sensed data and wherein the sensed data is at least one of LES pressure, esophageal pH, inclinometer data, temperature, or accelerometer data.

73. A macrostimulator implanted in a patient configured to perform the method of claim 32 wherein electrical stimulation is initiated or terminated based upon sensed data and wherein the sensed data is at least one of LES pressure, esophageal pH, inclinometer data, temperature, or accelerometer data.

74. A macrostimulator implanted in a patient comprising at least one electrode, an energy source, and a pulse generator in electrical communication with the at least one electrode and energy source, wherein said pulse generator is programmed, adapted to, or configured to perform the method of claim 32 wherein electrical stimulation is initiated or terminated based upon sensed data and wherein the sensed data is at least one of LES pressure, esophageal pH, inclinometer data, temperature, or accelerometer data.

75. A method of treating a patient with acid reflux symptoms, the method comprising: (a) implanting a stimulation device in the patient to contact the patient LES, (b) applying electrical stimulation to the patient LES, and (b) maintaining an average pressure of the LES above a pressure level both during and after electrical stimulation for a stimulation period to increase the pressure of the LES above the pressure level, and terminating the electrical stimulation for a rest period wherein at least one of an amplitude, frequency, or duration of said electrical stimulation is defined such that the increased pressure of the LES is below a pressure level that prevents the patient from swallowing a bolus.

76. The method of claim 75, wherein: achieving said pressure level occurs after a minimum period selected from the group consisting of at least 5 minutes, 10 minutes, 15 minutes, 30 minutes, 1 hour, 2 hours, 3 hours, 12 hours, 24 hours, or any time increment therein.

77. The method of claim 75, wherein: said electrical stimulation is initiated prior to a predetermined time; said predetermined time is associated with an acid reflux triggering event;
and said initiation occurs prior to said predetermined time by a minimum period selected from the group consisting of at least 5 minutes, 10 minutes, 15 minutes, 30 minutes, 1 hour, 2 hours, 3 hours, 12 hours, 24 hours, or any time increment therein.

78. The method of claim 75, further comprising: programming said stimulation device, wherein said programming is dependent upon a plurality of stimulation parameters that determine the application of electrical stimulation to the patient LES, and wherein said stimulation parameters are selected, at least in part, to treat acid reflux symptoms without inhibiting patient swallowing.

79. The method of claim 75, wherein electrical stimulation is applied to the patient LES while the patient swallows, during periods of esophageal motility, or during esophageal peristalsis.

80. The method of claim 75, wherein electrical stimulation is applied to the patient LES in accordance with a preset period and wherein said preset period is not dependent upon a physiological state of a patient.

81. The method of claim 75, wherein electrical stimulation is applied to the patient LES in accordance with a preset period and wherein said preset period is not dependent upon the patient swallowing, esophageal motility, esophageal peristalsis, or being in a feeding state.

82. The method of claim 75, wherein electrical stimulation is applied to the patient LES that is not dependent upon a physiological state of the patient.

83. The method of claim 75, wherein electrical stimulation is applied to the patient LES that is not dependent upon a sensed physiological state of the patient.

84. The method of claim 75, wherein electrical stimulation is applied to the patient LES that is not dependent upon the patient swallowing, esophageal motility, esophageal peristalsis, or being in a feeding state.

85. The method of claim 75, wherein sufficient electrical stimulation is applied to the patient LES to increase said pressure but not to inhibit patient swallowing, esophageal motility, or esophageal peristalsis.

86. The method of claim 75, wherein electrical stimulation is applied to the patient LES causing an increase in said pressure of at least 5% only after an elapsed period of time of at least one minute.

87. The method of claim 75, wherein said electrical stimulation normalizes lower esophageal function, normalizes LES pressure, or increases LES pressure to a normal physiological range only after an elapsed period of time of at least one minute.

88. The method of claim 75, wherein said stimulation causes a non-instantaneous or delayed increase in said pressure.

89. The method of claim 75, wherein said electrical stimulation causes a delayed increase in said pressure and wherein said delayed increase in the pressure normalizes LES function, normalizes LES pressure, increases LES pressure to a normal physiological range, or increases LES pressure by at least 3%.

90. The method of claim 75, wherein said electrical stimulation causes an increase in said pressure after said electrical stimulation is terminated.

91. The method of claim 75, wherein said electrical stimulation has a first level, wherein said stimulation causes an increase in said pressure after said electrical stimulation is decreased from said first level.

92. The method of claim 75, wherein said electrical stimulation is applied in accordance with at least one on period, wherein said on period is between 1 second and 24 hours and is not triggered by, substantially concurrent to, or substantially simultaneous with an incidence of acid reflux, and at least one off period, wherein said off period is greater than 10 seconds.

93. The method of claim 75, wherein said electrical stimulation is applied having a current from a single electrode pair ranging from about 1 mAmp to about 8 mAmp.

94. The method of claim 75, wherein said electrical stimulation has a pulse duration within a range of 5 μsec to 1 second.

95. The method of claim 75, wherein said electrical stimulation has a pulse duration of approximately 1 msec.

96. The method of claim 75, wherein said electrical stimulation has a pulse duration of approximately 200 μsec.

97. The method of claim 75, wherein the device incorporates an accelerometer or inclinometer to measure patient positional activity; and applying electrical stimulation based upon one or more of the following parameters as measured by said accelerometer or inclinometer: time spent in the supine position or level of inclination.

98. A method of treating a patient with acid reflux symptoms, the method comprising: (a) implanting the stimulation device in the patient to contact the patient LES; (b) applying electrical stimulation to the patient LES; (b) measuring one or more parameters selected from the group consisting of patient feed state including type of feed; patient position; patient activity; patient reflux profile; LES pressure; LES electrical activity; LES mechanical activity gastric pressure; gastric electrical activity; gastric chemical activity; gastric temperature; gastric mechanical activity; patient intuition; vagal neural activity; and, splanchnic neural activity; (c) inputting the collected data into an algorithm; and (d) applying electrical stimulation based upon a summary score calculated by said algorithm to maintain an average pressure of the LES above a pressure level both during and after electrical stimulation for a stimulation period to increase the pressure of the LES above the pressure level, and terminating the electrical stimulation for a rest period wherein at least one of an amplitude, frequency, or duration of said electrical stimulation is defined such that the average pressure of the LES is below a pressure level that prevents the patient from swallowing a bolus.

* * * * *